(12) United States Patent
Myllyntausta et al.

(10) Patent No.: US 8,993,281 B2
(45) Date of Patent: Mar. 31, 2015

(54) **GENETICALLY MODIFIED *ACINETOBACTER* HOSTS FOR LIPID PRODUCTION**

(75) Inventors: Suvi Myllyntausta, Nokia (FI); Virpi Kivinen, Tampere (FI); Antti Larjo, Tampere (FI); Tommi Aho, Tampere (FI); Perttu Koskinen, Helsinki (FI); Matti Karp, Littoinen (FI); Ville Santala, Nokia (FI)

(73) Assignee: Neste Oil Oyj, Espoo (FI)

( * ) Notice: Subject to any disclaimer, the term of this patent is extended or adjusted under 35 U.S.C. 154(b) by 0 days.

(21) Appl. No.: 13/326,589

(22) Filed: Dec. 15, 2011

(65) Prior Publication Data

US 2012/0151833 A1 Jun. 21, 2012

Related U.S. Application Data

(60) Provisional application No. 61/424,387, filed on Dec. 17, 2010.

(30) Foreign Application Priority Data

Dec. 17, 2010 (EP) .................................... 10195551

(51) Int. Cl.
| | |
|---|---|
| *C12P 7/64* | (2006.01) |
| *C12N 1/22* | (2006.01) |
| *C12N 15/74* | (2006.01) |
| *C12P 1/00* | (2006.01) |
| *C07K 14/195* | (2006.01) |

(Continued)

(52) U.S. Cl.
CPC .............. *C12P 7/649* (2013.01); *C07K 14/195* (2013.01); *C12N 9/0008* (2013.01); *C12N 9/20* (2013.01); *C12P 7/6463* (2013.01); *Y02E 50/13* (2013.01)
USPC ........... 435/134; 435/252.1; 435/471; 435/41

(58) Field of Classification Search
None
See application file for complete search history.

(56) References Cited

U.S. PATENT DOCUMENTS 4,567,144 A * 1/1986 Neidleman et al. ............ 435/134
6,143,538 A 11/2000 Somerville et al.
(Continued)

FOREIGN PATENT DOCUMENTS

| DE | 102004052115 | 4/2006 |
|---|---|---|
| EP | 1396531 | 3/2004 |

(Continued)

OTHER PUBLICATIONS

Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*

(Continued)

*Primary Examiner* — Alexander Kim
(74) *Attorney, Agent, or Firm* — Andrus Intellectual Property Law, LLP

(57) ABSTRACT

The present invention relates to a genetically modified *Acinetobacter* host for lipid production. The *Acinetobacter* host has been genetically modified to be deficient of one or more of genes A) a gene encoding fatty acyl-CoA reductase (EC1.2.1.n2), wherein said host is capable of increased production of TAGs and/or of total lipids compared to the parent host; and/or B) a gene encoding lipase (EC:3.1.1.3), a gene encoding pyruvate dehydrogenase (EC:1.2.2.2), and/or gene ACIAD 2177, or functional equivalents of any of said genes, wherein said host is capable of increased production of wax esters and/or total lipids compared to the parent host.

8 Claims, 5 Drawing Sheets

(51) Int. Cl.
C12N 9/02 (2006.01)
C12N 9/20 (2006.01)

(56) References Cited

U.S. PATENT DOCUMENTS 7,691,792 B1  4/2010 Fisher et al.
2003/0145350 A1  7/2003 Spener et al.

FOREIGN PATENT DOCUMENTS

| EP | 1398364 | 3/2004 |
| EP | 1741767 | 1/2007 |
| EP | 1741768 | 1/2007 |
| WO | 2007136762 | 11/2007 |
| WO | 2008113041 | 9/2008 |
| WO | 2008119082 | 10/2008 |
| WO | 2009009391 | 1/2009 |
| WO | 2010036951 | 4/2010 |

OTHER PUBLICATIONS

Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Branden and Tooze, Introduction to Protein Structure (1999), 2nd edition, Garland Science Publisher, pp. 3-12.*
Altschul et al., "Gapped BLAST and PSI-BLAST: a new generation of protein database search programs", Nucleic Acids Research, 1997, 25(17):3389-3402.
Arabolaza et al., "Multiple Pathways for Triacyglycerol Biosynthesis in *Streptomyces coelicolor*", Applied and Environmental Microbiology, May 2008, 74(9):2573-2582.
Connor et al., "Microbial production of advanced transportation fuels in non-natural hosts", Current Opinion in Biotechnology, 2009, 20:307-315.
De Berardinis et al., "*Acinetobacter baylyi* ADP1 as a model for metabolic system biology", Current Opinion in Microbiology, 2009, 12:568-576.
De Berardinis et al., "A complete collection of single-gene deletion mutants of *Acinetobacter baylyi* ADP1", Molecular Systems Biology, 2008, 4(174):1.
Fixter et al., "Structure, distribution and function of wax esters in *Acinotobacter calcoaceticus*", Journal of General Microbiology, 1986, 132:3147-3157.
Geigert et al., "Further aspects of wax ester biosynthesis by *Acinetobacter* sp. HO1-n", JAOCS, Nov. 1984, 61 (11):1747.
Ishige et al., "Long-chain aldehyde dehydrogenase that participates in n-Alkane utilization and wax ester synthesis in *Acinetobacter* sp. strain M-1", Applied and Environmental Microbiology, Aug. 2000, 66(8):3481-3486.
Ishige et al., "Wax ester production from n-Alkanes by *Acinetobacter* sp. strain M-1: Ultrastructure of cellular inclusions and role of Acyl Coenzyme A Reductase", Applied and Environmental Microbiology, Mar. 2002, 68 (3):1192-1195.
Kalscheuer et al., "A novel bifunctional wax ester Synthase/Acyl-coA:Diacyglycerol Acyltransferase mediates wax ester and triacylglycerol biosynthesis in *Acinetobacter calcoaceticus* ADP1", Journal of Biological Chemistry, Mar. 7, 2003, 278(10):8075-8082.
Kalscheuer et al., "In vitro and in vivo biosynthesis of wax diesters by an unspecific bifunctional wax ester synthase/acyl-CoA:diacyglycerol acyltransferase from *Acinetobacter calcoaceticus* ADP1", Eur. J. Lipid Sci Technol., 2003, 105:578-584.
Kalscheuer et al., "Microdiesel: *Escherichia coli* engineered for fuel production", Microbiology, 2006, 152:2529-2536.
Kalscheuer et al., "Neutral lipid biosynthesis in engineered *Escherichia coli*: Jojoba oil-like wax esters and fatty acid butyl esters", Applied and Environmental Microbiology, Feb. 2006, 72(2):1373-1379.
Krehenbrink et al., "Evaluation of non-cyanobacterial genome sequences for occurrence of genes encoding proteins homologous to cyanophycin synthetase and cloning of an active cyanophycin synthetase from *Acinetobacter* sp. strain DSM 587", Arch Microbiol, 2002, 177:371-380.
Metzgar et al., "*Acinetobacter* sp. ADP1: an ideal model organism for genetic analysis and genome engineering", Nucleic Acids Research, 2004, 32(19):5780-5790.
Miller, "Quantifying western blots without expensive commercial quantification software", Stuff, 2007, available at www.lukemiller.org/journal/2007/08/quantifying-western-blots-without.html, Mar. 5, 2012.
Na et al., "Construction and optimization of synthetic pathways in metabolic engineering", Current Opinion in Microbiology, 2010, 13:363-370.
Ratledge et al., "Microbial and algal oils: do they have a future for biodiesel or as commodity oils?", Lipid Technology, Jul. 2008, 20(7):155.
Reiser et al., "Isolation of mutants of *Acinetobacter calcoaceticus* deficient in wax ester synthesis and complementation of one mutation with a gene encoding a fatty acyl coenzyme a reductase", Journal of Bacteriology, May 1997, 179(9):2969-2975.
Rice et al., "EMBOSS: The European molecular biology open software suite", TIG, Jun. 2000, 16(6):276.
Santala et al., "Production of a biotinylated single-chain antibody fragment in the cytoplasm of *Escherichia coli*", Journal of Immunological Methods, 2004, 284:165-175.
Stoveken et al., "Bacterial acyltransferases as an alternative for lipase-catalyzed acylation for the production of oleochemicals and fuels", Angew. Chem. Int. Ed., 2008, 47:3688-3694.
Tauriainen et al., "Recombinant luminescent bacteria for measuring bioavailable arsenite and antimonite", Applied and Environmental Microbiology, Nov. 1997, 63(11):4456-4461.
Uthoff et al., "Thio wax ester biosynthesis utilizing the unspecific bifunctional wax ester synthase/acyl coenzyme A: Diacylglycerol Acyltransferase of *Acinetobacter* sp. strain ADP1", Applied and Environmental Microbiology, Feb. 2005, 71(2):790-796.
Waltermann et al., "Mechanism of lipid-body formation in prokaryotes: how bacteria fatten up", Molecular Microbiology, 2005, 55(3):750-763.
Yu et al., "Metabolic engineering for triacyglycerol production from engineered *Saccharomyces cerevisiae* using glycerol", Special Abstracts, Journal of Biotechnology, 2010, 150S:S5344.
European Search Report for EP10195551 dated May 25, 2011.
Kalscheuer et al., "In vitro and in vivo biosynthesis of wax diesters by an unspecific bifunctional wax ester synthase/acyl-CoA:ciacyglycerol acyltransferase fromj *Acinetobacter calcoaceticus* ADP-1", Eur. J. Lipid Sci. Technol., 2003, 105:578-584.
Santala et al., "Improved tiacylglycerol production in *Acinetobacter baylyi* ADP1 by metabolic engineering", Microbial Cell Factories, 2011, 10:36.
International Search Report for PCT/FI2011/051108 dated Mar. 29, 2012.
Written Opinion for PCT/FI2011/051108 dated Mar. 29, 2012.
Deberardinis et al., "A Complete Collection of Single-Gene Deletion Mutants of *Acinetobacter baylyi* ADP1", Molecular Systems Biology, 2008, 4(174):1-15.
Deberardinis et al., "A Complete Collection of Single-Gene Deletion Mutants of *Acinetobacter baylyi* ADP1", Molecular Systems Biology, 2008, 4(174):1-15. Online Supplementary Material 1.
Deberardinis et al., "A Complete Collection of Single-Gene Deletion Mutants of *Acinetobacter baylyi* ADP1", Molecular Systems Biology, 2008, 4(174):1-15.Online Supplementary Material 2.
Deberardinis et al., "A Complete Collection of Single-Gene Deletion Mutants of *Acinetobacter baylyi* ADP1", Molecular Systems Biology, 2008, 4(174):1-15. Online Supplementary Material 3.
Deberardinis et al., "A Complete Collection of Single-Gene Deletion Mutants of *Acinetobacter baylyi* ADP1", Molecular Systems Biology, 2008, 4(174):1-15. Online Supplementary Material 4.
Deberardinis et al., "A Complete Collection of Single-Gene Deletion Mutants of *Acinetobacter baylyi* ADP1", Molecular Systems Biology, 2008, 4(174):1-15. Online Supplementary Material 5.
Deberardinis et al., "A Complete Collection of Single-Gene Deletion Mutants of *Acinetobacter baylyi* ADP1", Molecular Systems Biology, 2008, 4(174):1-15. Online Supplementary Material 6.

* cited by examiner

SEQUENCE LISTING

```
<160> NUMBER OF SEQ ID NOS: 32

<210> SEQ ID NO 1
<211> LENGTH: 912
<212> TYPE: DNA
<213> ORGANISM: Acinetobacter baylyi
```

<400> SEQUENCE: 1

```
ttgatatcaa tcagggaaaa acgcgtgaac aaaaaacttg aagctctctt ccgagagaat        60
gtaaaaggta aagtggcttt gatcactggt gcatctagtg gaatcggttt gacgattgca       120
aaaagaattg ctgcggcagg tgctcatgta ttattggttg cccgaaccca agaaacactg       180
gaagaagtga aagctgcaat tgaacagcaa gggggacagg cctctatttt tccttgtgac       240
ctgactgaca tgaatgcgat tgaccagtta tcacaacaaa ttatggccag tgtcgatcat       300
gtcgatttcc tgatcaataa tgcagggcgt tcgattcgcc gtgccgtaca cgagtcgttt       360
gatcgcttcc atgattttga acgcaccatg cagctgaatt actttggtgc ggtacgttta       420
gtgttaaatt tactgccaca tatgattaag cgtaaaaatg ccagatcat caatatcagc        480
tctattggtg tattgccaa tgcgacccgt ttttctgctt atgtcgcgtc taaagctgcg        540
ctggatgcct tcagtcgctg tctttcagcc gaggtactca agcataaaat ctcaattacc       600
tcgatttata tgccattggt gcgtacccca atgatcgcac ccaccaaaat ttataaatac       660
gtgcccacgc tttccccaga agaagccgca gatctcattg tctacgccat tgtgaaacgt       720
ccaaaacgta ttgcgacgca cttgggtcgt ctggcgtcaa ttacctatgc catcgcacca       780
gacatcaata atattctgat gtcgattgga tttaacctat tcccaagctc aacggctgca       840
ctgggtgaac aggaaaaatt gaatctgcta caacgtgcct atgcccgctt gttcccaggc       900
gaacactggt aa                                                          912
```

<210> SEQ ID NO 2
<211> LENGTH: 969
<212> TYPE: DNA
<213> ORGANISM: Acinetobacter baylyi

<400> SEQUENCE: 2

```
atgaaattca aattattatt tacaactta ttgctggttc taacccaacc tgtatttgca         60
accagtccaa ttcagaatcc aactacatct tttgtcatat ccgattatgc aaagaccaaa       120
tatccgattg ttctctcaca tggactattc ggttttaata aattaggcac agaagccttt       180
gggttagatt attggtatca gattccacaa gatttggcca gaaatggtgc caatgtctgg       240
gtaacccgtc aatctactgc caatacatct gaatttcgag cgaacaatt acttgctgaa        300
gttcaggaca ttctggccat tacaggcgca caaaaagtta atctgattgg gcatagtcat       360
ggctcccaaa ctgtacgcta tgttgctggt gttctccctg caaatattgc ttccgtttca       420
acgattggtg gccctgccaa aggtgcccca ctggctgatc tgatttataa acactggct        480
ggcacaccat tagaagcgcc tattgcgacc attttcaatg tcgcaatgaa ttttattacg       540
ataggacaat tcgatgatcc gcagaaatat ccaatgaact ctgtcggtgc agcgtatagt       600
ctatccactg aaggtgctgg taaatttaat gcaatctttc ctgctggcgt accaacgact       660
gcatgcggtc aaggtgaatc ttctgtcaat ggtgtacgtt attattcatg gagcggtgct       720
tctccattaa ccaatccact cgatccttca gattatggcc tgagcttgac cagtgtattt       780
agtggcaaaa acaatgacgg gctggtacct tcatgtagca gtcacttggg tacagtaatt       840
cgagataatt acgtatggaa tcatctggat gaagtcaatc aaattctggg tttacgatct       900
attttttgcac aagaccccgt atccatcttt agacaacatg ccaatcgtct caaaggtcaa       960
aatctataa                                                              969
```

```
<210> SEQ ID NO 3
<211> LENGTH: 1722
<212> TYPE: DNA
<213> ORGANISM: Acinetobacter baylyi

<400> SEQUENCE: 3
atgagtaatc aaaaagtatc cgatattatc atcgaagtgc ttgagcaagc aggcgttcag      60
cgctgttacg gtattgtggg tgacaccttg aaccatgtca ccgactccat gtcaaaaagc     120
aagattgaat ggattcatgt gcgccatgaa gaagttggtg gctttgcagc aggtacagat     180
gcattactca gtggtcactt aaccgcatgt gctggttctt gcgggccggg cagtctgcac     240
tttattaatg gcttgtatga atcacaccga atcgtgcgc ccgttatttt gattgcgagc      300
cagatttcga ccgaaatggc aggatttatc gactttccgc aatacgtcga ttttaaatcg     360
gtttatgcga aaaattcggt cttctgtgaa gaaattactc aaccctcaca agctagacat     420
atcatgagca tggcctgtca ggcagcactc aataaacgcg tgtcgctgt ggtcatcgtg      480 ccagccaata tcagtgaagc atcggctgaa gcgggtctac ctttcgtgcc acgtcatgtt     540
gaacctgata ttttgccaaa caaagctgaa ctgcatcaaa tggttgagct gatttcccag     600
catcaaaaaa ttggaattta tgcaggtgcg gggtgtgaag cgcacatga tcagttaatt      660 gcgtttgctg aaaagttaaa agcccctgtg gcgcatacct cacgtgccaa agattttgtg     720
gagtacgata acccatacaa catgggcatg acgggtattt tggcaataa agcaggttat      780 cacacgctca tggattgtga tttactgatt ttgctgggtg ccgattttgc atgggcacag     840
tactatccaa gtcatgccaa aatcttgcag attgatattg atccgacaca tttagggcga     900
cgtcacccaa ttacactggg tgcggtaggt aaaatctcat cgacgctcga tgccttatta     960
ccattgcttg aaacgcgtca agaacgcgca ttttttagatc attgtcttga actgaaacat    1020
cacagtgatg aaacacggca taagaagaa cgtgtcggaa agacgggct gattcatcca      1080 cagtatctgg tgtcgttgct taaccgttat gccgatcagg atgcaatttt ctttggtgat    1140
gggggctcac cgatggtgtg ggtactcaga catatcgatg tgaatggcaa acgtcgaacc    1200
tttaccagtt tgttgcatgg cacgatggcc aatgccatgc cccaggcgct ggcgcacaa     1260 aaagcttttc cgaatcgcca gattattgcg ctgtgtggcg atggtggatt agccatgtta    1320
cttggtgatt tactcactac gattcaggaa aaattaccga ttaaaattgt ggtatttaac    1380
aacagctcgc ttaattttgt tgagcttgaa caaaaagtcg aaggcttgct tgatcattat    1440
accgacttgc tcaatcctga ttttggcaag cttgccagtg tgatcgggct acatgggcag    1500
actgtgacgc atggcgatgg cttggagcag gcagttgaaa acttcttaaa gcatgatggt    1560
ccagcattac tcaatgtgca taccaatccg atggaactgg tgatgccgcc agatccgaat    1620
ctgaatcaag tctcgtccac ttcactttat gcaattaagg ccttgatgtc gggtcgagta    1680
gatgacgtta aaaatttgtt ggtcaataat ttcattaaat aa                      1722

<210> SEQ ID NO 4
<211> LENGTH: 642
<212> TYPE: DNA
<213> ORGANISM: Acinetobacter baylyi

<400> SEQUENCE: 4
atggaccaga tcagaccatt tccccagact gactttattg atcaagctga ggaagaagaa      60
gcgattcgtt tgatcgctgc accagatcta aaagaatggg taataacaaa tttcttaacg     120
ctgggcggtg agctacataa cccggatcat gaccatatcg ctgagctact tcacgatgac    180
```

```
gaaacatttc tagcctttgc ttgggcatca tctgcattta cacgggctaa gcgcatggtg      240
ttggggcaat gtgagaaagt catgttcaac caaggtgggt ggaaaaaggc acggcaagaa      300
caacagatgc gggattggtt tggctttgta cctgtttatc tcattacgat tgatgccagc      360
ttttgcgagc aagcgactga tcgagagttt tgtgctctga ttgaacatga gctttatcat      420
attggtgttg agcgtgatgg agacggtgaa attgtctata gcgaccacac tggtctgcct      480
aagcattact ggcgggcca cgacgtagaa gagttcgttg cgttgtgaa gcgctggggc       540 gcgagtgatg acattaagcg tcttgttgaa gtcgcaaagc aggcgccgtt tgtatcagaa      600
aagaatatag ctgcaagttg tgggacgtgt tgattaagt ag                         642
```

<210> SEQ ID NO 5
<211> LENGTH: 396
<212> TYPE: DNA
<213> ORGANISM: Acinetobacter baylyi

<400> SEQUENCE: 5

```
ttgttctgcg aaattgtaat gaaccaatct tctccataca aaggtaaaca aggcttaaaa      60
cgtattatca atgccacagg ttattctatt tcaggattta aaatcgcatt taagcaagaa     120
gcagcctttc gccaaattat ttttctaaac ttgatccttat tgccgatcaa tttgagttta    180
tcacttcgtc catctgaaca tgcaatcttg tttgctgtgg gtctgattgc tgtcattgta    240
gagctgttta actctgcaat tgaggcagcg attgatcgga tatctctgga tcgacatgaa    300
ctgtctaaaa atgcaaaaga catgggaagt gctgcacaat gtgttgcgct gattatgatt    360
gcgttgacgt ggactattat tttattttgg gcataa                              396
```

<210> SEQ ID NO 6
<211> LENGTH: 1899
<212> TYPE: DNA
<213> ORGANISM: Acinetobacter baylyi

<400> SEQUENCE: 6

```
atgggcgcga taaaccctaa agaagattat tcaaatattc aaaacctcac ttttgatgct      60
gtcatcgtag gtggcggtgg ttctggtatg cgtgcttctt atcagttggc acaagctggt     120
ttgaaagttg cggtactcac caaagtattc ccaacccgtt ctcatacagt ggcagcgcag     180
ggtggtattg tgcttcact aggcaacatg caggaagaca actggcattt ccattttttac     240 gatacagtaa aaggttctga ctggttaggt gaccaagacg ccattgaatt tatgacacgt     300
gaagcgccaa aagttgtata tgagcttgaa cacttaggta tgccatttga ccgtaacgca     360
gatggtacga tctatcaacg tccgtttggt ggtcactctg caaactatgg tgataaacca     420
gttccacgtg cttgtgctgc tgctgaccgt acaggtcatg cgctattgca taccttgtat     480
caaagcaacg tcaaaatggg cactcagttt ttcgttgagt ggattgcgct tgacttgatc     540
cgtaatgaag caggtgatgt actcggtgta actgcttacg accaggaaac aggtaatatt     600
gcagtattcc aagccaaagc gactttgttt gctacaggtg gtgcaggtcg tgtttaccgt     660
gcatctacca acgcttatat caatactggt gatggtcttg gtatggctgc acgtgcaggt     720
attccattgc aagatatgga attctggcaa ttccacccaa caggtgtagc gggtgcgggc     780
gtacttctga ccgaaggctg tcgtggtgaa ggtgcgattc ttcgtaacaa agatggtgag     840
ccgttcatgg aacgttatgc accaactttg aaagacttgg cgccgcgtga ctttgtttca     900
cgttcaatgg accaagaaat taagaaggt cgtggctgtg ccctaaagc ggattatatc       960 ttgctcgata tgactcactt aggtgcggat accattatga agcgtttacc atctgtattt     1020
```

```
gagattggta aaaaattcgc aaacgtggat atcaccaaag agccaattcc ggttgtaccg    1080
acgattcatt atcaaatggg tggtattcca accaatattc atggtcaggt ggtggttcca    1140
gtggcaactg aaaaccttca cttggaagcg cattataaca atgcgaccaa agaatatact    1200
tttgagacca actgtccaga tttcgtaaaa ccagtaaaag ttttttatgc gattggtgaa    1260
tgttcttgcg tatctgtaca tggtgcaaac cgtttgggta ccaactcttt gcttgacctg    1320
gttgtatttg gtaaagccgc gggtgagcat atcattgatt atgtgaccaa gcatcatggt    1380
gatgaatatg caccgcttcc aacagatgta ttagagagta cattaaaacg tattcgtcat    1440
ctggatgaat caacttctgg tgaaaatgcg caagaagttg cagatgcgat tcgtgacatt    1500
gtgcaggatc atgctgcagt attccgtact caagagttgc tggatgaagg tgtaagacaa    1560
attcttgcgc tagagccacg agttcgcaat atttacttaa aagacaaatc taaggtattt    1620
aacactgcac gtgtagaggc tttggaggtt gaaaacctgt atgaagttgc gaaagcaaca    1680
ttgatttcgg ctgccgcacg taaagagtgt cgtggtgcgc atacagttgt cgattatgaa    1740
ttggcgccag atcatcctga ttacccatat ggtcgtcgtg atgatgagtg gatgaagcat    1800
acactgtggt attcggcaga taaccgtctt gaatacaagc ctgtgcgtta cgttccatta    1860
acagttgacg caattccacc tgcaccacgt acattctaa                           1899

<210> SEQ ID NO 7
<211> LENGTH: 1524
<212> TYPE: DNA
<213> ORGANISM: Acinetobacter baylyi

<400> SEQUENCE: 7
atggtgatga caacttctgc ttcactccca ctatacgata ttgtggtcgt cggtggtggc     60
attaatggta ttggtattgc caatgatgct gctggaaggg gcctatcggt tttttttgtgt    120 gaaaaagatg attttgctag ccacacatct tctgccagca gtaaattaat tcatggtgga    180
ttgcgatatc tggagcatta tgaatttcgt ttggtacgag aggctttagc agagcgtgaa    240
gttttgatgg caaaagcacc tcaccttgtg cgcccccctgc gttttatttt gccttatcaa    300
gcacatttac gttctgaatg gctgatccgt tctggactat tcctttatga tcatttaggt    360
aaacgaaaga aattaacggc ttctaaaaag atcactttcg attcggcaag tccgctaaaa    420
tctgaaattt ctaaaggctt tgaatatgcc gactgtacgg tagatgatgc gcgtttggtt    480
attatcaatg cgattcaagc gagagaaaaa ggtgcagaac ttgtaacgca taccgagtgt    540
ttgtctgcag aaatagtaga tgatgttttgg ttgattacct tacagcatcg gcaagtacct    600
tatcaaattc gtgccaaagt gctcattaat gcaactggtc cttgggtaga atcttttctc    660
aagtctcaac ttaaacagca ttcacccttat aaaaattcggc atattcaagg tagtcatctt    720
attgtggcga aactttatga ggataaccat gcctatatat tgcaaaatga agatggacga    780
attgtatttg tcattcccta tctgaatgac tttagtttga ttggcacgac agatcaggtt    840
tatttagatg atttgaatct ggtgaatatc acgcaacagg aaataagtta tctcttggat    900
gtagtgaatc ggcactttaa aacagttctg actcgtgcag atattataca gacttattct    960
ggagtcaggc ctttatgtga tgatgaatct gatcagccgt ctgctataac gcgtgattat   1020
acattggcgc tcactatggt ttcagaggtt gctccattac tttcggtatt tggtggaaaa   1080
ttaacaacat atcgcaaact agctggttct gcacttgaac agttgaagtt attttttcca   1140
gatatgaccc cctcatggac agaatacgag ccttttacctg gaggagaata ctttaagggg   1200
caagataaat tggtgaatgc gattcagcta cgtataaagg ggattgcttc tgaacttgca   1260
```

| | |
|---|---:|
| aagcgctggg cgacgagtta cggaacccgt gtctggaaat tattacaggg tgtttattcg | 1320 |
| gaagaagatt ttgggatcta ctttggacat gggctatatc agcttgaagt agattatctc | 1380 |
| gtcaaagtag aatgggtcga gtcagcagat gatgtgttat ggcgtcgcac caagttgggt | 1440 |
| tttagattta atcagaatga gattttggtg ttacaagact atttgatcag tctcgtcgtt | 1500 |
| ggcgaacaag gtaagattgc ataa | 1524 |

<210> SEQ ID NO 8
<211> LENGTH: 1062
<212> TYPE: DNA
<213> ORGANISM: Acinetobacter baylyi

<400> SEQUENCE: 8

| | |
|---|---:|
| atgagacaaa cgattttagc tgtattgtct ttatctacga ttgctgcact cttaactggg | 60 |
| tgtggtggtg atatggtact tctaaactca aaaggtccag taggtcaagg tcaaagtaac | 120 |
| ttgatgatga ctgcgatcta ccttatgtta ttggtggtca ttccatcagt aatcatggca | 180 |
| ttatggttta gttggaaata tcgcgcgtcg aataaagatg cagactataa acctacatgg | 240 |
| gcgcactcta ctgcaattga aattgtagtt tggggtgtcc ctgtcattat tattggtatt | 300 |
| ctagcttggt taacttggtg gggctcccac aagtacgacc cttaccgtcc tttagaatca | 360 |
| gataaagcac ctttaactat tcaggttatt gctgaacagt ttaaatggat ttttgtctat | 420 |
| cctgaacaaa acatcgcaac ggtaaatgaa gtacgcttcc cagaaaaaac cccgttaagc | 480 |
| tttaagatca cttctaactt tacaatgaac tctttttca ttccacagtt aggcggtcag | 540 |
| atctatgcga tggctggcat gcaaactcac ttacacttaa tggcagatca gccaggtgtt | 600 |
| ttccgtggca tgtcatctaa ctattcaggt tatggttct cacaaatgca ttttaaagca | 660 |
| tatagtgtga ctgaagctga atttacacaa tgggtagatg cagttaaagc aggtaaaggt | 720 |
| actggtgtta atcctgaagc aattcagaaa ggtatacttg atcaagctga acttgcaacg | 780 |
| cttaaagacg gtgatcgttc taagcatcaa attgaagcgc ttgtacatcg tgcacaagct | 840 |
| gcaggtgatg cagaagcctt agcgaaagct gaagcaatga accgttccc gaataagcca | 900 |
| catcctgtga cttactattc ttcagttgaa ccaaaattgt ttgaaactgt cattaacaga | 960 |
| tatatgagca actatcacgg agctgatcat tcagctactg ctgaacatgg ttcacaagct | 1020 |
| catgctgcta atgcacatgc aactgcttct gtagaggaat aa | 1062 |

<210> SEQ ID NO 9
<211> LENGTH: 1989
<212> TYPE: DNA
<213> ORGANISM: Acinetobacter baylyi

<400> SEQUENCE: 9

| | |
|---|---:|
| atgttgttat taggtaaaact cggatgggac tcaatcccta aagagccaat tgtactagtg | 60 |
| acaatggtct taatggctat tggtgcaatt gcagttctag gcggtatcac ctacttcaaa | 120 |
| aaatggggtt acctctggaa agaatggttt attacagtag accataaaaa aattggtatt | 180 |
| atgtacatcc ttgtatctgt cgtcatgctt ttgcgtggtt tcgccgatgc aattatgatg | 240 |
| cgtcttcaac tgttccttgc taaaggtggc ggtgaaggtt atttacatcc agaccattac | 300 |
| gaccagatct tcaccgcgca tggcgtgatc atgatcttct tcgtagcaat gggtcttgtt | 360 |
| gtgggtatga tgaatatctc tgtaccactt caaattggtg cacgtgacgt tgcattcccg | 420 |
| ctacttaact ctttaagctt ctggttgttt gctggtgcag ctggcttgat gatggcatct | 480 |
| ctcgtactcg gtgagtttgc tgctacaggc tggatggcat accctcctct ttctggtatt | 540 |

```
caatactctc ctggtgttgg tgtcgattac tatatctggg cactgcaagt ctcaggtctt    600
ggtacgcttt tatctggtgt aaactttttt gtgaccatca ttaaaatgcg tgcgccaggc    660
atgaagttga tggacatgcc aattttaca tggacatcat tatgtacagc ggttttgatc    720
attgcatcat tccctgtctt aacagccacc cttgccatgt aacgctaga ccgttacttt    780 ggtttccatt tcttcacaaa tgagcttggt ggtagtccaa tgctgtatgt gaacttgatc    840
tggacatggg gtcacccaga agtatatatc ttggtattac ctgcatttgg tttgtattca    900
gagattgttg caaccttctc tcgcaaagca ttgtttggtt ataaatcaat ggtatatgca    960
acgattgcaa ttactgtatt ggcattcgtt gtgtggttac accacttctt taccatgggt   1020
gcaggtgcaa acgttaacgc gttcttcggt atcatgacca tgattattgc aatccctaca   1080
ggggtgaaaa ttttctcttg gttatttacc atgtacaaag acgtatctc gttcgaaaca   1140 ccaatgctct ggacacttgg tttccttgtg acgtttggta ttggcggttt aaccggcgta   1200
ctaatggctg taccaccagc agacttttg gttcataact cattattcct cattgctcac   1260
ttccataacg taattattgg tggtgttgta tttggtatgt ttgcgggcat cattttctac   1320
tggccaaaaa tgtttggttg gaagctcaat gaagcttggg gtaaagcagc attctggttc   1380
tggttctttg gttctatttt tgcattcatg ccattgtata cctcggtttt catgggtatg   1440
acacgtcgtt tgaatacata tgacaaccct gaatgggatc cgtatttggc tattgcactt   1500
tttggtgcgg tgttagttgc aattggtatt gcatgtttct taatgcaaat cattgttggc   1560 ttccttacaac gtcatcaaaa tatggaccat actggcgacc catgggatag ccgtacttta   1620
gaatggtcta cttcttctcc tgctccattt tataactttg cacatgttcc aaatggtaac   1680
ggtgtagatg cattctgggt agacaaagag aatggtatag cctacgcacg taataccaaa   1740
tatgaagata ttcatatgcc aactgaccgt gctgctggtt tgtaattgc gatgttcatt   1800 acaacaatgg gctttgcttt aatctggcat atctggtggc tcgttgcagt tgtttcatt   1860 gcttcaattg taagcttgat ccgtagttca ttcacaaaag aagtggatta ctatgtacca   1920
gcagcagaag ttgagcgcat tgaaaatgaa cgctatgcgt tacttgaaaa acacttgaag   1980
aaggactaa                                                           1989
```

<210> SEQ ID NO 10
<211> LENGTH: 1146
<212> TYPE: DNA
<213> ORGANISM: Acinetobacter baylyi

<400> SEQUENCE: 10

```
atgatcgaat atgaactcct aaaaattatc tggtgggtct tggtaggcgt actattgatt     60
ggttttgcat tgactgatgg ttttgatatg ggctctatgg caattatgcc atttgttgga    120
aaaaccgatt cagaacgtcg tgcagcaatc aatactatcg cacctcactg ggatggaaac    180
caggtgtggt ttattacagc aggcggtgct ttatttgccg cttggccaat ggtctatgct    240
gttgcttttt caggtttata ctgggcgtta ttattggtcc tattcgcgct gtttcttcga    300
ccagtgggtt ttgactatcg ttcaaaactg gaaaatactc agtggcgcaa ttcttgggac    360
tgggctctga gtattggagg agctgttcct gcacttgtgt ttggtgtcgc gtttggaaat    420 ctattttag gtgttcccct tcacttgac gataccttac gttccgaata tacaggtagt    480
ttctttgctt tactcaatcc atttgccctta ctgtgtggca ttgtgagtct gtcaatgcta    540
tgcgcgcatg gcggtgcatg gttgatgctt cgtacagatg gtgtactcaa caacgttct    600 gccaaagcga ctcagattat gggaattgta ttcctgatct gctttatcgc agctggcgcg    660
```

```
tggttgtatt ttgctcaagt accaggttat agctatgcag ttcctatcga tccaaatgct    720
gctttgaatc cattggcaaa aaagttgtg accaacgcca atgctggctg gatgaataac     780
tatcatcttt atcctgtgag tatgctggcg ccgattgttg caattattgg ggctttagtc    840
ctcattgtag gtgcatcaaa atcgaaagct ggtcttagct ttacaggaac gagtcttgca    900
attattggag caatcttgac cgcaggtttt gctttattcc ccttcctgct tccttcaagt    960
attaatccag tttcaagctt aaccatgtgg gatgccgttt caagccatcg tacacttgga    1020
gtgatgactg ttgcagcctg cattttgta ccgcttattc taatttatac ctcttggtct    1080
tattacaaga tgtggggtgt aattaccaac aagcacatcg aagcaaattc gcatagtttg    1140
tattaa                                                               1146
```

<210> SEQ ID NO 11
<211> LENGTH: 1071
<212> TYPE: DNA
<213> ORGANISM: Acinetobacter baylyi

<400> SEQUENCE: 11

```
ttgactgcat ttgttcaaac cattcaggaa gttttagaaa aaggtcatgg gcctgctgca    60
cgtgctttgg ataagcttcc ttccttcgta caagagtcta ttgcgaaagt tttaggttat    120
ccctatcagt acccgcagtt agatagcttt atcaaatgct tgatggcagt tcaaatcaag    180
caaggtcaaa ctgggtttat cggctcagat gtcgaaaaat cacgtttagc cttttgaaact    240 cagatggagt ccattcttcg caagcccaca gccatacgt ttgtcgaaga tatccgctta    300
ccattacaaa gcggaactat cttttgcacgt cattatcatc ctgctccaaa caaaaaatta   360
cctatgattg tgttctatca tggtgggaga tttgtggtgg gcaatgttga tacacatgat    420
gaagcttgtc gactcattgc aaaatacgcc aatgctcaag tattaagtat cgattatcca    480
ttggcaccag aagtttcacc gcaacgacta attcagtctt gtgaagatgc cttagcttgg    540
gtttatcaaa acaaacgtca ttttaaaata ctaaaaaatc agattgccgt ggcaggtgat    600
agtgcgggtg aaatatcag caccgttgtg gctcagcgtg cgattggaaa agtttacgca    660
ccagatgcac aattcctgat ttatccagta gttgatttta aaagccgtca tccctcattt    720
tatgcatata aagatggatt ggtgctgact ggaaatgacg tcgactatgt gactgattac    780
tatgcaacaa agcatgctgt acatttagat gatccaatta tttcgcctac ctatggtaat    840
ttcaaaaaac tggcgcctgc atatattgtg acggctggac atgatgtatt acatgatgaa    900
ggcgaaatct atagccataa gctacgtcaa gcagggtta aaattcattt tgaagagtac    960
cttgatcaaa cccatggatt tatcaatttg acgccagttt cacataaggc gagagcaaat    1020
ctgattcaga tgagtaaatc attccgtaaa ttttggaata aatacgcctg a              1071
```

<210> SEQ ID NO 12
<211> LENGTH: 885
<212> TYPE: DNA
<213> ORGANISM: Acinetobacter baylyi

<400> SEQUENCE: 12

```
atgctcaata atccacaatt ttatgtcgag caattgaaca aacagattga acgtgtcaaa    60
gagcaatata aatcatttcg tttctatgat ctgggaagtt atgcactcaa ccgtttaacc    120
cctagaacta gttttgaatt ggttgaaaat attgcctatg gtctcaaatc tcggcagcgg    180
ctggatttat atcgtgcaaa aaaaccctta gcccatcggc ctctaattgt ttttgttcat    240
```

```
ggtggggcat ggcagcatgg cgataaaaaa gactatgttt ttattggcga aagcttagca      300
cgagcgggtt atgatgttgc agtcatcaac tatcatctag cgccacaatc gattttccca     360
gtgtatatcg atgatattgc gcaggcactc aactatctga atcaacatca acagcgttta     420
aatatctcta cgcaacatat cattttaatg ggacactcat caggcgcatt taatgtgatg     480
tcggttgttt accatccaca acagcaagct atacattgtc gagatcagat caaagccatt     540
gttggatttg ctggtccgta tcattttgat tataaagggg atcccttagc gcaagatgcg     600
tttgaccaga gtgtgcccta tcaagaggta atgccttttt attttgtgga aacaaactca     660
atcaaacatt atcttttttt ggccgaaaat gatcaaatcg tgaaaaaaag taatactttt     720
gatatgcacc aaaaactatt acaggctggt aaccacagtc atgttgcagt aattgcaaaa     780
acaggtcatg tgaccattat tgcgacatta tcaagcctgt ttagtcagta tttaagact     840 aaacgtacat tattaaactt attaaaagaa acgcacccag cgtaa                     885
```

<210> SEQ ID NO 13
<211> LENGTH: 972
<212> TYPE: DNA
<213> ORGANISM: Acinetobacter baylyi

<400> SEQUENCE: 13

```
atgaaacgga ttttcgccaa tctttatta  agttgtagtc tactgttacc cattacaaca     60
acaatcatct acagccctgc gatatcagca gcttcaggca ttgatattca aaatgtatta    120
cagcaagaac gagcatgggc aggcttacaa accaaacacc ttaaagtagg tgatattgaa    180
tgggtttaca gcgaaagtgg caattcaagc aagcccacga ttatcttaat tcatggttta    240
gcgggaagtc gtgataactg gaatcgggtg gcatacaatt taacacctta ctatcatgtc    300
attattccag atttacctgc acatggtgat accaaaatcc caatgatttt tgacctctct    360
attcctaatt taactgagaa attacgccgt tttgcagaag caggacattt tgaaaaaaat    420
gtacatatcg caggtcattc tatgggcggc gcaattgcac tgctttatac agctcaatat    480
ccgctcgaaa ccaaatcgtt attgcttgtc gatagcgcgg gtgtatttaa aaccgccaat    540
acaccttact aaaagatcc caatttactc aacaatctgg tcgttaaaaa aacaggagat    600
tttgataaac ttttttaagct agcgacagcc tctcccccct ttattccagt tgagctaaaa    660
acagaacaag aaaaactcat gattgctcaa tctaaaaata cccaaaaaat ggtagatcaa    720
ctggtcgcta tgtctaaaat atatacacca gatacctttg caatcgcaac taagtctatt    780
gatgtaccta cttatattat atggggtgat caagataaaa ttattaatgt agaagcggct    840
caagaattaa aaagtttatt aaaaaatgct gaaacgcctt atattttaaa gggtgttggc    900
catatgccta ttctggaagc cgatcaactt gtttcacagc aatatctcat tttttaaat     960 aaacaacctt ag                                                          972
```

<210> SEQ ID NO 14
<211> LENGTH: 1680
<212> TYPE: DNA
<213> ORGANISM: Acinetobacter baylyi

<400> SEQUENCE: 14

```
atggaaaaaa tttggtttgc tgaataccag aaaacaggaa ttccggaaac agtagaatta      60
ccaccagaga atacatcgct cgttgatatc tttgagcgta atttcaaaa atttggctca    120 cgtgatgcat ttatctttat ggataaagca ttgacctta atgagcttga agaagcgagc    180
cgtaaatttg ctgcctattt acaaagtctg aatttaccga aaggtagccg cgttgcagtc    240
```

```
atgatgccga atgtattgca gtatcctatt gtggcattag gcgtctttag agcgggtttg      300
gttctggtta atgtcaaccc attatatacc gcgcgtgaac tcgaacatca gttaaatgat      360
tctggtgcag aagtgctggt gatcattgaa aactttgcga gtgtttacca aacaattttg      420
ggtaaaacac ctgttaagca tgtggtgatt gcctcagtcg gcgatatgct cgggacactt      480
aagggtacac tggttaattt tgtattacgt aaagtgcgta agcagattcc agcgtggaat      540
gtgccaggtc atgtaaagtt taattctgct ttaaataagg taagtccatc tcattacaag      600
cgaccaaatc tcactttaag tgataccgct gtgcttcagt atacgggtgg cacgacaggc      660
gtatcgaaag gggctgagct gacacatcgt aatcttgtgg caaatatgct gcaatgtgat      720
ggaatcttcc agagcaagtt tggatcaggt gacagttcta aagacgataa aatgttctgt      780
gccttaccgc tttatcatat ctttgccttt atggtatgtg ccatgtatgg catgtacaaa      840
ggtcaagcca atattctgat tccaaatcca cgtgatttac ctgctgtgat taggaatta       900
cgtaagtatc aaccgacgtt ctttcctgcc gtaaatacct tgtttaatgc attggttcat      960
aacgaagaat ttaagcaact tgaccatagc aaattgaaaa ttgcgatggg cggtggtatg     1020
gcggtacttc cttctaccgc agaagcatgg aaacgaatta caggcgttac cattattgaa     1080
ggctatggct tgtcagaaac ctcacctgtg caacggtaa atcccctgc gtcgagtgaa      1140
tttagtggca caattggtat tccattacca ttaactgatg tcgcgattct ggatgatgat     1200
ggtcatccag ttgcactcgg agaacagggt gagatctcga ttcgtgggcc tcaagtcatg     1260
aaaggatact ggaatcgtcc agatgaaacg gcgaaggtta tgaccagtga tggtttcttc     1320
cgtacaggtg acattggcgt gatgaatgat cgcggctacg tcaaaattgt agatcgtaaa     1380
aaagatatga ttttggtgtc gggcttcaat gtttatccaa gtgaaattga agaagtgatt     1440
gcaaaacatc cgaaagtact ggaagtcgct gcaattggcg tacctgatga aaaatctggt     1500
gaagtaccca actgtttat tgtgaaaaaa gatccatcac tcacaaccga agaagtttta     1560
agctttgcca aagagaattt gacaggttac aaacgtccgc gttatgtcga gtttatggat     1620
gagttaccaa atctaatgt cggtaaaatc ttgcgtaaag acctgcgtaa aaccaattaa     1680
```

<210> SEQ ID NO 15
<211> LENGTH: 303
<212> TYPE: PRT
<213> ORGANISM: Acinetobacter baylyi

<400> SEQUENCE: 15

Leu Ile Ser Ile Arg Glu Lys Arg Val Asn Lys Leu Glu Ala Leu
1               5                   10                  15

Phe Arg Glu Asn Val Lys Gly Lys Val Ala Leu Ile Thr Gly Ala Ser
                20                  25                  30

Ser Gly Ile Gly Leu Thr Ile Ala Lys Arg Ile Ala Ala Gly Ala
        35                  40                  45

His Val Leu Leu Val Ala Arg Thr Gln Glu Thr Leu Glu Glu Val Lys
    50                  55                  60

Ala Ala Ile Glu Gln Gln Gly Gly Gln Ala Ser Ile Phe Pro Cys Asp
65                  70                  75                  80

Leu Thr Asp Met Asn Ala Ile Asp Gln Leu Ser Gln Gln Ile Met Ala
                85                  90                  95

Ser Val Asp His Val Asp Phe Leu Ile Asn Asn Ala Gly Arg Ser Ile
                100                 105                 110

Arg Arg Ala Val His Glu Ser Phe Asp Arg Phe His Asp Phe Glu Arg

```
                 115                 120                 125
Thr Met Gln Leu Asn Tyr Phe Gly Ala Val Arg Leu Val Leu Asn Leu
    130                 135                 140

Leu Pro His Met Ile Lys Arg Lys Asn Gly Gln Ile Ile Asn Ile Ser
145                 150                 155                 160

Ser Ile Gly Val Leu Ala Asn Ala Thr Arg Phe Ser Ala Tyr Val Ala
                165                 170                 175

Ser Lys Ala Ala Leu Asp Ala Phe Ser Arg Cys Leu Ser Ala Glu Val
            180                 185                 190

Leu Lys His Lys Ile Ser Ile Thr Ser Ile Tyr Met Pro Leu Val Arg
        195                 200                 205

Thr Pro Met Ile Ala Pro Thr Lys Ile Tyr Lys Tyr Val Pro Thr Leu
    210                 215                 220

Ser Pro Glu Glu Ala Ala Asp Leu Ile Val Tyr Ala Ile Val Lys Arg
225                 230                 235                 240

Pro Lys Arg Ile Ala Thr His Leu Gly Arg Leu Ala Ser Ile Thr Tyr
                245                 250                 255

Ala Ile Ala Pro Asp Ile Asn Asn Ile Leu Met Ser Ile Gly Phe Asn
            260                 265                 270

Leu Phe Pro Ser Ser Thr Ala Ala Leu Gly Glu Gln Glu Lys Leu Asn
        275                 280                 285

Leu Leu Gln Arg Ala Tyr Ala Arg Leu Phe Pro Gly Glu His Trp
    290                 295                 300

<210> SEQ ID NO 16
<211> LENGTH: 322
<212> TYPE: PRT
<213> ORGANISM: Acinetobacter baylyi

<400> SEQUENCE: 16

Met Lys Phe Lys Leu Leu Phe Thr Thr Leu Leu Val Leu Thr Gln
1               5                   10                  15

Pro Val Phe Ala Thr Ser Pro Ile Gln Asn Pro Thr Thr Ser Phe Val
                20                  25                  30

Ile Ser Asp Tyr Ala Lys Thr Lys Tyr Pro Ile Val Leu Ser His Gly
            35                  40                  45

Leu Phe Gly Phe Asn Lys Leu Gly Thr Glu Ala Phe Gly Leu Asp Tyr
        50                  55                  60

Trp Tyr Gln Ile Pro Gln Asp Leu Ala Arg Asn Gly Ala Asn Val Trp
65                  70                  75                  80

Val Thr Arg Gln Ser Thr Ala Asn Thr Ser Glu Phe Arg Gly Glu Gln
                85                  90                  95

Leu Leu Ala Glu Val Gln Asp Ile Leu Ala Ile Thr Gly Ala Gln Lys
            100                 105                 110

Val Asn Leu Ile Gly His Ser His Gly Ser Gln Thr Val Arg Tyr Val
        115                 120                 125

Ala Gly Val Leu Pro Ala Asn Ile Ala Ser Val Ser Thr Ile Gly Gly
    130                 135                 140

Pro Ala Lys Gly Ala Pro Leu Ala Asp Leu Ile Tyr Lys Thr Leu Ala
145                 150                 155                 160

Gly Thr Pro Leu Glu Ala Pro Ile Ala Thr Ile Phe Asn Val Ala Met
                165                 170                 175

Asn Phe Ile Thr Ile Gly Gln Phe Asp Asp Pro Gln Lys Tyr Pro Met
            180                 185                 190
```

```
Asn Ser Val Gly Ala Ala Tyr Ser Leu Ser Thr Glu Gly Ala Gly Lys
            195                 200                 205

Phe Asn Ala Ile Phe Pro Ala Gly Val Pro Thr Thr Ala Cys Gly Gln
    210                 215                 220

Gly Glu Ser Ser Val Asn Gly Val Arg Tyr Tyr Ser Trp Ser Gly Ala
225                 230                 235                 240

Ser Pro Leu Thr Asn Pro Leu Asp Pro Ser Asp Tyr Gly Leu Ser Leu
                245                 250                 255

Thr Ser Val Phe Ser Gly Lys Asn Asn Asp Gly Leu Val Pro Ser Cys
            260                 265                 270

Ser Ser His Leu Gly Thr Val Ile Arg Asp Asn Tyr Val Trp Asn His
        275                 280                 285

Leu Asp Glu Val Asn Gln Ile Leu Gly Leu Arg Ser Ile Phe Ala Gln
    290                 295                 300

Asp Pro Val Ser Ile Phe Arg Gln His Ala Asn Arg Leu Lys Gly Gln
305                 310                 315                 320

Asn Leu

<210> SEQ ID NO 17
<211> LENGTH: 573
<212> TYPE: PRT
<213> ORGANISM: Acinetobacter baylyi

<400> SEQUENCE: 17

Met Ser Asn Gln Lys Val Ser Asp Ile Ile Glu Val Leu Glu Gln
1               5                   10                  15

Ala Gly Val Gln Arg Cys Tyr Gly Ile Val Gly Asp Thr Leu Asn His
            20                  25                  30

Val Thr Asp Ser Met Ser Lys Ser Lys Ile Glu Trp Ile His Val Arg
        35                  40                  45

His Glu Glu Val Gly Gly Phe Ala Ala Gly Thr Asp Ala Leu Leu Ser
    50                  55                  60

Gly His Leu Thr Ala Cys Ala Gly Ser Cys Gly Pro Gly Ser Leu His
65                  70                  75                  80

Phe Ile Asn Gly Leu Tyr Glu Ser His Arg Asn Arg Ala Pro Val Ile
                85                  90                  95

Leu Ile Ala Ser Gln Ile Ser Thr Glu Met Ala Gly Phe Ile Asp Phe
            100                 105                 110

Pro Gln Tyr Val Asp Phe Lys Ser Val Tyr Ala Lys Asn Ser Val Phe
        115                 120                 125

Cys Glu Glu Ile Thr Gln Pro Ser Gln Ala Arg His Ile Met Ser Met
    130                 135                 140

Ala Cys Gln Ala Ala Leu Asn Lys Arg Gly Val Ala Val Ile Val
145                 150                 155                 160

Pro Ala Asn Ile Ser Glu Ala Ser Ala Glu Ala Gly Leu Pro Phe Val
                165                 170                 175

Pro Arg His Val Glu Pro Asp Ile Leu Pro Asn Lys Ala Glu Leu His
            180                 185                 190

Gln Met Val Glu Leu Ile Ser Gln His Gln Lys Ile Gly Ile Tyr Ala
        195                 200                 205

Gly Ala Gly Cys Glu Gly Ala His Asp Gln Leu Ile Ala Phe Ala Glu
    210                 215                 220

Lys Leu Lys Ala Pro Val Ala His Thr Ser Arg Ala Lys Asp Phe Val
225                 230                 235                 240
```

-continued

```
Glu Tyr Asp Asn Pro Tyr Asn Met Gly Met Thr Gly Ile Phe Gly Asn
                245                 250                 255

Lys Ala Gly Tyr His Thr Leu Met Asp Cys Asp Leu Leu Ile Leu Leu
            260                 265                 270

Gly Ala Asp Phe Ala Trp Ala Gln Tyr Tyr Pro Ser His Ala Lys Ile
        275                 280                 285

Leu Gln Ile Asp Ile Asp Pro Thr His Leu Gly Arg Arg His Pro Ile
    290                 295                 300

Thr Leu Gly Ala Val Gly Lys Ile Ser Ser Thr Leu Asp Ala Leu Leu
305                 310                 315                 320

Pro Leu Leu Glu Thr Arg Gln Glu Arg Ala Phe Leu Asp His Cys Leu
                325                 330                 335

Glu Leu Lys His His Ser Asp Glu Thr Arg His Lys Glu Glu Arg Val
            340                 345                 350

Gly Lys Asp Gly Leu Ile His Pro Gln Tyr Leu Val Ser Leu Leu Asn
        355                 360                 365

Arg Tyr Ala Asp Gln Asp Ala Ile Phe Phe Gly Asp Gly Gly Ser Pro
    370                 375                 380

Met Val Trp Val Leu Arg His Ile Asp Val Asn Gly Lys Arg Arg Thr
385                 390                 395                 400

Phe Thr Ser Leu Leu His Gly Thr Met Ala Asn Ala Met Pro Gln Ala
                405                 410                 415

Leu Gly Ala Gln Lys Ala Phe Pro Asn Arg Gln Ile Ile Ala Leu Cys
            420                 425                 430

Gly Asp Gly Gly Leu Ala Met Leu Leu Gly Asp Leu Leu Thr Thr Ile
        435                 440                 445

Gln Glu Lys Leu Pro Ile Lys Ile Val Val Phe Asn Asn Ser Ser Leu
    450                 455                 460

Asn Phe Val Glu Leu Glu Gln Lys Val Glu Gly Leu Leu Asp His Tyr
465                 470                 475                 480

Thr Asp Leu Leu Asn Pro Asp Phe Gly Lys Leu Ala Ser Val Ile Gly
                485                 490                 495

Leu His Gly Gln Thr Val Thr His Gly Asp Gly Leu Glu Gln Ala Val
            500                 505                 510

Glu Asn Phe Leu Lys His Asp Gly Pro Ala Leu Leu Asn Val His Thr
        515                 520                 525

Asn Pro Met Glu Leu Val Met Pro Pro Asp Pro Asn Leu Asn Gln Val
    530                 535                 540

Ser Ser Thr Ser Leu Tyr Ala Ile Lys Ala Leu Met Ser Gly Arg Val
545                 550                 555                 560

Asp Asp Val Lys Asn Leu Leu Val Asn Asn Phe Ile Lys
                565                 570
```

<210> SEQ ID NO 18
<211> LENGTH: 213
<212> TYPE: PRT
<213> ORGANISM: Acinetobacter baylyi

<400> SEQUENCE: 18

```
Met Asp Gln Ile Arg Pro Phe Pro Gln Thr Asp Phe Ile Asp Gln Ala
1               5                   10                  15

Glu Glu Glu Glu Ala Ile Arg Leu Ile Ala Ala Pro Asp Leu Lys Glu
            20                  25                  30

Trp Val Ile Thr Asn Phe Leu Thr Leu Gly Gly Glu Leu His Asn Pro
        35                  40                  45
```

```
Asp His Asp His Ile Ala Glu Leu Leu His Asp Asp Glu Thr Phe Leu
 50                  55                  60

Ala Phe Ala Trp Ala Ser Ser Ala Phe Thr Arg Ala Lys Arg Met Val
 65                  70                  75                  80

Leu Gly Gln Cys Glu Lys Val Met Phe Asn Gln Gly Gly Trp Lys Lys
                 85                  90                  95

Ala Arg Gln Glu Gln Gln Met Arg Asp Trp Phe Gly Phe Val Pro Val
                100                 105                 110

Tyr Leu Ile Thr Ile Asp Ala Ser Phe Cys Glu Gln Ala Thr Asp Arg
            115                 120                 125

Glu Phe Cys Ala Leu Ile Glu His Glu Leu Tyr His Ile Gly Val Glu
            130                 135                 140

Arg Asp Gly Asp Gly Glu Ile Val Tyr Ser Asp His Thr Gly Leu Pro
145                 150                 155                 160

Lys His Tyr Leu Ala Gly His Asp Val Glu Glu Phe Val Gly Val Val
                165                 170                 175

Lys Arg Trp Gly Ala Ser Asp Asp Ile Lys Arg Leu Val Glu Val Ala
                180                 185                 190

Lys Gln Ala Pro Phe Val Ser Glu Lys Asn Ile Ala Ala Ser Cys Gly
                195                 200                 205

Thr Cys Leu Ile Lys
    210

<210> SEQ ID NO 19
<211> LENGTH: 131
<212> TYPE: PRT
<213> ORGANISM: Acinetobacter baylyi

<400> SEQUENCE: 19

Met Phe Cys Glu Ile Val Met Asn Gln Ser Ser Pro Tyr Lys Gly Lys
 1               5                  10                  15

Gln Gly Leu Lys Arg Ile Ile Asn Ala Thr Gly Tyr Ser Ile Ser Gly
                20                  25                  30

Phe Lys Ile Ala Phe Lys Gln Glu Ala Ala Phe Arg Gln Ile Ile Phe
            35                  40                  45

Leu Asn Leu Ile Leu Leu Pro Ile Asn Leu Ser Leu Ser Leu Arg Pro
 50                  55                  60

Ser Glu His Ala Ile Leu Phe Ala Val Gly Leu Ile Ala Val Ile Val
 65                  70                  75                  80

Glu Leu Phe Asn Ser Ala Ile Glu Ala Ala Ile Asp Arg Ile Ser Leu
                 85                  90                  95

Asp Arg His Glu Leu Ser Lys Asn Ala Lys Asp Met Gly Ser Ala Ala
                100                 105                 110

Gln Cys Val Ala Leu Ile Met Ile Ala Leu Thr Trp Thr Ile Ile Leu
            115                 120                 125

Phe Trp Ala
    130

<210> SEQ ID NO 20
<211> LENGTH: 632
<212> TYPE: PRT
<213> ORGANISM: Acinetobacter baylyi

<400> SEQUENCE: 20

Met Gly Ala Ile Asn Pro Lys Glu Asp Tyr Ser Asn Ile Gln Asn Leu
 1               5                  10                  15
```

-continued

```
Thr Phe Asp Ala Val Ile Val Gly Gly Gly Ser Gly Met Arg Ala
             20                  25                  30

Ser Tyr Gln Leu Ala Gln Ala Gly Leu Lys Val Ala Val Leu Thr Lys
         35                  40                  45

Val Phe Pro Thr Arg Ser His Thr Val Ala Ala Gln Gly Gly Ile Gly
 50                  55                  60

Ala Ser Leu Gly Asn Met Gln Glu Asp Asn Trp His Phe His Phe Tyr
 65                  70                  75                  80

Asp Thr Val Lys Gly Ser Asp Trp Leu Gly Asp Gln Asp Ala Ile Glu
                 85                  90                  95

Phe Met Thr Arg Glu Ala Pro Lys Val Val Tyr Glu Leu Glu His Leu
             100                 105                 110

Gly Met Pro Phe Asp Arg Asn Ala Asp Gly Thr Ile Tyr Gln Arg Pro
             115                 120                 125

Phe Gly Gly His Ser Ala Asn Tyr Gly Asp Lys Pro Val Pro Arg Ala
         130                 135                 140

Cys Ala Ala Ala Asp Arg Thr Gly His Ala Leu Leu His Thr Leu Tyr
145                 150                 155                 160

Gln Ser Asn Val Lys Met Gly Thr Gln Phe Phe Val Glu Trp Ile Ala
                 165                 170                 175

Leu Asp Leu Ile Arg Asn Glu Ala Gly Asp Val Leu Gly Val Thr Ala
             180                 185                 190

Tyr Asp Gln Glu Thr Gly Asn Ile Ala Val Phe Gln Ala Lys Ala Thr
         195                 200                 205

Leu Phe Ala Thr Gly Gly Ala Gly Arg Val Tyr Arg Ala Ser Thr Asn
210                 215                 220

Ala Tyr Ile Asn Thr Gly Asp Gly Leu Gly Met Ala Ala Arg Ala Gly
225                 230                 235                 240

Ile Pro Leu Gln Asp Met Glu Phe Trp Gln Phe His Pro Thr Gly Val
                 245                 250                 255

Ala Gly Ala Gly Val Leu Leu Thr Glu Gly Cys Arg Gly Glu Gly Ala
             260                 265                 270

Ile Leu Arg Asn Lys Asp Gly Glu Pro Phe Met Glu Arg Tyr Ala Pro
         275                 280                 285

Thr Leu Lys Asp Leu Ala Pro Arg Asp Phe Val Ser Arg Ser Met Asp
290                 295                 300

Gln Glu Ile Lys Glu Gly Arg Gly Cys Gly Pro Lys Ala Asp Tyr Ile
305                 310                 315                 320

Leu Leu Asp Met Thr His Leu Gly Ala Asp Thr Ile Met Lys Arg Leu
                 325                 330                 335

Pro Ser Val Phe Glu Ile Gly Lys Lys Phe Ala Asn Val Asp Ile Thr
             340                 345                 350

Lys Glu Pro Ile Pro Val Val Pro Thr Ile His Tyr Gln Met Gly Gly
         355                 360                 365

Ile Pro Thr Asn Ile His Gly Gln Val Val Pro Val Ala Thr Glu
370                 375                 380

Asn Leu His Leu Glu Ala His Tyr Asn Asn Ala Thr Lys Glu Tyr Thr
385                 390                 395                 400

Phe Glu Thr Asn Cys Pro Asp Phe Val Lys Pro Val Lys Gly Phe Tyr
                 405                 410                 415

Ala Ile Gly Glu Cys Ser Cys Val Ser Val His Gly Ala Asn Arg Leu
             420                 425                 430
```

Gly Thr Asn Ser Leu Leu Asp Leu Val Val Phe Gly Lys Ala Ala Gly
            435                 440                 445

Glu His Ile Ile Asp Tyr Val Thr Lys His His Gly Asp Glu Tyr Ala
    450                 455                 460

Pro Leu Pro Thr Asp Val Leu Glu Ser Thr Leu Lys Arg Ile Arg His
465                 470                 475                 480

Leu Asp Glu Ser Thr Ser Gly Glu Asn Ala Gln Glu Val Ala Asp Ala
                485                 490                 495

Ile Arg Asp Ile Val Gln Asp His Ala Ala Val Phe Arg Thr Gln Glu
            500                 505                 510

Leu Leu Asp Glu Gly Val Arg Gln Ile Leu Ala Leu Glu Pro Arg Val
        515                 520                 525

Arg Asn Ile Tyr Leu Lys Asp Lys Ser Lys Val Phe Asn Thr Ala Arg
    530                 535                 540

Val Glu Ala Leu Glu Val Glu Asn Leu Tyr Glu Val Ala Lys Ala Thr
545                 550                 555                 560

Leu Ile Ser Ala Ala Ala Arg Lys Glu Cys Arg Gly Ala His Thr Val
                565                 570                 575

Val Asp Tyr Glu Leu Ala Pro Asp His Pro Asp Tyr Pro Tyr Gly Arg
            580                 585                 590

Arg Asp Asp Glu Trp Met Lys His Thr Leu Trp Tyr Ser Ala Asp Asn
        595                 600                 605

Arg Leu Glu Tyr Lys Pro Val Arg Tyr Val Pro Leu Thr Val Asp Ala
    610                 615                 620

Ile Pro Pro Ala Pro Arg Thr Phe
625                 630

<210> SEQ ID NO 21
<211> LENGTH: 507
<212> TYPE: PRT
<213> ORGANISM: Acinetobacter baylyi

<400> SEQUENCE: 21

Met Val Met Thr Thr Ser Ala Ser Leu Pro Leu Tyr Asp Ile Val Val
1               5                   10                  15

Val Gly Gly Gly Ile Asn Gly Ile Gly Ile Ala Asn Asp Ala Ala Gly
            20                  25                  30

Arg Gly Leu Ser Val Phe Leu Cys Glu Lys Asp Asp Phe Ala Ser His
        35                  40                  45

Thr Ser Ser Ala Ser Ser Lys Leu Ile His Gly Gly Leu Arg Tyr Leu
    50                  55                  60

Glu His Tyr Glu Phe Arg Leu Val Arg Glu Ala Leu Ala Glu Arg Glu
65                  70                  75                  80

Val Leu Met Ala Lys Ala Pro His Leu Val Arg Pro Leu Arg Phe Ile
                85                  90                  95

Leu Pro Tyr Gln Ala His Leu Arg Ser Glu Trp Leu Ile Arg Ser Gly
            100                 105                 110

Leu Phe Leu Tyr Asp His Leu Gly Lys Arg Lys Lys Leu Thr Ala Ser
        115                 120                 125

Lys Lys Ile Thr Phe Asp Ser Ala Ser Pro Leu Lys Ser Glu Ile Ser
    130                 135                 140

Lys Gly Phe Glu Tyr Ala Asp Cys Thr Val Asp Asp Ala Arg Leu Val
145                 150                 155                 160

Ile Ile Asn Ala Ile Gln Ala Arg Glu Lys Gly Ala Glu Leu Val Thr
                165                 170                 175

His Thr Glu Cys Leu Ser Ala Glu Ile Val Asp Asp Val Trp Leu Ile
            180                 185                 190

Thr Leu Gln His Arg Gln Val Pro Tyr Gln Ile Arg Ala Lys Val Leu
            195                 200                 205

Ile Asn Ala Thr Gly Pro Trp Val Glu Ser Phe Leu Lys Ser Gln Leu
210                 215                 220

Lys Gln His Ser Pro Tyr Lys Ile Arg His Ile Gln Gly Ser His Leu
225                 230                 235                 240

Ile Val Ala Lys Leu Tyr Glu Asp Asn His Ala Tyr Ile Leu Gln Asn
            245                 250                 255

Glu Asp Gly Arg Ile Val Phe Val Ile Pro Tyr Leu Asn Asp Phe Ser
            260                 265                 270

Leu Ile Gly Thr Thr Asp Gln Val Tyr Leu Asp Asp Leu Asn Leu Val
            275                 280                 285

Asn Ile Thr Gln Gln Glu Ile Ser Tyr Leu Leu Asp Val Val Asn Arg
290                 295                 300

His Phe Lys Thr Val Leu Thr Arg Ala Asp Ile Ile Gln Thr Tyr Ser
305                 310                 315                 320

Gly Val Arg Pro Leu Cys Asp Asp Glu Ser Asp Gln Pro Ser Ala Ile
            325                 330                 335

Thr Arg Asp Tyr Thr Leu Ala Leu Thr Met Val Ser Glu Val Ala Pro
            340                 345                 350

Leu Leu Ser Val Phe Gly Gly Lys Leu Thr Thr Tyr Arg Lys Leu Ala
            355                 360                 365

Gly Ser Ala Leu Glu Gln Leu Lys Leu Phe Phe Pro Asp Met Thr Pro
            370                 375                 380

Ser Trp Thr Glu Tyr Glu Pro Leu Pro Gly Gly Glu Tyr Phe Lys Gly
385                 390                 395                 400

Gln Asp Lys Leu Val Asn Ala Ile Gln Leu Arg Ile Lys Gly Ile Ala
            405                 410                 415

Ser Glu Leu Ala Lys Arg Trp Ala Thr Ser Tyr Gly Thr Arg Val Trp
            420                 425                 430

Lys Leu Leu Gln Gly Val Tyr Ser Glu Glu Asp Phe Gly Ile Tyr Phe
            435                 440                 445

Gly His Gly Leu Tyr Gln Leu Glu Val Asp Tyr Leu Val Lys Val Glu
            450                 455                 460

Trp Val Glu Ser Ala Asp Asp Val Leu Trp Arg Arg Thr Lys Leu Gly
465                 470                 475                 480

Phe Arg Phe Asn Gln Asn Glu Ile Leu Val Leu Gln Asp Tyr Leu Ile
            485                 490                 495

Ser Leu Val Val Gly Glu Gln Gly Lys Ile Ala
            500                 505

<210> SEQ ID NO 22
<211> LENGTH: 353
<212> TYPE: PRT
<213> ORGANISM: Acinetobacter baylyi

<400> SEQUENCE: 22

Met Arg Gln Thr Ile Leu Ala Val Leu Ser Leu Ser Thr Ile Ala Ala
1               5                   10                  15

Leu Leu Thr Gly Cys Gly Gly Asp Met Val Leu Leu Asn Ser Lys Gly
            20                  25                  30

Pro Val Gly Gln Gly Gln Ser Asn Leu Met Met Thr Ala Ile Tyr Leu

```
            35                  40                  45
Met Leu Leu Val Val Ile Pro Ser Val Ile Met Ala Leu Trp Phe Ser
 50                  55                  60

Trp Lys Tyr Arg Ala Ser Asn Lys Asp Ala Asp Tyr Lys Pro Thr Trp
 65                  70                  75                  80

Ala His Ser Thr Ala Ile Glu Ile Val Trp Gly Val Pro Val Ile
                 85                  90                  95

Ile Ile Gly Ile Leu Ala Trp Leu Thr Trp Trp Gly Ser His Lys Tyr
                100                 105                 110

Asp Pro Tyr Arg Pro Leu Glu Ser Asp Lys Ala Pro Leu Thr Ile Gln
                115                 120                 125

Val Ile Ala Glu Gln Phe Lys Trp Ile Phe Val Tyr Pro Glu Gln Asn
130                 135                 140

Ile Ala Thr Val Asn Glu Val Arg Phe Pro Lys Thr Pro Leu Ser
145                 150                 155                 160

Phe Lys Ile Thr Ser Asn Phe Thr Met Asn Ser Phe Ile Pro Gln
                165                 170                 175

Leu Gly Gly Gln Ile Tyr Ala Met Ala Gly Met Gln Thr His Leu His
                180                 185                 190

Leu Met Ala Asp Gln Pro Gly Val Phe Arg Gly Met Ser Ser Asn Tyr
                195                 200                 205

Ser Gly Tyr Gly Phe Ser Gln Met His Phe Lys Ala Tyr Ser Val Thr
210                 215                 220

Glu Ala Glu Phe Thr Gln Trp Val Asp Ala Val Lys Ala Gly Lys Gly
225                 230                 235                 240

Thr Gly Val Asn Pro Glu Ala Ile Gln Lys Gly Ile Leu Asp Gln Ala
                245                 250                 255

Glu Leu Ala Thr Leu Lys Asp Gly Asp Arg Ser Lys His Gln Ile Glu
                260                 265                 270

Ala Leu Val His Arg Ala Gln Ala Ala Gly Asp Ala Glu Ala Leu Ala
                275                 280                 285

Lys Ala Glu Ala Met Lys Pro Phe Pro Asn Lys Pro His Pro Val Thr
290                 295                 300

Tyr Tyr Ser Ser Val Glu Pro Lys Leu Phe Glu Thr Val Ile Asn Arg
305                 310                 315                 320

Tyr Met Ser Asn Tyr His Gly Asp His Ser Ala Thr Ala Glu His
                325                 330                 335

Gly Ser Gln Ala His Ala Ala Asn Ala His Ala Thr Ala Ser Val Glu
                340                 345                 350

Glu

<210> SEQ ID NO 23
<211> LENGTH: 662
<212> TYPE: PRT
<213> ORGANISM: Acinetobacter baylyi

<400> SEQUENCE: 23

Met Leu Leu Leu Gly Lys Leu Gly Trp Asp Ser Ile Pro Lys Glu Pro
 1               5                  10                  15

Ile Val Leu Val Thr Met Val Leu Met Ala Ile Gly Ala Ile Ala Val
                20                  25                  30

Leu Gly Gly Ile Thr Tyr Phe Lys Lys Trp Gly Tyr Leu Trp Lys Glu
                35                  40                  45

Trp Phe Ile Thr Val Asp His Lys Lys Ile Gly Ile Met Tyr Ile Leu
```

```
            50                  55                  60
Val Ser Val Val Met Leu Arg Gly Phe Ala Asp Ala Ile Met Met
65                  70                  75                  80

Arg Leu Gln Leu Phe Leu Ala Lys Gly Gly Glu Gly Tyr Leu His
                    85                  90                  95

Pro Asp His Tyr Asp Gln Ile Phe Thr Ala His Gly Val Ile Met Ile
                100                 105                 110

Phe Phe Val Ala Met Gly Leu Val Val Gly Met Met Asn Ile Ser Val
                115                 120                 125

Pro Leu Gln Ile Gly Ala Arg Asp Val Ala Phe Pro Leu Leu Asn Ser
    130                 135                 140

Leu Ser Phe Trp Leu Phe Ala Gly Ala Gly Leu Met Met Ala Ser
145                 150                 155                 160

Leu Val Leu Gly Glu Phe Ala Ala Thr Gly Trp Met Ala Tyr Pro Pro
                165                 170                 175

Leu Ser Gly Ile Gln Tyr Ser Pro Gly Val Gly Val Asp Tyr Tyr Ile
                180                 185                 190

Trp Ala Leu Gln Val Ser Gly Leu Gly Thr Leu Leu Ser Gly Val Asn
            195                 200                 205

Phe Phe Val Thr Ile Ile Lys Met Arg Ala Pro Gly Met Lys Leu Met
210                 215                 220

Asp Met Pro Ile Phe Thr Trp Thr Ser Leu Cys Thr Ala Val Leu Ile
225                 230                 235                 240

Ile Ala Ser Phe Pro Val Leu Thr Ala Thr Leu Ala Met Leu Thr Leu
                245                 250                 255

Asp Arg Tyr Phe Gly Phe His Phe Phe Thr Asn Glu Leu Gly Gly Ser
                260                 265                 270

Pro Met Leu Tyr Val Asn Leu Ile Trp Thr Trp Gly His Pro Glu Val
                275                 280                 285

Tyr Ile Leu Val Leu Pro Ala Phe Gly Leu Tyr Ser Glu Ile Val Ala
    290                 295                 300

Thr Phe Ser Arg Lys Ala Leu Phe Gly Tyr Lys Ser Met Val Tyr Ala
305                 310                 315                 320

Thr Ile Ala Ile Thr Val Leu Ala Phe Val Val Trp Leu His His Phe
                325                 330                 335

Phe Thr Met Gly Ala Gly Ala Asn Val Asn Ala Phe Phe Gly Ile Met
                340                 345                 350

Thr Met Ile Ile Ala Ile Pro Thr Gly Val Lys Ile Phe Ser Trp Leu
                355                 360                 365

Phe Thr Met Tyr Lys Gly Arg Ile Ser Phe Glu Thr Pro Met Leu Trp
    370                 375                 380

Thr Leu Gly Phe Leu Val Thr Phe Gly Ile Gly Gly Leu Thr Gly Val
385                 390                 395                 400

Leu Met Ala Val Pro Pro Ala Asp Phe Leu Val His Asn Ser Leu Phe
                405                 410                 415

Leu Ile Ala His Phe His Asn Val Ile Ile Gly Gly Val Val Phe Gly
                420                 425                 430

Met Phe Ala Gly Ile Ile Phe Tyr Trp Pro Lys Met Phe Gly Trp Lys
                435                 440                 445

Leu Asn Glu Ala Trp Gly Lys Ala Ala Phe Trp Phe Trp Phe Phe Gly
    450                 455                 460

Phe Tyr Phe Ala Phe Met Pro Leu Tyr Ile Leu Gly Phe Met Gly Met
465                 470                 475                 480
```

```
Thr Arg Arg Leu Asn Thr Tyr Asp Asn Pro Glu Trp Asp Pro Tyr Leu
                485                 490                 495

Ala Ile Ala Leu Phe Gly Ala Val Leu Val Ala Ile Gly Ile Ala Cys
            500                 505                 510

Phe Leu Met Gln Ile Ile Val Gly Phe Leu Gln Arg His Gln Asn Met
        515                 520                 525

Asp His Thr Gly Asp Pro Trp Asp Ser Arg Thr Leu Glu Trp Ser Thr
    530                 535                 540

Ser Ser Pro Ala Pro Phe Tyr Asn Phe Ala His Val Pro Asn Gly Asn
545                 550                 555                 560

Gly Val Asp Ala Phe Trp Val Asp Lys Glu Asn Gly Ile Ala Tyr Ala
                565                 570                 575

Arg Asn Thr Lys Tyr Glu Asp Ile His Met Pro Thr Asp Arg Ala Ala
            580                 585                 590

Gly Phe Val Ile Ala Met Phe Ile Thr Thr Met Gly Phe Ala Leu Ile
        595                 600                 605

Trp His Ile Trp Trp Leu Val Ala Val Cys Phe Ile Ala Ser Ile Val
    610                 615                 620

Ser Leu Ile Arg Ser Ser Phe Thr Lys Glu Val Asp Tyr Tyr Val Pro
625                 630                 635                 640

Ala Ala Glu Val Glu Arg Ile Glu Asn Glu Arg Tyr Ala Leu Leu Glu
                645                 650                 655

Lys His Leu Lys Lys Asp
            660

<210> SEQ ID NO 24
<211> LENGTH: 381
<212> TYPE: PRT
<213> ORGANISM: Acinetobacter baylyi

<400> SEQUENCE: 24

Met Ile Glu Tyr Glu Leu Leu Lys Ile Ile Trp Trp Val Leu Val Gly
1               5                   10                  15

Val Leu Leu Ile Gly Phe Ala Leu Thr Asp Gly Phe Asp Met Gly Ser
            20                  25                  30

Met Ala Ile Met Pro Phe Val Gly Lys Thr Asp Ser Glu Arg Arg Ala
        35                  40                  45

Ala Ile Asn Thr Ile Ala Pro His Trp Asp Gly Asn Gln Val Trp Phe
    50                  55                  60

Ile Thr Ala Gly Gly Ala Leu Phe Ala Ala Trp Pro Met Val Tyr Ala
65                  70                  75                  80

Val Ala Phe Ser Gly Leu Tyr Trp Ala Leu Leu Val Leu Phe Ala
                85                  90                  95

Leu Phe Leu Arg Pro Val Gly Phe Asp Tyr Arg Ser Lys Leu Glu Asn
                100                 105                 110

Thr Gln Trp Arg Asn Ser Trp Asp Trp Ala Leu Ser Ile Gly Gly Ala
            115                 120                 125

Val Pro Ala Leu Val Phe Gly Val Ala Phe Gly Asn Leu Phe Leu Gly
        130                 135                 140

Val Pro Phe Ser Leu Asp Asp Thr Leu Arg Ser Glu Tyr Thr Gly Ser
145                 150                 155                 160

Phe Phe Ala Leu Leu Asn Pro Phe Ala Leu Leu Cys Gly Ile Val Ser
                165                 170                 175

Leu Ser Met Leu Cys Ala His Gly Gly Ala Trp Leu Met Leu Arg Thr
```

```
                180                 185                 190
Asp Gly Val Leu Lys Gln Arg Ser Ala Lys Ala Thr Gln Ile Met Gly
            195                 200                 205

Ile Val Phe Leu Ile Cys Phe Ile Ala Ala Gly Ala Trp Leu Tyr Phe
210                 215                 220

Ala Gln Val Pro Gly Tyr Ser Tyr Ala Val Pro Ile Asp Pro Asn Ala
225                 230                 235                 240

Ala Leu Asn Pro Leu Ala Lys Lys Val Val Thr Asn Ala Asn Ala Gly
            245                 250                 255

Trp Met Asn Asn Tyr His Leu Tyr Pro Val Ser Met Leu Ala Pro Ile
                260                 265                 270

Val Ala Ile Ile Gly Ala Leu Val Leu Ile Val Gly Ala Ser Lys Ser
            275                 280                 285

Lys Ala Gly Leu Ser Phe Thr Gly Thr Ser Leu Ala Ile Ile Gly Ala
            290                 295                 300

Ile Leu Thr Ala Gly Phe Ala Leu Phe Pro Phe Leu Leu Pro Ser Ser
305                 310                 315                 320

Ile Asn Pro Val Ser Ser Leu Thr Met Trp Asp Ala Val Ser Ser His
                325                 330                 335

Arg Thr Leu Gly Val Met Thr Val Ala Ala Cys Ile Phe Val Pro Leu
            340                 345                 350

Ile Leu Ile Tyr Thr Ser Trp Ser Tyr Lys Met Trp Gly Val Ile
            355                 360                 365

Thr Asn Lys His Ile Glu Ala Asn Ser His Ser Leu Tyr
370                 375                 380

<210> SEQ ID NO 25
<211> LENGTH: 356
<212> TYPE: PRT
<213> ORGANISM: Acinetobacter baylyi

<400> SEQUENCE: 25

Leu Thr Ala Phe Val Gln Thr Ile Gln Glu Val Leu Glu Lys Gly His
1               5                   10                  15

Gly Pro Ala Ala Arg Ala Leu Asp Lys Leu Pro Ser Phe Val Gln Glu
            20                  25                  30

Ser Ile Ala Lys Val Leu Gly Tyr Pro Tyr Gln Tyr Pro Gln Leu Asp
        35                  40                  45

Ser Phe Ile Lys Cys Leu Met Ala Val Gln Ile Lys Gln Gly Gln Thr
    50                  55                  60

Gly Phe Ile Gly Ser Asp Val Glu Lys Ser Arg Leu Ala Phe Glu Thr
65                  70                  75                  80

Gln Met Glu Ser Ile Leu Arg Lys Pro Thr Ala Ile Thr Phe Val Glu
                85                  90                  95

Asp Ile Arg Leu Pro Leu Gln Ser Gly Thr Ile Phe Ala Arg His Tyr
            100                 105                 110

His Pro Ala Pro Asn Lys Lys Leu Pro Met Ile Val Phe Tyr His Gly
        115                 120                 125

Gly Gly Phe Val Val Gly Asn Val Asp Thr His Asp Glu Ala Cys Arg
    130                 135                 140

Leu Ile Ala Lys Tyr Ala Asn Ala Gln Val Leu Ser Ile Asp Tyr Pro
145                 150                 155                 160

Leu Ala Pro Glu Val Ser Pro Gln Arg Leu Ile Gln Ser Cys Glu Asp
                165                 170                 175
```

```
Ala Leu Ala Trp Val Tyr Gln Asn Lys Arg His Phe Lys Ile Leu Lys
            180                 185                 190

Asn Gln Ile Ala Val Ala Gly Asp Ser Ala Gly Gly Asn Ile Ser Thr
        195                 200                 205

Val Val Ala Gln Arg Ala Ile Gly Lys Val Tyr Ala Pro Asp Ala Gln
    210                 215                 220

Phe Leu Ile Tyr Pro Val Asp Phe Lys Ser Arg His Pro Ser Phe
225                 230                 235                 240

Tyr Ala Tyr Lys Asp Gly Leu Val Leu Thr Gly Asn Asp Val Asp Tyr
                245                 250                 255

Val Thr Asp Tyr Tyr Ala Thr Lys His Ala Val His Leu Asp Asp Pro
            260                 265                 270

Ile Ile Ser Pro Thr Tyr Gly Asn Phe Lys Lys Leu Ala Pro Ala Tyr
        275                 280                 285

Ile Val Thr Ala Gly His Asp Val Leu His Asp Glu Gly Glu Ile Tyr
    290                 295                 300

Ser His Lys Leu Arg Gln Ala Gly Val Lys Ile His Phe Glu Glu Tyr
305                 310                 315                 320

Leu Asp Gln Thr His Gly Phe Ile Asn Leu Thr Pro Val Ser His Lys
                325                 330                 335

Ala Arg Ala Asn Leu Ile Gln Met Ser Lys Ser Phe Arg Lys Phe Trp
            340                 345                 350

Asn Lys Tyr Ala
        355

<210> SEQ ID NO 26
<211> LENGTH: 294
<212> TYPE: PRT
<213> ORGANISM: Acinetobacter baylyi

<400> SEQUENCE: 26

Met Leu Asn Asn Pro Gln Phe Tyr Val Glu Gln Leu Asn Lys Gln Ile
1               5                   10                  15

Glu Arg Val Lys Glu Gln Tyr Lys Ser Phe Arg Phe Tyr Asp Leu Gly
            20                  25                  30

Ser Tyr Ala Leu Asn Arg Leu Thr Pro Arg Thr Ser Phe Glu Leu Val
        35                  40                  45

Glu Asn Ile Ala Tyr Gly Leu Lys Ser Arg Gln Arg Leu Asp Leu Tyr
    50                  55                  60

Arg Ala Lys Lys Thr Leu Ala His Arg Pro Leu Ile Val Phe Val His
65                  70                  75                  80

Gly Gly Ala Trp Gln His Gly Asp Lys Lys Asp Tyr Val Phe Ile Gly
                85                  90                  95

Glu Ser Leu Ala Arg Ala Gly Tyr Asp Val Ala Val Ile Asn Tyr His
            100                 105                 110

Leu Ala Pro Gln Ser Ile Phe Pro Val Tyr Ile Asp Asp Ile Ala Gln
        115                 120                 125

Ala Leu Asn Tyr Leu Asn Gln His Gln Arg Leu Asn Ile Ser Thr
    130                 135                 140

Gln His Ile Ile Leu Met Gly His Ser Ser Gly Ala Phe Asn Val Met
145                 150                 155                 160

Ser Val Val Tyr His Pro Gln Gln Ala Ile His Cys Arg Asp Gln
                165                 170                 175

Ile Lys Ala Ile Val Gly Phe Ala Gly Pro Tyr His Phe Asp Tyr Lys
            180                 185                 190
```

```
Gly Asp Pro Leu Ala Gln Asp Ala Phe Asp Gln Ser Val Pro Tyr Gln
            195                 200                 205

Glu Val Met Pro Phe Tyr Phe Val Glu Thr Asn Ser Ile Lys His Tyr
210                 215                 220

Leu Phe Leu Ala Glu Asn Asp Gln Ile Val Lys Lys Ser Asn Thr Phe
225                 230                 235                 240

Asp Met His Gln Lys Leu Leu Gln Ala Gly Asn His Ser His Val Ala
            245                 250                 255

Val Ile Ala Lys Thr Gly His Val Thr Ile Ile Ala Thr Leu Ser Ser
            260                 265                 270

Leu Phe Ser Gln Tyr Phe Lys Thr Lys Arg Thr Leu Leu Asn Leu Leu
            275                 280                 285

Lys Glu Thr His Pro Ala
            290

<210> SEQ ID NO 27
<211> LENGTH: 323
<212> TYPE: PRT
<213> ORGANISM: Acinetobacter baylyi

<400> SEQUENCE: 27

Met Lys Arg Ile Phe Ala Asn Leu Tyr Leu Ser Cys Ser Leu Leu Leu
1               5                   10                  15

Pro Ile Thr Thr Thr Ile Ile Tyr Ser Pro Ala Ile Ser Ala Ala Ser
            20                  25                  30

Gly Ile Asp Ile Gln Asn Val Leu Gln Gln Glu Arg Ala Trp Ala Gly
            35                  40                  45

Leu Gln Thr Lys His Leu Lys Val Gly Asp Ile Glu Trp Val Tyr Ser
50                  55                  60

Glu Ser Gly Asn Ser Ser Lys Pro Thr Ile Ile Leu Ile His Gly Leu
65                  70                  75                  80

Ala Gly Ser Arg Asp Asn Trp Asn Arg Val Ala Tyr Asn Leu Thr Pro
            85                  90                  95

Tyr Tyr His Val Ile Ile Pro Asp Leu Pro Ala His Gly Asp Thr Lys
            100                 105                 110

Ile Pro Asn Asp Phe Asp Leu Ser Ile Pro Asn Leu Thr Glu Lys Leu
            115                 120                 125

Arg Arg Phe Ala Glu Ala Gly His Phe Glu Lys Asn Val His Ile Ala
130                 135                 140

Gly His Ser Met Gly Gly Ala Ile Ala Leu Leu Tyr Thr Ala Gln Tyr
145                 150                 155                 160

Pro Leu Glu Thr Lys Ser Leu Leu Val Asp Ser Ala Gly Val Phe
            165                 170                 175

Lys Thr Ala Asn Thr Pro Tyr Leu Lys Asp Pro Asn Leu Leu Asn Asn
            180                 185                 190

Leu Val Val Lys Lys Thr Gly Asp Phe Asp Lys Leu Phe Lys Leu Ala
            195                 200                 205

Thr Ala Ser Pro Pro Phe Ile Pro Val Glu Leu Lys Thr Glu Gln Glu
210                 215                 220

Lys Leu Met Ile Ala Gln Ser Lys Asn Thr Gln Lys Met Val Asp Gln
225                 230                 235                 240

Leu Val Ala Met Ser Lys Ile Tyr Thr Pro Asp Thr Phe Ala Ile Ala
            245                 250                 255

Thr Lys Ser Ile Asp Val Pro Thr Tyr Ile Ile Trp Gly Asp Gln Asp
```

```
                260                 265                 270
Lys Ile Ile Asn Val Glu Ala Ala Gln Glu Leu Lys Ser Leu Leu Lys
            275                 280                 285

Asn Ala Glu Thr Pro Tyr Ile Leu Lys Gly Val Gly His Met Pro Ile
        290                 295                 300

Leu Glu Ala Asp Gln Leu Val Ser Gln Gln Tyr Leu Ile Phe Leu Asn
305                 310                 315                 320

Lys Gln Pro

<210> SEQ ID NO 28
<211> LENGTH: 559
<212> TYPE: PRT
<213> ORGANISM: Acinetobacter baylyi

<400> SEQUENCE: 28

Met Glu Lys Ile Trp Phe Ala Glu Tyr Gln Lys Thr Gly Ile Pro Glu
1               5                   10                  15

Thr Val Glu Leu Pro Pro Glu Asn Thr Ser Leu Val Asp Ile Phe Glu
            20                  25                  30

Arg Asn Phe Gln Lys Phe Gly Ser Arg Asp Ala Phe Ile Phe Met Asp
        35                  40                  45

Lys Ala Leu Thr Phe Asn Glu Leu Glu Glu Ala Ser Arg Lys Phe Ala
    50                  55                  60

Ala Tyr Leu Gln Ser Leu Asn Leu Pro Lys Gly Ser Arg Val Ala Val
65                  70                  75                  80

Met Met Pro Asn Val Leu Gln Tyr Pro Ile Val Ala Leu Gly Val Phe
                85                  90                  95

Arg Ala Gly Leu Val Val Asn Val Asn Pro Leu Tyr Thr Ala Arg
            100                 105                 110

Glu Leu Glu His Gln Leu Asn Asp Ser Gly Ala Glu Val Leu Val Ile
        115                 120                 125

Ile Glu Asn Phe Ala Ser Val Tyr Gln Thr Ile Leu Gly Lys Thr Pro
    130                 135                 140

Val Lys His Val Val Ile Ala Ser Val Gly Asp Met Leu Gly Thr Leu
145                 150                 155                 160

Lys Gly Thr Leu Val Asn Phe Val Leu Arg Lys Val Arg Lys Gln Ile
                165                 170                 175

Pro Ala Trp Asn Val Pro Gly His Val Lys Phe Asn Ser Ala Leu Asn
            180                 185                 190

Lys Val Ser Pro Ser His Tyr Lys Arg Pro Asn Leu Thr Leu Ser Asp
        195                 200                 205

Thr Ala Val Leu Gln Tyr Thr Gly Gly Thr Thr Gly Val Ser Lys Gly
    210                 215                 220

Ala Glu Leu Thr His Arg Asn Leu Val Ala Asn Met Leu Gln Cys Asp
225                 230                 235                 240

Gly Ile Phe Gln Ser Lys Phe Gly Ser Gly Asp Ser Ser Lys Asp Asp
                245                 250                 255

Lys Met Phe Cys Ala Leu Pro Leu Tyr His Ile Phe Ala Phe Met Val
            260                 265                 270

Cys Ala Met Tyr Gly Met Tyr Lys Gly Gln Ala Asn Ile Leu Ile Pro
        275                 280                 285

Asn Pro Arg Asp Leu Pro Ala Val Ile Lys Glu Leu Arg Lys Tyr Gln
    290                 295                 300

Pro Thr Phe Phe Pro Ala Val Asn Thr Leu Phe Asn Ala Leu Val His
```

```
                305                 310                 315                 320
Asn Glu Glu Phe Lys Gln Leu Asp His Ser Lys Leu Lys Ile Ala Met
                325                 330                 335
Gly Gly Gly Met Ala Val Leu Pro Ser Thr Ala Glu Ala Trp Lys Arg
                340                 345                 350
Ile Thr Gly Val Thr Ile Ile Glu Gly Tyr Gly Leu Ser Glu Thr Ser
                355                 360                 365
Pro Val Ala Thr Val Asn Pro Pro Ala Ser Ser Glu Phe Ser Gly Thr
                370                 375                 380
Ile Gly Ile Pro Leu Pro Leu Thr Asp Val Ala Ile Leu Asp Asp Asp
385                 390                 395                 400
Gly His Pro Val Ala Leu Gly Glu Gln Gly Glu Ile Ser Ile Arg Gly
                405                 410                 415
Pro Gln Val Met Lys Gly Tyr Trp Asn Arg Pro Asp Glu Thr Ala Lys
                420                 425                 430
Val Met Thr Ser Asp Gly Phe Phe Arg Thr Gly Asp Ile Gly Val Met
                435                 440                 445
Asn Asp Arg Gly Tyr Val Lys Ile Val Asp Arg Lys Lys Asp Met Ile
450                 455                 460
Leu Val Ser Gly Phe Asn Val Tyr Pro Ser Glu Ile Glu Glu Val Ile
465                 470                 475                 480
Ala Lys His Pro Lys Val Leu Glu Val Ala Ala Ile Gly Val Pro Asp
                485                 490                 495
Glu Lys Ser Gly Glu Val Pro Lys Leu Phe Ile Val Lys Lys Asp Pro
                500                 505                 510
Ser Leu Thr Thr Glu Glu Val Leu Ser Phe Ala Lys Glu Asn Leu Thr
                515                 520                 525
Gly Tyr Lys Arg Pro Arg Tyr Val Glu Phe Met Asp Glu Leu Pro Lys
                530                 535                 540
Ser Asn Val Gly Lys Ile Leu Arg Lys Asp Leu Arg Lys Thr Asn
545                 550                 555

<210> SEQ ID NO 29
<211> LENGTH: 1341
<212> TYPE: DNA
<213> ORGANISM: Artificial
<220> FEATURE:
<223> OTHER INFORMATION: Codon-optimized synthetic gene raSVa

<400> SEQUENCE: 29
atgactccag atccattagc tccattagat ttagcttttt ggaatattga atctgctgaa    60
catccaatgc atttaggtgc tttaggtgtt tttgaagctg attctccaac tgctggtgct   120
ttagctgctg atttattagc tgctcgtgct ccagctgttc aggtttacg tatgcgtatt    180 cgtgatactt ggcaaccacc aatggcttta cgtcgtccat ttgcttttgg tggtgctact   240
cgtgaaccag atccacgttt tgatccatta gatcatgttc gtttacatgc tccagctact   300
gattttcatg ctcgtgctgg tcgtttaatg aacgtccat agaacgtgg tcgtccaccc    360 tgggaagcgc atgtgctacc aggtgctgat ggtggttctt ttgctgtttt atttaaattt   420
catcatgctt tagctgatgg tttacgtgct ttaactttag ctgctggtgt tttagatcca   480
atggatttac cagctccacg tccacgtcca gaacaaccac cgagaggctt attaccagat   540
gttcgtgctt taccagatcg tttacgtggt gctttatctg atgctggtcg tgctttagat   600
attggtgctg ctgctgcg

```
gcttcttctg gtactcgtcg tactgctggt gtttctgttg atttagatga tgttcatcat    720
gttcgtaaaa ctactggtgg tactgttaat gatgttttaa ttgctgttgt tgctggtgct    780
ttacgtcgtt ggttagatga acgtggtgat ggttctgaag gtgttgctcc acgcgcgtta    840
attccagttt cgcgtcgtcg tccacgttct gctcatccac aaggtaatcg tttatctggt    900
tatttaatgc gtttaccagt tggtgatcca gatccattag ctcgtttagg tactgttcgt    960
gctgctatgg atcgtaataa agatgctggt ccaggtcgtg gtgctggtgc tgttgcttta   1020
ttagctgatc atgttccagc tttaggtcat cgtttaggtg gtccactagt ttctggtgct   1080
gctcgtttat ggtttgattt attagttact tctgttccat taccatcttt aggtttacgt   1140
ttaggtggtc atccattaac tgaagtttat ccattagctc cattagctcg tggtcattct   1200
ttagctgttg ctgtttctac ttatcgtggt cgtgttcatt atggtttatt agctgatgct   1260
aaagctgttc cagacctcga tcgtctcgct gttgctgttg ctgaagaagt tgaaacttta   1320
ttaactgctt gtcgtccata a                                             1341
```

<210> SEQ ID NO 30
<211> LENGTH: 446
<212> TYPE: PRT
<213> ORGANISM: Artificial
<220> FEATURE:
<223> OTHER INFORMATION: amino acid sequence analogous to sco0958 from
      Streptomyces coelicolor encoded by a codon-optimized synthetic
      gene raSVa

<400> SEQUENCE: 30

```
Met Thr Pro Asp Pro Leu Ala Pro Leu Asp Leu Ala Phe Trp Asn Ile
1               5                   10                  15

Glu Ser Ala Glu His Pro Met His Leu Gly Ala Leu Gly Val Phe Glu
            20                  25                  30

Ala Asp Ser Pro Thr Ala Gly Ala Leu Ala Ala Asp Leu Leu Ala Ala
        35                  40                  45

Arg Ala Pro Ala Val Pro Gly Leu Arg Met Arg Ile Arg Asp Thr Trp
    50                  55                  60

Gln Pro Pro Met Ala Leu Arg Arg Pro Phe Ala Phe Gly Gly Ala Thr
65                  70                  75                  80

Arg Glu Pro Asp Pro Arg Phe Asp Pro Leu Asp His Val Arg Leu His
                85                  90                  95

Ala Pro Ala Thr Asp Phe His Ala Arg Ala Gly Arg Leu Met Glu Arg
            100                 105                 110

Pro Leu Glu Arg Gly Arg Pro Pro Trp Glu Ala His Val Leu Pro Gly
        115                 120                 125

Ala Asp Gly Gly Ser Phe Ala Val Leu Phe Lys Phe His His Ala Leu
    130                 135                 140

Ala Asp Gly Leu Arg Ala Leu Thr Leu Ala Ala Gly Val Leu Asp Pro
145                 150                 155                 160

Met Asp Leu Pro Ala Pro Arg Pro Arg Pro Glu Gln Pro Pro Arg Gly
                165                 170                 175

Leu Leu Pro Asp Val Arg Ala Leu Pro Asp Arg Leu Arg Gly Ala Leu
            180                 185                 190

Ser Asp Ala Gly Arg Ala Leu Asp Ile Gly Ala Ala Ala Leu Ser
        195                 200                 205

Thr Leu Asp Val Arg Ser Ser Pro Ala Leu Thr Ala Ala Ser Ser Gly
    210                 215                 220
```

Thr Arg Arg Thr Ala Gly Val Ser Val Asp Leu Asp Asp Val His His
225                 230                 235                 240

Val Arg Lys Thr Thr Gly Gly Thr Val Asn Asp Val Leu Ile Ala Val
            245                 250                 255

Val Ala Gly Ala Leu Arg Arg Trp Leu Asp Glu Arg Gly Asp Gly Ser
            260                 265                 270

Glu Gly Val Ala Pro Arg Ala Leu Ile Pro Val Ser Arg Arg Pro
        275                 280                 285

Arg Ser Ala His Pro Gln Gly Asn Arg Leu Ser Gly Tyr Leu Met Arg
        290                 295                 300

Leu Pro Val Gly Asp Pro Asp Pro Leu Ala Arg Leu Gly Thr Val Arg
305                 310                 315                 320

Ala Ala Met Asp Arg Asn Lys Asp Ala Gly Pro Gly Arg Gly Ala Gly
                325                 330                 335

Ala Val Ala Leu Leu Ala Asp His Val Pro Ala Leu Gly His Arg Leu
            340                 345                 350

Gly Gly Pro Leu Val Ser Gly Ala Ala Arg Leu Trp Phe Asp Leu Leu
        355                 360                 365

Val Thr Ser Val Pro Leu Pro Ser Leu Gly Leu Arg Leu Gly Gly His
370                 375                 380

Pro Leu Thr Glu Val Tyr Pro Leu Ala Pro Leu Ala Arg Gly His Ser
385                 390                 395                 400

Leu Ala Val Ala Val Ser Thr Tyr Arg Gly Arg Val His Tyr Gly Leu
                405                 410                 415

Leu Ala Asp Ala Lys Ala Val Pro Asp Leu Asp Arg Leu Ala Val Ala
            420                 425                 430

Val Ala Glu Glu Val Glu Thr Leu Leu Thr Ala Cys Arg Pro
435                 440                 445

<210> SEQ ID NO 31
<211> LENGTH: 1377
<212> TYPE: DNA
<213> ORGANISM: Acinetobacter baylyi

<400> SEQUENCE: 31
atgcgcccat acatccgat tgattttata ttcctgtcac tagaaaaaag acaacagcct    60
atgcatgtag gtggtttatt tttgtttcag attcctgata cgccccaga cacctttatt   120 caagatctgg tgaatgatat ccggatatca aaatcaatcc ctgttccacc attcaacaat   180
aaactgaatg gctttttttg ggatgaagat gaagagtttg atttagatca tcattttcgt   240
catattgcac tgcctcatcc tggtcgtatt cgtgaattgc ttatttatat ttcacaagag   300
cacagtacgc tgctagatcg ggcaaagccc ttgtggacct gcaatattat tgaaggaatt   360
gaaggcaatc gttttgccat gtacttcaaa attcaccatg cgatggtcga tggcgttgct   420
ggtatgcggt taattgaaaa atcactctcc catgatgtaa cagaaaaaag tatcgtgcca   480
ccttggtgtg ttgagggaaa acgtgcaaag cgcttaagag aacctaaaac aggtaaaatt   540
aagaaaatca tgtctggtat taagagtcag cttcaggcga cacccacagt cattcaagag   600
ctttctcaga cagtatttaa agatattgga cgtaatcctg atcatgtttc aagctttcag   660
gcgccttgtt ctattttgaa tcagcgtgtg agctcatcgc gacgttttgc agcacagtct   720
tttgacctag atcgttttcg taatattgcc aaatcgttga atgtgaccat taatgatgtt   780
gtactagcgg tatgttctgg tgcattacgt gcgtatttga tgagtcataa tagttttgcct   840 tcaaaaccat taattgccat ggttccagcc tctattcgca atgacgattc agatgtcagc   900

```
aaccgtatta cgatgattct ggcaaatttg caacccaca aagatgatcc tttacaacgt    960
cttgaaatta tccgccgtag tgttcaaaac tcaaagcaac gcttcaaacg tatgaccagc   1020
gatcagattc taaattatag tgctgtcgta tatggccctg caggactcaa cataatttct   1080
ggcatgatgc caaaacgcca agccttcaat ctggttattt ccaatgtgcc tggcccaaga   1140
gagccacttt actggaatgg tgccaaactt gatgcactct acccagcttc aattgtatta   1200
gacggtcaag cattgaatat tacaatgacc agttatttag ataaacttga agttggtttg   1260
attgcatgcc gtaatgcatt gccaagaatg cagaatttac tgacacattt agaagaagaa   1320
attcaactat ttgaaggcgt aattgcaaag caggaagata ttaaaacagc caattaa     1377
```

<210> SEQ ID NO 32
<211> LENGTH: 458
<212> TYPE: PRT
<213> ORGANISM: Acinetobacter baylyi

<400> SEQUENCE: 32

```
Met Arg Pro Leu His Pro Ile Asp Phe Ile Phe Leu Ser Leu Glu Lys
1               5                  10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285
```

```
Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
                340                 345                 350

Pro Ala Gly Leu Asn Ile Ile Ser Gly Met Met Pro Lys Arg Gln Ala
            355                 360                 365

Phe Asn Leu Val Ile Ser Asn Val Pro Gly Pro Arg Glu Pro Leu Tyr
        370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
    450                 455
```

GENETICALLY MODIFIED *ACINETOBACTER* HOSTS FOR LIPID PRODUCTION

CROSS-REFERENCE TO RELATED APPLICATION

The present application claims the benefit of priority under 35 U.S.C. §119(e) to U.S. Provisional Patent Application No. 61/424,387, filed on Dec. 17, 2010, the content of which is incorporated herein by reference in its entirety.

FIELD OF THE INVENTION

The present invention relates to a genetically modified *Acinetobacter* host and to a process for producing lipids by using the host.

BACKGROUND OF THE INVENTION

The use of renewable biological material for the production of biofuels is generally motivated by decreasing climate change impacts, by securing the supply of fuels and by economic factors. Lipids are used as a raw material for the production of transportation biofuels, such as biodiesel or renewable diesel, or as their components, for their high energy content and availability. Current raw materials for biodiesel and renewable diesel include vegetable oils, animal fats or recycled greases. Since algae and some other microorganisms are known to naturally produce a wide range of lipids, their use as the source of lipids for biodiesel has been suggested. These microorganism based oils are often called as single cell oils. Lipids are essential for the cell as membrane components, enzyme co-factors, and carbon and energy storages. Some of these lipids, especially triacylglycerols (TAGs), are suitable for biodiesel and/or renewable diesel production.

Many challenges faced with agriculture based raw material, such as vegetable oils. for biodiesel and/or renewable diesel can be reduced with microbial biofuel production. Autotrophic algae are suggested to have significantly higher annual lipid yields per hectare than best oil crops. Alternative option to photosynthetic (autotrophic) production of lipids by algae or cyanobacteria is to utilize heterotrophic microorganisms which produce lipids from organic molecules (such as sugars) without need for light. Importantly, heterotrophic microorganisms can utilize various organic wastes and residues as raw materials for lipid production. Lipid production process using heterotrophic microorganisms comprises cultivating microorganisms in aerated bioreactors, allowing cells to accumulate lipids, harvesting lipid-rich cells and recovering oil from cells.

Single-cell oils have traditionally been used as special products e.g. in health foods, not as commodity chemicals. In these kinds of single cell oil production processes product volumes are relatively small and the product is expensive. Therefore, the cost structure of these processes allows the utilization of expensive feed raw materials and unit operations. Similar kind of production process has also been described for the production of lipids for biodiesel production (Ratledge and Cohen 2008). However, as the product is an inexpensive commodity chemical, the process costs should not be on the level of the process costs of special products. When lipids are used for example as starting material for biodiesel or renewable diesel, it is important that the lipid production process is efficient in terms of lipid yield from substrate and lipid production rate. Since the typical lipid yield by heterotrophic microorganisms is less than 20% weight percent of the fed sugar, the price of raw material has an essential role in cost structure. Since the economy of the production of single cell oils for biofuels is of key importance, new cost-effective processes for lipid production for biofuel production are still of growing interest. Further, the development of more efficient lipid producing organisms is of high interest.

Some bacteria can produce storage lipids, which can be utilized for example as starting material for biodiesel or renewable diesel production. Storage lipids are free fatty acids, acylglycerols, and wax esters and intermediate products thereof. The synthesis of storage lipids is a regulated process in bacteria. The production of storage lipids can be made more efficient by making some genes in the genome of the bacteria inactive and/or by overexpressing some genes in the genome of the bacteria. Such genes have been described for example in the patent publications WO2009/009391 and WO2008/119082. WO2009/009391 discloses a method for making a fatty esters using impure or unpurified alcohol in the production. The recombinant cell used in the method lacks a nucleic acid sequence encoding acyl-CoA dehydrogenase enzyme or the expression of said enzyme is attenuated. The host may comprise also exogenous genes encoding thioesterase, wax synthase, alcohol acetyltransferase, fatty alcohol forming acyl-CoA-reductase, an ester synthase enzyme, or acyl-CoA synthase enzyme. WO2008/119082 discloses recombinant cells from various microorganism hosts expressing or over-expressing gene or genes encoding fatty acid derivative enzymes and a gene encoding an acyl-CoA dehydrogenase enzyme, which gene is modified such that expression of the gene is attenuated.

Various patent publications describe the expression of some genes of the lipid synthesis pathway. WO2008/113041 discloses cracking methods for producing low molecular weight hydrocarbons from biocrude or hydrocarbon feedstock, which may be produced from a recombinant microorganism. The recombinant microorganism may be engineered to express or overexpress peptides, for example acyl-CoA synthetase, thioesterase, acetyl-CoA carboxylase or acyl-carrier protein. WO2007/136762 discloses genetically engineered microorganisms that are capable of synthesizing products derived from the fatty acid biosynthetic pathway (fatty acid derivatives).

Furthermore, DE102004052115 discloses a microorganism comprising a nucleic acid molecule encoding procaryotic acyltransferase, a nucleic acid molecule encoding pyruvatdecarboxylase and a nucleic acid molecule encoding alcoholdehydrogenase.

US 2003145350 discloses a method for increasing the content of short or middle chain length fatty acids in microorganisms and for production of fatty acids and oils having an increased content of short or middle chain length fatty acids. The method comprises the expression of the acyltransferase KAS III in a microorganism.

Although some publications disclose improved microorganism strains for lipid production there is still a need for more efficient processes for lipid production in order to obtain affordable raw material for biofuel and other applications.

SUMMARY OF THE INVENTION

One object of the present invention is to provide a microorganism host capable of improved lipid production Another object of the invention is to provide an efficient process for producing lipids.

In particular, one object of the invention is to provide a process for producing lipids for biofuel, for components or for starting material for biofuel production.

To achieve these objects the invention is characterized by the features that are enlisted in the independent claims. Other claims represent the preferred embodiments of the invention.

In one aspect the present invention provides an *Acinetobacter* host genetically modified to produce efficiently lipids. More specifically, the invention provides a host that is genetically modified to be deficient of one or more of genes. Genes which are advantageously made deficient in the host encode for example some key enzymes of the biochemical pathways competing with the lipid biosynthesis pathway.

The invention is based on the finding that the production of storage lipids can be significantly improved by making the host deficient of one or more genes encoding fatty acyl-CoA reductase, gene ACIAD 3383 or a functional equivalent thereof in an *Acinetobacter* host, and/or one or more genes encoding lipase, gene ACIAD 3309 or a functional equivalent thereof in an *Acinetobacter* host, pyruvate dehydrogenase, gene ACIAD 3381 or a functional equivalent thereof in an *Acinetobacter* host, or gene ACIAD 2177 or a functional equivalent thereof in an *Acinetobacter* host. *Acinetobacter* hosts modified according to this invention produce significantly higher amount storage lipids at cellular level than the wild type strain. More specifically, it is of advantage to make an *Acinetobacter* host deficient of one or more genes of group A, or one or more genes of group B, or one or more genes of both groups. Hence, an *Acinetobacter* host may be made deficient of one or more of A) a gene encoding fatty acyl-CoA reductase (EC1.2.1.n2), gene ACIAD 3383 (SEQ ID NO:1) or a functional equivalent thereof in an *Acinetobacter* host, wherein said host is capable of increased production of triacylglycerols (TAGs) and/or of total lipids compared to the parent host;
and/or B) a gene encoding lipase (EC:3.1.1.3), gene ACIAD 3309 (SEQ ID NO: 2) or a functional equivalent thereof in an *Acinetobacter* host, a gene encoding pyruvate dehydrogenase (EC:1.2.2.2), gene ACIAD 3381 (SEQ ID NO:3) or a functional equivalent thereof in an *Acinetobacter* host, or gene ACIAD 2177 (SEQ ID NO:4) or a functional equivalent thereof in an *Acinetobacter* host, wherein said host is capable of increased production of wax esters (WEs) and/or total lipids compared to the parent host.

In another embodiment of the invention the host may be made deficient of one or more of A) a gene encoding fatty acyl-CoA reductase (EC1.2.1.n2), gene ACIAD 3383 (SEQ ID NO:1) or a functional equivalent thereof in an *Acinetobacter* host; and/or B) a gene encoding diacylglycerol kinase (EC:2.7.1.107), gene ACIAD 2837

(SEQ ID NO:5) or a functional equivalent thereof in an *Acinetobacter* host, succinate dehydrogenase (EC:1.3.5.1), gene ACIAD 2880 (SEQ ID NO:6) or a functional equivalent thereof in an *Acinetobacter* host, glycerol-3-phosphate dehydrogenase (EC 1.1.5.3), gene ACIAD 2844 (SEQ ID NO:7) or a functional equivalent thereof in an *Acinetobacter* host, cytochrome o ubiquinol oxidase subunit II (EC:1.10.3.-), gene ACIAD 2425 (SEQ ID NO:8) or a functional equivalent thereof in an *Acinetobacter* host, cytochrome o ubiquinol oxidase subunit I (EC:1.10.3.-), gene ACIAD 2426 (SEQ ID NO:9), or a functional equivalent thereof in an *Acinetobacter* host, cytochrome d terminal oxidase polypeptide subunit II (EC1.10.3.-), gene ACIAD 2291 (SEQ ID NO:10) or a functional equivalent thereof in an *Acinetobacter* host, pyruvate dehydrogenase (EC:1.2.2.2), gene ACIAD 3381 (SEQ ID NO:3) or a functional equivalent thereof in an *Acinetobacter* host, carboxylesterase (EC:3.1.1.1), gene ACIAD 3648 (SEQ ID NO:11) or a functional equivalent thereof in an *Acinetobacter* host, esterase, gene ACIAD 1134 (SEQ ID NO:12) or a functional equivalent thereof in an *Acinetobacter* host; various lipases (EC:3.1.1.3), gene ACIAD 1121 (SEQ ID NO:13) or a functional equivalent thereof in an *Acinetobacter* host, gene ACIAD 3309 (SEQ ID NO:2) or a functional equivalent thereof in an *Acinetobacter* host, acyl-CoA synthetase (EC: 6.2.1.3), gene ACIAD 0235 (SEQ ID NO:14) or a functional equivalent thereof in an *Acinetobacter* host, or gene ACIAD 2177 (SEQ ID NO:4) or a functional equivalent thereof in an *Acinetobacter* host,
wherein said host is capable of increased production of TAGs, wax esters and/or total lipids compared to the parent host.

In one further embodiment of the invention the host may be made deficient of one or more of A) a gene encoding fatty acyl-CoA reductase (EC1.2.1.n2), gene ACIAD 3383 (SEQ ID NO:1) or a functional equivalent thereof in an *Acinetobacter* host; and/or B) a gene encoding cytochrome o ubiquinol oxidase subunit II (EC:1.10.3.-), gene ACIAD 2425 (SEQ ID NO:8) or a functional equivalent thereof in an *Acinetobacter* host, or succinate dehydrogenase (EC:1.3.5.1), gene ACIAD 2880 (SEQ ID NO:6), or a functional equivalent thereof in an *Acinetobacter* host,
wherein said host is capable of increased production of TAGs, wax esters and/or of total lipids compared to the parent strain.

In one further embodiment of the invention the host may be made deficient of one or more of lipases (EC:3.1.1.3), gene ACIAD 3309 (SEQ ID NO:2) or a functional equivalent thereof in an *Acinetobacter* host, pyruvate dehydrogenase (EC:1.2.2.2), gene ACIAD 3381 (SEQ ID NO:3), or a functional equivalent thereof in an *Acinetobacter* host and/or gene ACIAD2177 (SEQ ID NO:4) or a functional equivalent thereof in an *Acinetobacter* host, wherein said host is capable of increased production of wax esters (WEs) and/or total lipids.

In one still further embodiment of the invention the host may be made deficient of one or more lipases (EC:3.1.1.3), gene ACIAD 3309 (SEQ ID NO:2) or a functional equivalent thereof in an *Acinetobacter* host, pyruvate dehydrogenase (EC:1.2.2.2), gene ACIAD 3381 (SEQ ID NO:3) or a functional equivalent thereof in an *Acinetobacter* host, and/or gene ACIAD 2177 (SEQ ID NO:4) or a functional equivalent thereof in an *Acinetobacter* host together with one or more of a gene encoding diacylglycerol kinase (EC:2.7.1.107), gene ACIAD 2837 (SEQ ID NO:5) or a functional equivalent thereof in an *Acinetobacter* host; a gene encoding fatty acyl-CoA reductase (EC1.2.1.n2), gene ACIAD 3383 (SEQ ID NO:1), or a functional equivalent thereof in an *Acinetobacter* host; a gene encoding succinate dehydrogenase (EC:1.3.5.1), gene ACIAD 2880 (SEQ ID NO:6) or a functional equivalent thereof in an *Acinetobacter* host; a gene encoding glycerol-3-phosphate dehydrogenase (EC 1.1.5.3), gene ACIAD 2844 (SEQ ID NO:7) or a functional equivalent thereof in an *Acinetobacter* host; a gene encoding cytochrome o ubiquinol oxidase subunit II (EC:1.10.3.-), gene ACIAD 2425 (SEQ ID NO:8) or a functional equivalent thereof in an *Acinetobacter* host; a gene encoding cytochrome o ubiquinol oxidase subunit I (EC:1.10.3.-), gene ACIAD 2426 (SEQ ID NO:9), or a functional equivalent thereof in an *Acinetobacter* host; a gene encoding cytochrome d terminal oxidase polypeptide subunit II (EC:1.10.3.-), gene ACIAD 2291 (SEQ ID NO:10, or a functional equivalent thereof in an *Acinetobacter* host; a gene encoding pyruvate dehydrogenase (EC1.2.2.2), gene ACIAD 3381 (SEQ ID NO:3) or a functional equivalent thereof in an *Acinetobacter* host, a gene encoding carboxylesterase (EC: 3.1.1.1), gene ACIAD 3648 (SEQ ID NO:11), or a functional equivalent thereof in an *Acinetobacter* host, a gene encoding esterase, gene ACIAD 1134 (SEQ ID NO:12), or a functional equivalent thereof in an *Acinetobacter* host, various lipases (EC:3.1.1.3), gene ACIAD 1121 (SEQ ID NO:13) or a functional equivalent thereof in an *Acinetobacter* host, or a gene encoding acyl-CoA synthetase (EC:6.2.1.3), gene ACIAD 0235 (SEQ ID NO:14) or a functional equivalent thereof in an *Acinetobacter* host, wherein said host is capable of increased production of wax esters (Wes) and/or of total lipids.

In one still further embodiment of the invention the host may be genetically modified to express one or more genes encoding the enzymes of lipid biosynthesis pathway.

In one still further embodiment of the invention the host may be genetically modified to express a gene encoding diacylglyserol synthase enzyme or to overexpress a gene encoding WS and/or DGAT.

In another aspect the invention provides a process for producing lipids. The process comprises cultivating the modified microorganisms under suitable cultivation conditions; allowing microorganism to accumulate lipids; and recovering the lipids.

Yet, in another aspect the invention provides a process for producing biofuel. The process comprises cultivating the modified microorganisms under suitable cultivation conditions; allowing microorganisms to accumulate lipids; recovering the lipids; and producing biofuel using the recovered lipids as a component or starting material for biofuel, such as biodiesel and/or renewable diesel.

In one further aspect the invention provides lipid compositions produced by the embodiments of the invention.

In one still further aspect the invention provides use of the modified hosts for producing lipids and use of the lipids as biofuel, as a component of biofuel, or as a starting material for biofuel production.

In some variations of the invention the host may be made deficient of at least 1, 2, 3, 4 or 5 genes.

Considerable advantages are obtained by means of the present invention. By means of the invention new microorganisms belonging to the genus *Acinetobacter* are obtained, said microorganisms being capable of improved lipid production.

DETAILED DESCRIPTION OF THE INVENTION

Figure 1:
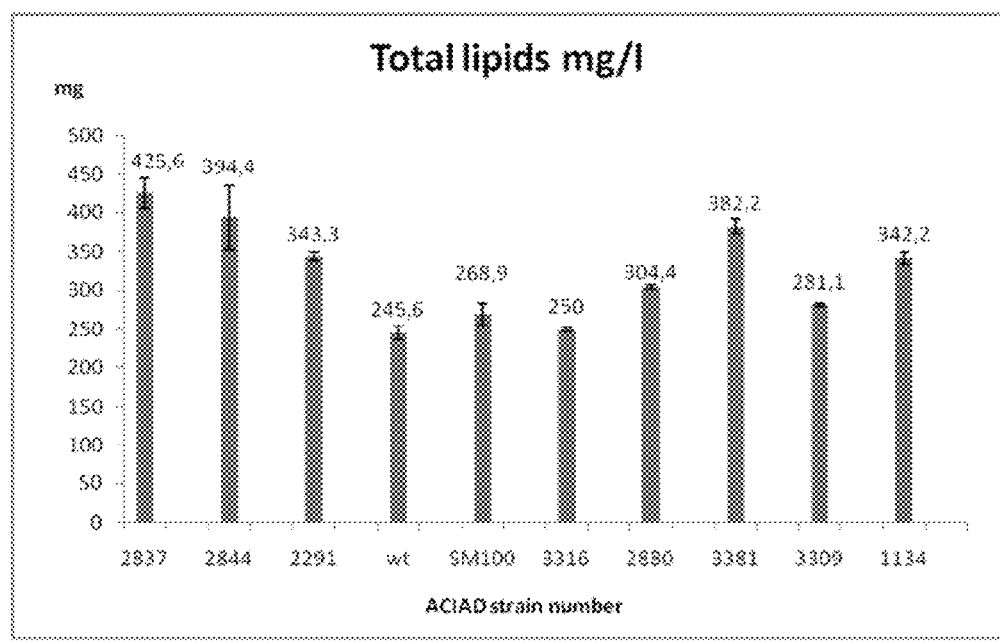
FIG. 1 shows the gravimetric analysis of total lipids of the mutant strains.

The present invention provides new genetically modified *Acinetobacter* hosts in which a specific gene or genes are made deficient, typically inactive, in order to make the lipid production more efficient. In addition, lipid production may be further improved by introducing genetic constructs comprising genes of the lipid biosynthesis pathway.

"A genetically modified microorganism" refers here to a genetically modified *Acinetobacter* host whose genetic material has been altered using genetic engineering techniques. For example, one or more genes may be made deficient, typically inactive, in the host microorganism or one, or more endogenous or exogenous genes may be expressed or overexpressed in the host. "A gene" refers here typically to a nucleotide sequence encoding a specific product, here usually an enzyme.

"Making deficient a gene in a host" means a genetic modification of the host by any suitable method resulting in reduced or lacking expression of a specific gene or reduced or lacking activity of a specific gene product. The method may comprise deletion or truncation or other modification of a specific gene, in particular a gene responsible of pathways competing with lipid biosynthesis. By "inactivation" is meant a genetic modification, typically deletion, resulting in complete loss of activity of a gene product. The effect of the genetic modification of a specific gene on lipid production can be studied by determining the amount of total lipids, storage lipids, structural lipids and/or specific lipid compounds (e.g. triacylgcerols, wax esters.

The term "lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as triacylglycerols, diacylglycerols, or mono-acylglycerols.

Preferred lipids in the present invention are fats, oils, waxes, acylglycerols and fatty acids and their derivatives, in particular triacylglycerols and wax esters.

Term "total lipids" refers to the sum of all compounds classified as lipids. Total lipids can be determined e.g. per weight of in cell biomass (per wet or dry weight) or per weight in cultivation volume. An increase in total lipids or improved total lipid production means that at least one of the compounds classified as lipids is increased increasing the sum of all lipid compounds.

The term "acyglycerol" refers to an ester of glycerol and fatty acids. Acylglycerols occur naturally as fats and fatty oils. Examples of acylglycerols include triacylglycerols (TAGs, triglycerides) diacylglycerols (diglycerides) and monoacylglycerols (monoglycerides). Triacylglycerols (TAG) are non-polar and hydrophobic glycerol triesters with three fatty acids. The properties of TAG are dependent on their fatty acid composition.

The term "wax ester" (WE) refers to an ester of fatty acids with long-chain monohydric alcohols which dissolves in nonpolar organic solvents but is poorly soluble in water.

The term "storage lipids" can be defined as lipids which microorganisms store intracellularly mainly for the purpose of storing energy, and fatty acids required for lipid biosynthesis in cells. Typically storage lipids are non-polar lipids such as triacylglycerols, wax esters and/or polyhydroxyalkanoates. Storage lipids are typically located in intracellular inclusions in microbial cells. In some cases, these non-polar lipids are excreted out of cells to growth medium. Storage lipids differ from "structural lipids" or membrane lipids which are included vital cell structures, such as cell membranes. Structural lipids are typically polar lipids such as phospholipids, glycolipids and/or sphingolipids. Structural lipids also include sterols.

By "increased" or "improved" lipid production is here meant increased or improved production of total lipids, or increased or improved production of storage lipids, or increase in particular lipid compounds such as TAGs and/or wax esters by the modified micro-organisms. The increased lipid production can be measured as changes in the amounts of total lipids, storage lipids, structural lipids and/or specific lipid compounds (e.g. TAG, WE) compared to the wild-type or to the parent host. The increase or improvement of at least one of these factors is at least 5%, preferably at least 10%, preferably at least 15%, more preferably at least 20%, still more preferably at least 25%, more and more preferably at least 30%, still more preferably at least 40%, still more preferably at least 50%, still more preferably at least 60%, still more preferably at least 70% in weight compared to the lipid production in the wild-type or parent host determined in terms of lipid production per time, lipid production per biomass, lipid production per cultivation volume or lipid production per consumed substrate (carbon source). Increased or improved lipid production can be achieved by genetic modification that increases one or more of the properties: lipid production per time, lipid production per biomass, lipid production per cultivation volume, lipid production per consumed substrate (carbon source) and/or lipid stability over time, or by genetic modification that increases or improves production of the specific lipid compounds (TAG, WE). In some embodiments of the invention the production of total lipids is increased or improved; in some preferred embodiments the production of TAGs and/or WEs is increased or improved.

By "parent host" or "parent strain" is meant typically a host or a strain without the specific genetic modification resulting in increased or improved lipid production. The parent host may be the wild-type host or for example a production host, having improved properties, such as stability.

By an *Acinetobacter* host is here meant a bacterial host belonging to the genus *Acinetobacter* classified as compiled by DSMZ-Deutsche Sammlung von Mikroorganismen und Zellkulturen GmbH, Braunschweig, Germany, October 2010. More specifically the host may belong to species *Acinetobacter baumannii, A. baylyi, A. beijerinckii, A. bereziniae, A. bouvetii, A. calcoaceticus, A. gemeri, A. grimontii* (synonym *A. junii*), *A. guillouiae, A. gyllenbergii A. haemolyticus, A. johnsonii, A. junii, A. lwoffii, A. parvus, A. radioresistens, A. schindleri, A. soli, A. tandoii, A. tjernbergiae, A. towneri, A. ursingii*, or *A. venetianus*. The preferred species is *A. baylyi*.

The invention has been exemplified by using *A. baylyi* ADP 1 and *A. baylyi* B2 strains. The strains are wild type strains, which are available to the public from recognized depository culture collections; the strain B2 is available from Deutsche Sammlung von Mikroorganismen und Zellkulturen GmbH, Braunschweig, Germany, under accession number DSM14961, and the ADP1 strain from AmericanType Culture Collection, under accession number ATCC 33305.

*Acinetobacter* strains, in general, have a wide substrate (carbon source) utilization range. Several *Acinetobacter* strains can utilize a wide range of sugars (carbohydrates), such as hexose (C6) or pentose (C5) sugars, polar and non-polar hydrocarbons, such as aliphatic alcohols, long-chain fatty acids, glycols and polyols, aromatic and halogenated compounds, amino acids, amines and various nitrogenous compounds, alkanes, and organic acids as a sole carbon and energy source. Wide substrate utilization range is beneficial, since it enables the utilization of a variety of raw materials as carbon sources in cultivations for lipid production. Carbohydrates, in particular sugars, for the cultivation and lipid production by *Acinetobacter* can be derived from agricultural crops (e.g. sugar crops, sugar beet, sugar cane, grains, wheat, barley, maize, cassaya, sweet sorghum, jerusalem artichoke), lignocellulosic materials (e.g. agricultural residues, wood residues, energy crops, pulp and paper industry residues), industrial organic wastes, municipal organic wastes or algae biomass or residues. Materials containing complex polymers, such as lignocellulosic materials, and polymeric sugars such as cellulose, xylan or starch, can be depolymerized (hydrolysis) before use as substrate for *Acinetobacter*, if needed. Advantageously, e.g. hosts belonging to *Acinetobacter baylyi* species (exemplified by using strain ADP1), can utilize both hexose and pentose sugars, which is beneficial for the use of lignocellulosic materials, their fractions or hydrolysates as raw materials for lipid production.

Species of *Acinetobacter* are strict aerobes and their catabolism is shifted towards utilizing substrates that can be directly processed in citric acid cycle, for which all the genes are present. Also glyoxylate cycle via anaplerotic reactions is functional due to the presence of the key enzymes, isocitrate lyase and malate synthase.

*Acinetobacter* species and strains can produce a number of extra- and intracellular biopolymers. *Acinetobacter* species, for example *A. baylyi* can accumulate wax esters (Fixter et al. 1986), triacylglycerols (Kalscheuer and Steinbüchel 2003) and polyhydroxyalkalonic acids (Krehenbrink et al. 2002).

Genetically modified *Acinetobacter* hosts are suitable in particular for biofuel applications; the main constituents of the fatty acids, C16 and C18 fatty acids (16 and 18 carbon fatty acids), are desirable raw materials for biodiesel or renewable diesel. In various embodiments of the present invention the fatty acid profile has been found to be very homogenic regardless of the medium composition, growth phase or genetically modified strains used, which makes *Acinetobacter* hosts suitably for variable bioprocess conditions. In some embodiments more than about 70% of the components are C16:0, C16:1, C18:0 and C18:1 fatty acids. Minor amounts of C12:0, C13:1 and C14:0 fatty acids are also present.

The lipids produced by *Acinetobacter* are relatively saturated meaning that the amount of double bonds in fatty acid moieties is low. This is beneficial for the production of renewable diesel, since it reduces the quantity of hydrogen in hydrogen treatment step (hydrogen deoxygenation, hydroprocessing).

In summary, *Acinetobacter* hosts can utilize a wide range of substrates and produce commercially interesting biopolymers. The strains are tolerant to many toxic compounds and are able to degrade aromatic compounds and complex lignin derivates containing phenol groups. *Acinetobacter* hosts are therefore ideal hosts for lipid production in large scale for biofuel and other applications.

The *Acinetobacter* hosts can be cultivated in a cultivation medium in a bioreactor, or fermentor. During the cultivation the microorganisms produce lipids, in particular storage lipids, which can be recovered after the cultivation, during the cultivation or at regular intervals. The cultiation can thus be batch, continuous or fed-batch cultivation, or any other type of cultivation.

"Suitable cultivation conditions" mean here conditions under which the *Acinetobacter* host is able to grow and produce lipids. The cultivation is typically carried out in a fermentor under suitable aeration and agitation. The cultivation medium is provided with suitable carbon sources, nutrients, such as amino acids, salts, typically mineral salts, trace elements and water. The strain can be cultivated in rich or minimal salt media.

In one embodiment *Acinetobacter* strains can be cultivated using algae biomass or residues, of species such as, but not limited to, *Chlorella, Phaeodactylum, Dunaliella, Nannochloropsis* or *Nannochioris* as a carbon and/or energy source. Algae biomass can be used with or without oil-extraction or recovery of carbohydrates before use.

In another embodiment *Acinetobacter* strains can be cultivated on sugars derived from various different cellulosic or lignocellulosic materials, e.g., but not limited to, agricultural residues like wheat, barley, rye or rice straw, corn stalk or sugar canebagasse, wood materials or residues, pulp and paper industy residues or side streams, energy crops like switchgrass, reed canary grass, Miscanthus or poplar, or paper waste. *Acinetobacter* strains can grow on glucose abundant in cellulosic fraction in lignocellulosic meterials and on xylose, which is abundant component in hemicellulose fractions of several lignocellulosic materials.

The cultivation temperature is 18 to 38° C., generally 20 to 38° C., usually 28 to 32° C., typically about 30° C. The optimal temperature range is from 25° C. to 37° C. Suitable pH is from pH 6 to 8, optimal pH is about pH 7. The generation time is around 30-60 minutes depending on the conditions. Aeration of the liquid cultures is required. Agitation is preferably 100 rpm to 800 rpm, more preferably 250-400 rpm.

"Biofuel" refers to solid, liquid or gaseous fuel mainly derived from biomass or biowaste and is different from fossil fuels, which are derived from the organic remains of prehistoric plants, animals and/or microorganisms.

In a preferred embodiment of the invention the lipids are produced by using *Acinetobacter* hosts and recovered after cultivation and used as feedstock for the production of biodiesel, renewable diesel, jet fuel, gasoline or base oil components and the like.

By the term "biodiesel" is meant here diesel which consists of fatty acid alkyl esters, and is typically produced by transesterification. In transesterification, the acylglycerols are converted to long-chain fatty acid alkyl esters, such as methyl, ethyl or propyl esters. According to EU directive 2003/30/EU "biodiesel" refers to a methyl-ester produced from vegetable oil or animal oil, of diesel quality to be used as biofuel.

"Renewable diesel" refers to a fuel which is produced by a hydrogen treatment of lipids such as hydrogen deoxygenation, hydrogenation or hydroprocessing. In hydrogen treatment, acylglycerols are converted to corresponding alkanes i.e. paraffins or saturated hydrocarbons. The paraffins can be further modified by isomerization or by other process alternatives. Renewable diesel can be produced also from waxes derived from biomass by gasification and Fischer-Tropsch synthesis. Renewable diesel process is optionally used to produce jet fuel and/or gasoline. In addition, cracking of lipids can be performed to produce biofuels. Furthermore, lipids are preferably used as biofuels directly without any further treatment in certain applications.

Raw materials for the production biodiesel and/or renewable diesel can be originated from plant or vegetable oil, animal oil or fat or from a lipid from microorganism, such as bacterium, fungi (a yeast or a filamentous fungus) or a microalgae.

The production of renewable diesel has been described in patent publications EP 1396531, EP1398364, EP 1741767 and EP1741768.

Biodiesel or renewable diesel may be blended with diesel made from fossil fuels. Suitable additives, such as preservatives and antioxidants may be added to the fuel product.

"Lubricant" refers to a substance, such as grease, lipid or oil, that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demulsifiers, antifoaming agents, cosolvents, and lubricity additives (see for example U.S. Pat. No. 7,691, 792). Base oil for lubricant can originate from mineral oil, plant or vegetable oil, animal oil or fat or from a lipid from a microorganism. Base oil can also originate from waxes derived from biomass by gasification and Fischer-Tropsch synthesis. Viscosity index is used to characterise base oil. Typically high viscosity index is preferred.

In an embodiment of the invention biofuel is produced by a method, which comprises that *Acinetobacter* hosts are cultivated under suitable cultivation conditions to produce lipids and the lipids are recovered. Biofuel or lubricant is produced by using the recovered lipids as a component or as a starting material for biofuel or lubricant production. "As a component" of biofuel or lubricant means that the lipids can be used without further treatment, but suitable additives may be added. "As a starting material" means that the lipids are treated with suitable methods, such as transesterification, hydrogen treatment (hydrogen deoxygenation, hydrogenation or hydroprocessing), isomerization, cracking etc.

In microorganisms storage compounds serve as energy, carbon or nitrogen source during periods of starvation of a microorganism. Due to the hydrophobic properties of reserve materials they can be accumulated into cells in large quantities without changing the osmotic pressure of the cell.

*Acinetobacter* genus bacteria produce storage lipids in the form of TAGs and wax esters (WE) by using an enzyme which has both TAG and WE activity. This has been shown in *A. baylyi* by Stöveken et al (2005) J. Bacteriol. February; 187(4): 1369-76. The enzyme WS/DGAT bifunctional wax ester synthase/acyl coenzyme A:diacylglycerol acyltransferase, EC 2.3.1.75 and EC 2.3.1.20, catalyzing the synthesis of both wax esters and triacylglycerols is a membrane-bound bifunctional enzyme WS/DGAT encoded by the gene aftA. The enzyme possesses both acylalcohol acyltransferase (wax ester synthase, WS) activity and acylCoA:diacylglycerol acyltransferase (DGAT) activity. The substrate range of the enzyme is wide and for example alkanes and fatty alcohols of several lengths can be utilized for lipid synthesis (Stöveken and Steinbüchel 2008). In genetical modifications of the gene the encoded activities may change. Hence, in some embodiments of the invention a genetically modified nucleotide sequence encodes either or both activities, WS and/or DGAT.

Accumulation of TAG and WE usually occurs during stationary growth phase when a carbon source is present in the medium in excess and some nutrient, typically nitrogen, is limiting the growth, shifting the biosynthesis of phospholipids towards synthesis of neutral lipids.

Triacylglycerols and wax esters (WE) like many other storage compounds often occur as intracellular lipid inclusions. The quantity and properties, e.g. fatty acid chain lengths, is depend on the *Acinetobacter* strain and growth conditions.

In one embodiment of the invention the production of lipids is increased in *Acinetobacter* hosts by genetically modifying the host to be deficient of one or more genes encoding proteins that are involved in competitive lipid metabolism or utilize the same substrates as the key enzymes of the host's lipid synthesis pathway. Competitive metabolism can refer to production of unwanted metabolites or other products in the cell or indirectly by consuming substrates or energy needed in the lipid synthesis. The increase or improvement can be achieved by making a gene in the host deficient. This can be made by any gene modification resulting in reduced production or activity of the gene. Typically this is made by gene inactivation, for example knocking out of a gene or genes. By making a specific gene(s) deficient leads to improvement of lipid production. This can be due to increase in biomass, blocking or silencing competitive metabolic reactions or pathways, activation of lipid production synthesis route, increase in growth rate, increase in substrate usage, blocking or silencing lipid degrading pathway or activity, redirecting the lipid production towards different lipid groups, or some unknown mechanism, or combination of those.

As described herein the gene modification resulting in reduced production or activity of a desired gene has been exemplified here by making deficient an *Acinetobacter baylyi* host, strain ADP1 and strain BP1.

"ACIADXXXX", such as ACIAD2177 means a gene in *A. baylyi* species, in strain ADP1. For example *A. baylyi* strain ADP1 has been made deficient of gene ACIAD2177. The modified strain lacking gene ACIAD2177 is called ACIAD2177. ACIAD numbers are identifiers that are systematically applied to every gene in the genome of *Acinetobacter* sp. ADP1. They are in sequential order on the genome.

In various embodiments of the invention the genes listed below may be made deficient in an *Acinetobacter* host. The functions of some specific gene deletions are discussed. However, the specific gene deficiencies may also have other functions and the combination of specific gene deficiencies may have several different functions.

Within the scope of the present invention are genes encoding a specific enzyme activity. Within the scope of the present invention are also functional equivalents of the genes. A functional equivalent of a gene in an *Acinetobacter* host refers here to any nucleotide sequence causing when expressed in the host the same or equivalent function as the mentioned gene. A functional equivalent refers to a fragment, a gene having different nucleotide sequence or encoding different amino acid sequence, or the closest homologue in an *Acinetobacter* host, i.e. in another *Acinetobacter* species or in another *Acinetobacter baylyi* strain.

A gene encoding fatty acyl-CoA reductase means any gene in an *Acinetobacter* host encoding fatty acyl-CoA reductase having according to the Enzyme Classification the EC number EC1.2.1.n2. In a specific embodiment the gene is ACIAD 3383 (nucleotide sequence SEQ ID NO:1, encoded amino acid sequence SEQ ID NO:15), or a functional equivalent thereof in an *Acinetobacter* host. In some embodiments of the invention the inactivation or other deficiency of this gene increases TAG production as a competitive reaction is blocked. It is assumed that the gene ACIAD3383 is involved in converting the fatty acid chain to aldehyde which is further esterified with alcohol molecule. Thus, inactivation or other deficiency of the gene blocks the wax ester synthesis pathway. The ACIAD3383 knock-out strain possibly contains free long chain fatty acids.

A gene encoding lipase means any gene in an *Acinetobacter* host encoding lipase having according to the Enzyme Classification the EC number EC:3.1.1.3. In a specific embodiment of the invention the gene is ACIAD 3309 (nucleotide sequence SEQ ID NO:2, encoded amino acid sequence SEQ ID NO:16), or a functional equivalent thereof in an *Acinetobacter* host. The gene is annotated as TAG lipase but for unknown reason in various embodiments inactivation or other deficiency of the gene improves wax ester production. Without binding to any theory the lipase may possess activity on wax esters, thus preventing the mutant strain to degrade wax esters. In addition, inactivation or other deficiency of TAG lipase may inhibit the lipid degradation in long cultivations and downstream processing.

A gene encoding pyruvate dehydrogenase means any gene in an *Acinetobacter* host encoding pyruvate dehydrogenase having according to the Enzyme Classification the EC number (EC:1.2.2.2). In a specific embodiment the gene is ACIAD 3381 (nucleotide sequence SEQ ID NO:3, encoded amino acid sequence SEQ ID NO:17), or a functional equivalent thereof in an *Acinetobacter* host. In various embodiments of the invention inactivation or other deficiency of this gene blocks the synthesis of acetate as an over-flow metabolite, re-directing the carbon flow towards wax ester synthesis. The inactivation or other deficiency of this gene also increases and accelerates biomass production.

In a specific embodiment the gene is ACIAD 2177 (nucleotide sequence SEQ ID NO:4, amino acid sequence SEQ ID NO:18), or a functional equivalent thereof in an *Acinetobacter* host. The gene deficiency causes in some embodiments of the invention enhanced lipid production, although the function mechanism is not known.

A gene encoding diacylglycerol kinase means any gene in an *Acinetobacter* host encoding diacylglycerol kinase having according to the Enzyme Classification the EC number EC:2.7.1.107. In a specific embodiment the gene is ACIAD 2837 (nucleotide sequence SEQ ID NO:5, amino acid sequence SEQ ID NO:19), or a functional equivalent thereof in an *Acinetobacter* host. The corresponding protein (dgkA, diacylglycerol kinase) directs 1,2-diaclyglycerol to phospholipid synthesis. In some embodiments of the invention inactivation or other deficiency of the gene may prevent an accumulation of unwanted lipids in the cell.

A gene encoding succinate dehydrogenase means any gene in an *Acinetobacter* host encoding succinate dehydrogenase having according to the Enzyme Classification the EC number EC:1.3.5.1. In a specific embodiment the gene is ACIAD 2880 (nucleotide sequence SEQ ID NO:6, amino acid sequence SEQ ID NO:20), or a functional equivalent thereof in an *Acinetobacter* host. In various embodiments of the invention inactivation or other deficiency of the gene in a host may increase the amount of glycerol in the cell, which is needed for acylglycerol, such as TAG, synthesis.

A gene encoding glycerol-3-phosphate dehydrogenase means any gene in an *Acinetobacter* host encoding glycerol-3-phosphate dehydrogenase having according to the Enzyme Classification the EC number EC 1.1.5.3. In a specific embodiment the gene is ACIAD 2844 (nucleotide sequence SEQ ID NO:7, encoded amino acid sequence SEQ ID NO:21), or a functional equivalent thereof in an *Acinetobacter* host. In some embodiments of the invention gene ACIAD2844 has similar function as ACIAD2880.

A gene encoding cytochrome o ubiquinol oxidase subunit II means any gene in an *Acinetobacter* host encoding cytochrome o ubiquinol oxidase subunit II having according to the Enzyme Classification the EC number EC:1.10.3.-. In a specific embodiment of the invention the gene is ACIAD 2425 (nucleotide sequence SEQ ID NO:8, encoded amino acid sequence SEQ ID NO:22) or a functional equivalent thereof in an *Acinetobacter* host. In some embodiments of the invention the gene deficiency causes enhanced lipid production. The advantages obtained by inactivation or other deficiency of the gene may be based on increased production of acetyl-CoA for fatty acid synthesis. The advantages are considered to be similar as in strain being deficient of ACIAD2426 or ACIAD2291.

A gene encoding cytochrome o ubiquinol oxidase subunit I means any gene in an *Acinetobacter* host encoding cytochrome o ubiquinol oxidase subunit I having according to the Enzyme Classification the EC number EC:1.10.3.-. In a specific embodiment the gene is ACIAD 2426 (nucleotide sequence SEQ ID NO:9, encoded amino acid sequence SEQ ID NO:23), or a functional equivalent thereof in an *Acinetobacter* host. The advantages of the deficiency of the gene are considered to be similar as in strain being deficient of ACIAD2425 or ACIAD2291.

A gene encoding cytochrome d terminal oxidase polypeptide subunit II means any gene in an *Acinetobacter* host encoding cytochrome d terminal oxidase polypeptide subunit II having according to the Enzyme Classification the EC number EC1.10.3.-. In a specific embodiment the gene is ACIAD 2291 (nucleotide sequence SEQ ID NO:10, encoded amino acid sequence SEQ ID NO:24), or a functional equivalent thereof in an *Acinetobacter* host. The advantages are considered to be similar as in strain being deficient of ACIAD2425 or ACIAD2426.

A gene encoding carboxylesterase means any gene in an *Acinetobacter* host encoding carboxylesterase having according to Enzyme Classification the EC number EC:3.1.1.1. In a specific embodiment the gene is ACIAD 3648 (nucleotide sequence SEQ ID NO:11, encoded amino acid sequence SEQ ID NO:25), or a functional equivalent thereof in an *Acinetobacter* host. In some embodiments of the invention the inactivation or other deficiency of the gene prevents wax ester degradation in the cell. The protein encoded by the gene is annotated as esterase (wax ester lipase).

A gene encoding esterase means any gene in an *Acinetobacter* host encoding esterase. In a specific embodiment the gene is ACIAD 1134 (nucleotide sequence SEQ ID NO:12, encoded amino acid sequence SEQ ID NO:26), or a functional equivalent thereof in an *Acinetobacter* host. In some embodiments of the invention the gene deficiency prevents lipid degradation in the cell.

A gene encoding lipase means any gene in an *Acinetobacter* host encoding lipase having according to the Enzyme Classification the EC number EC:3.1.1.3. In a specific embodiment the gene is ACIAD 1121 (nucleotide sequence SEQ ID NO:13, encoded amino acid sequence SEQ ID NO:27); or a functional equivalent thereof in an *Acinetobacter* host s. In some embodiments of the invention the function is considered to be similar as of the deficiency of gene ACIAD1134.

A gene encoding acyl-CoA synthetase means any gene in an *Acinetobacter* host encoding acyl-CoA synthetase having according to the Enzyme Classification the EC number (EC: 6.2.1.3). In a specific embodiment the gene is ACIAD 0235 (nucleotide sequence SEQ ID NO:14, encoded amino acid sequence SEQ ID NO:28) or a functional equivalent thereof in an *Acinetobacter* host. In some embodiments of the invention the deficiency of the gene in a host inhibits competitive metabolism, in which the fatty acids are directed to degradation.

In some embodiments of the invention the following combinations of gene deficiency are of advantage:

In an embodiment an *Acinetobacter* host is made deficient of genes encoding pyruvate dehydrogenase (EC:1.2.2.2), fatty acyl-CoA reductase (EC1.2.1.n2) and lipase (EC: 3.1.1.3), for example a strain being deficient of genes ACIAD3381, ACIAD3383 and ACIAD3309 or a functional equivalent thereof in an *Acinetobacter* host. A preferred example of such strain is "Qm", the construction of which is described in the examples. The combination of the above gene deficiencies is expetted to increase both biomass and TAG compared to single gene deficiencies (ACIAD3381, ACIAD3383 or ACIAD3309). Deficiency of ACIAD3383 blocks the WE synthesis (competitive reaction pathway). As WE seems to be an over-flow metabolite for ACIAD3381 and potentially also for ACIAD3309, the combination of these three deficiencies are assumed to force the cell to produce more TAG. In addition, making deficient the ACIAD3381 potentially prevents the synthesis of acetate. Making deficient TAG lipase is expected to inhibit the lipid degradation in long cultivations and downstream processing.

In an embodiment an *Acinetobacter* host is made deficient of genes encoding pyruvate dehydrogenase (EC:1.2.2.2), fatty acyl-CoA reductase (EC1.2.1.n2) and diacylglycerol kinase (EC:2.7.1.107), for example a strain being deficient of genes ACIAD3381, ACIAD3383 and ACIAD2837, or a functional equivalent thereof in an *Acinetobacter* host. These gene deficiencies have same expected outcomes as the above described gene deficiencies exemplified by srain "Qm". Instead of the gene deficiency ACIAD3309, the strain is made deficient of gene ACIAD2837, which inhibits unwanted lipids to accumulate in the cell.

In an embodiment an *Acinetobacter* host is made deficient of genes encoding pyruvate dehydrogenase (EC:1.2.2.2), fatty acyl-CoA reductase (EC1.2.1.n2) and gene ACIAD2177, or a functional equivalent thereof in an *Acinetobacter* host, for example a strain being deficient of genes ACIAD3381, ACIAD3383 and ACIAD2177, or a functional equivalent thereof in an *Acinetobacter* host. These gene deficiencies have same expected outcomes as the above described gene deficiencies exemplified in strain Qm. Instead of the gene deficiency ACIAD3309, the strain is made deficient of gene ACIAD2177, which which has been experimentally shown to improve lipid production.

In an embodiment an *Acinetobacter* host is made deficient of genes encoding pyruvate dehydrogenase (EC:1.2.2.2), lipase (EC:3.1.1.3) and/or carboxyl esterase, for example a strain being deficient of genes ACIAD3381, ACIAD3309 and/or ACIAD3648, or a functional equivalent thereof in an *Acinetobacter* host. The combination of the gene deficiencies increases in some embodiments both biomass and wax ester production. As WE seems to be an over-flow metabolite for ACIAD3381 and potentially also for ACIAD3309, the combination of these two deletions may force the cell to produce more WE. In addition, making deficient the gene ACIAD3381 potentially prevents the synthesis of acetate. Deficiency of lipases inhibits the lipid degradation in long cultivations and downstream processing.

Within the scope of the present invention are also functional equivalents of the genes in an *Acinetobacter* host i.e. other nucleotide sequences of the described genes comprising shorter forms of said genes, or nucleotide sequences having deletions, substitutions, insertions or other modifications compared to the described genes or the closest homologues of the genes in an *Acinetobacter* host, but having the same or equivalent function as the described genes.

When searching for genes corresponding to the described genes of *A. baylyi* ADP1 in other *Acinetobacter* strains or species, it is evident that the corresponding genes may have small variations in the nucleotide sequence, but that such small variations in the nucleotide sequence of a gene do not significantly change the catalytic properties of the encoded protein. Also the deficiency of said genes is likely to cause the same or similar effect as the deficiency of the described genes in *A. baylyi* ADP1. For example many changes in the nucleotide sequence do not change the amino acid sequence of the encoded protein. Also an amino acid sequence may have variations, which do not change the functional properties of a protein, in particular they do not prevent an enzyme from carrying out its catalytic function. Such variations in the nucleotide sequence or DNA molecules or in an amino acid sequence are known as "functional equivalents", because they do not significantly change the function of the gene to encode a protein with a particular function, e.g. catalyzing a particular reaction or, respectively, change the particular function of the protein. The deficiency of genes being functional equivalents of the described genes causes equivalent effects to the *Acinetobacter* host in question as the deficiency of the described genes in *A. baylyi* ADP1. Within the scope of the present invention are functional equivalents, including fragments or other modifications, or closest homologues of the above listed genes, in particular functional equivalents of nucleotide sequences SEQ ID NO: 1 to 14, or amino acid sequences SEQ ID NO: 15 to 28.

Within the scope of the present invention are genes showing at least 50%, preferably at least 60% identity, preferably at least 65%, preferably at least 70%, preferably at least 75%, preferably at least 80%, preferably at least 85%, more preferably at least 90%, still more preferably at least 95%, more and more preferably at least 98% identity to any of the nucleotide sequences SEQ ID NO: 1 to 14.

Within the scope of the present invention are genes encoding amino acid sequences showing at least 50%, preferably at least 60% identity, preferably at least 65%, preferably at least 70%, preferably at least 75%, preferably at least 80%, preferably at least 85%, more preferably at least 90%, still more preferably at least 95%, more and more preferably at least 98% identity to any of the amino acid sequences SEQ ID NO: 15 to 28.

Within the scope of the present invention are genes comprising any of the nucleotide sequences SEQ ID NO:1 to 14.

Within the scope of the present invention are genes encoding proteins comprising any of the amino acid sequences SEQ ID NO:15 to 28.

The term "identity" refers to the identity between two nucleic acid or amino acid sequences, respectively compared to each other from the first nucleic acid to the last nucleic acid or from the first amino acid encoded by the corresponding gene to the last amino acid. The identity of the full-length sequences can be measured by using BLAST program (Altschul, S. F., T. L. Madden, A. A. Schäffer, J. Zhang, Z. Zhang, W. Miller and D. J. Lipman 1997. Gapped BLAST and PSI-BLAST: a new generation of protein database search programs. Nucleic Acids Res. 25:3389-3402). In the comparison is preferably used nucleotide sequence without signal sequence or the mature sequences of the proteins.

Within the scope of the present invention are also the closest homologues of the genes in other *Acinetobacter* species or strains. The "closest homologue of an *Acinetobacter* gene" in other species or strains means here a gene that has the highest percentage of identical nucleotides with the *Acinetobacter* gene of all the genes of the organism; or a gene whose protein product has the highest percentage of identical amino acids with the protein product encoded by the *Acinetobacter* gene of all the gene products of the organism. The nucleotide or amino acid sequences may be aligned and the percentage of sequence identity in the aligned sequences can be used as a measure to identify the closest homologue of the gene in the other organism. This can be done by using public databases and tools, for example BLAST search.

Within the scope of the present invention are also functional equivalents of said genes hybridizing under stringent conditions to said genes or said homologues. The hybridization is preferably carried out under stringent hybridization conditions. Stringent conditions can be defined as hybridization at 65° C. in a low salt concentration, 1.5 mM sodium citrate, pH 7.0 and 0.015 NaCl, according to Boehringer Mannheim's manual, DIG System User's Guide for Filter hybridization.

The deficiency of gene(s) leading to improvement of lipid production can be due to increase in biomass, blocking or silencing competitive metabolic reactions or pathways, activation of lipid production synthesis route, increase in growth rate, increase in substrate usage, blocking or silencing lipid degrading pathway or activity, redirecting the lipid production towards different lipid groups, or some unknown mechanism, or combination of those.

As disclosed herein some embodiments of the invention have been exemplified by constructing and verifying the following gene deficiency combinations: ACIAD(3381, 3383, 3309), ACIAD(3383, 2880), ACIAD(2177, 3381, 3383), ACIAD(2837, 3381, 3383).

In various embodiments of the invention one or more of the following genes or functional equivalents thereof can be made deficient in an *Acinetobacter* host: ACIAD3381, ACIAD3309, ACIAD2837, ACIAD2177, ACIAD3383, ACIAD2880, ACIAD2844, ACIAD2425, ACIAD2426, ACIAD2291, ACIAD3648, ACIAD1121, ACIAD1134 or ACIAD0235, in combination with one or more of the following genes ACIAD3381, ACIAD3309, ACIAD2837, ACIAD2177, ACIAD3383, ACIAD2880, ACIAD2844, ACIAD2425, ACIAD2426, ACIAD2291, ACIAD3648, ACIAD1121, ACIAD1134, ACIAD0235 or a functional equivalent of said genes in an *Acinetobacter* host. In Table 1 has been listed the genes made deficient in an *Acinetobacter* host and the assumed function causing the effects to the lipid metabolism.

TABLE 1

Gene deficiencies related to lipid metabolism and their hypothetic functions.

| gene ID | Gene name | Product | EC | working hypotheses | Group |
|---|---|---|---|---|---|
| ACIAD2837 | dgkA | diacylglycerol kinase | EC 2.7.1.107 | directs 1,2-diacylglycerol (substrate for WS/GDAT) to phospholipid synthesis | competitive metabolism |

TABLE 1-continued

Gene deficiencies related to lipid metabolism and their hypothetic functions.

| gene ID | Gene name | Product | EC | working hypotheses | Group |
|---------|-----------|---------|-----|--------------------|-------|
| ACIAD3383 | acr1 | fatty acyl-CoA reductase (hexadecanal dehydrogenase, acylating) | EC 1.2.1.n2 | converts fatty acid to aldehyde; in absence of 3383 wax esters are not formed | competitive metabolism |
| ACIAD2880 | sdhA | succinate dehydrogenase, flavoprotein subunit | EC 1.3.5.1 | takes part in citric acid cycle; in absence of 2880, more free glycerol is in the cell? | glycerol metabolism |
| ACIAD2844 | glpD | glycerol-3-phosphate dehydrogenase | EC 1.1.5.3 | in absence, more glycerol for WS and/or DGAT? | glycerol metabolism |
| ACIAD2425 | cyoA | cytochrome o ubiquinol oxidase subunit II | EC 1.10.3.- | not clear | other |
| ACIAD2426 | cyoB | cytochrome o ubiquinol oxidase subunit I | EC 1.10.3.- | not clear | other |
| ACIAD2291 | cydB | cytochrome d terminal oxidase polypeptide subunit II | EC 1.10.3.- | not clear | other |
| ACIAD3381 | poxB | pyruvate dehydrogenase (cytochrome) | EC 1.2.2.2 | acetate production; in absence of 3381, significantly more WE is formed | enhanced WE production |
| ACIAD3648 | estA | carboxylesterase (ALI-esterase) (B-esterase) (MONOBUTYRASE) (Cocaine esterase) (PROCAINE esterase) (METHYLBUTYRASE) | EC 3.1.1.1 | esterase, lipase for WE | lipase + enhanced WE production |
| ACIAD1134 | aesT | esterase | ? | esterase, lipase for WE | lipase |
| ACIAD3309 | — | lipase | EC 3.1.1.3 | TAG lipase, in absence also more WE are produced | lipase + enhanced WE production |
| ACIAD1121 | lip1 | lipase | EC:3.1.1.3 | lipase | lipase |
| ACIAD0235 | fadD | acyl-CoA synthetase (long-chain-fatty-acid-CoA ligase) | EC 6.2.1.3 | rasvahappojen ohjaus hajotukseen | competitive metabolism |
| ACIAD2177 | — | conserved hypothetical protein | ? | not clear | enhanced lipid production |

In one still further embodiment of the invention the *Acinetobacter* host may be genetically modified to express one or more genes encoding the enzymes of lipid biosynthesis pathway with or without making the host deficient in one or more of the genes described in Table 1 or functional equivalents thereof. The gene may be endogenous or exogenous to the *Acinetobacter* host.

The term "endogenous gene" refers here to a gene which is natural to an *Acinetobacter* host.

The term "exogenous gene" refers here to a gene which is not natural to an *Acinetobacter* host.

"Genetical modification" of an *Acinetobacter* host means here any genetic modification method by which an *Acinetobacter* host is modified to express a specific endogenous or exogenous gene and/or to be deficient of a specific gene or genes. Genetical modification methods for an *Actinetobacter* host are available and well known for a person skilled in the art and disclosed for example in Metzger et al. 2004.

In one still further embodiment of the invention the host may be genetically modified to express a gene encoding diacylglyserol synthase enzyme and/or to overexpress a gene encoding wax ester synthase and/or acyl-CoA:diacylglycerol acyltransferase (WS and/or DGAT).

In one embodiment of the invention the WE/TAG synthesis of *Acinetobacter* may be made more efficient to the direction of TAG production. This can be achieved by expressing a gene producing TAG or a similar kind of gene having TAG synthesizing activity, but which lacks WE synthesizing activity. Suitable gene for directing the lipid synthesis towards TAG production in *Acinetobacter* host is a gene encoding diacylglycerol acyltransferase (DGAT) (EC 2.3.1.20).

A gene encoding acylglycerol synthase enzyme (EC 2.3.1.20) is typically an exogenous gene to an *Acinetobacter* host. Preferably it originates from a *Streptomyces* bacterium. For example in *Streptomyces coelicolor* gene sco0958 encodes TAG producing activity, but not WE producing activity. The gene sco0958 (gene ID number 101096381) catalyzes the ultimate step in the biosynthesis of TAGs (Arabolaza et al., 2008). As herein described the effect of a gene encoding acylglyserol synthase enzyme has been exemplified by using a codon-optimized synthetic gene (raSVa) (SEQ ID NO:29) encoding amino acid sequence analogous to sco0958 from *Streptomyces coelicolor* (SEQ ID NO:30).

A gene encoding WS/DGAT typically originates from the same or another *Acinetobacter* species as the *Acinetobacter* host to be modified. *Acinetobacter* genus bacteria produce storage lipids in the form of TAGs and wax esters (WE) by using an enzyme which has both TAG and WE activity. For example in *A. baylyi* the enzyme WS/DGAT, bifunctional wax ester synthase/acyl coenzyme A: diacylglycerol acyltransferase, EC 2.3.1.75 and EC 2.3.1.20 is encoded by gene aftA (SEQ ID NO:31) and comprise the amino acid sequence (SEQ ID NO:32). The enzyme possesses both acyl-CoA:fatty alcohol acyltransferase (wax ester synthase, WS) activity and acyl-CoA:diacylglycerol acyltransferase (DGAT) activity. In some embodiments of the invention a genetically modified nucleotide sequence encodes either or both activities, WS and/or DGAT.

It is evident that small variations in the nucleotide sequence of a gene do not significantly change the catalytic properties of the encoded protein. For example many changes in the nucleotide sequence do not change the amino acid sequence of the encoded protein. Also an amino acid sequence may have variations, which do not change the functional properties of a protein, in particular they do not prevent an enzyme from carrying out its catalytic function. Such variations in the nucleotide sequence or DNA molecules or in an amino acid sequence are known as "functional equivalents", because they do not significantly change the function of the gene to encode a protein with a particular function, e.g. catalyzing a particular reaction or, respectively, change the particular function of the protein. Within the scope of the present invention are functional equivalents, including fragments, derivatives, genes having different nucleotide sequence or encoding different amino acid sequence, modified forms or closest homologues of the nucleotide sequence SEQ ID NO:29 or SEQ ID NO:31, or of the amino acid sequence SEQ ID NO: 30 or SEQ ID NO:32.

Within the scope of the present invention are also a nucleotide sequence showing at least 60% identity, preferably at least 65%, preferably at least 70%, preferably at least 75%, preferably at least 80%, preferably at least 85%, more preferably at least 90%, still more preferably at least 95%, more and more preferably at least 98% identity to nucleotide sequence SEQ ID NO:29 or SEQ ID NO:31.

Within the scope of the present invention are also a nucleotide sequence encoding an amino acid sequence showing at least 60% identity, preferably at least 65%, preferably at least 70%, preferably at least 75%, preferably at least 80%, preferably at least 85%, more preferably at least 90%, still more preferably at least 95%, more and more preferably at least 98% identity to amino acid sequence SEQ ID NO:30 or SEQ ID NO:32.

The term "identity" refers to the identity between two nucleic acid or amino acid sequences, respectively compared to each other from the first nucleic acid to the last nucleic acid or from the first amino acid encoded by the corresponding gene to the last amino acid. The identity of the full-length sequences can be measured by using Needleman-Wunsch global alignment program at EMBOSS program package (European Molecular Biology Open Software Suite; Rice et al., 2000) Alternatively, or in addition, identity can be measured by ClustalW-software. In the comparison is preferably used the nucleotide sequences without signal sequence or mature sequences of the proteins without signal sequence.

Within the scope of the present invention are nucleotide sequences causing the same function or equivalent function as said genes sco0958 (SEQ ID NO:29) or aftA (SEQ ID NO:31). Such nucleotide sequences are fragments, derivatives, genes having different nucleotide sequence or encoding different amino acid sequence, modified forms of said genes, the closest homologues of said genes in various *Streptomyces* species (as regards to sco0958) or in various *Acinetobacter* species (as regards to aftA), or nucleotide sequences which hybridize to at least one of said genes or said homologues.

The hybridization is preferably carried out under stringent hybridization conditions. Stringent conditions can be defined as hybridization at 65° C. in a low salt concentration, 1.5 mM sodium citrate, pH 7.0 and 0.015 NaCl, according to Boehringer Mannheim's manual, DIG System User's Guide for Filter hybridization.

Within the scope of the present invention are also the closest homologues of the genes in other *Streptomyces* (as regards to sco0958) or *Acinetobacter* (as regards to aftA) species or strains. The "closest homologue of a *Streptomyces*" or "an *Acinetobacter* gene" in other species or strains means here a gene that has the highest percentage of identical nucleotides with the *Streptomyces* or *Acinetobacter* gene, respectively, of all the genes of the organism; or a gene whose protein product has the highest percentage of identical amino acids with the protein product encoded by the *Streptomyces* or *Acinetobacter* gene of all the gene products of the organism. The nucleotide or amino acid sequences may be aligned and the percentage of sequence identity in the aligned sequences can be used as a measure to identify the closest homologue of the gene in the other organism. This can be done by using public databases and tools; for example BLAST search.

Micro-organisms capable of producing enzymes involved in lipid biosynthesis can be screened, the activity on various substrates can be determined, and the enzyme characterized. Nucleotide sequences encoding enzymes involved in lipid biosynthesis in various organisms can be isolated and the nucleotide sequences can be compared with the nucleotide sequences SEQ ID NO: 29 or SEQ ID NO:31 and the amino acid sequences can be compared with the amino acid sequences SEQ ID NO: 30 or SEQ ID NO:32. A person skilled in the art can also identify a conserved region in the nucleotide or amino acid sequence and clone a gene fragment using for example PCR techniques. After sequencing the fragment the complete gene can be obtained for example by using cDNA library in a vector. A nucleotide sequence encoding the enzyme can be identified also by nucleic acid hybridization.

Standard molecular biology methods can be used in the cloning of the genes i.e. in the isolation and enzyme treatments of DNA, in *E. coli* transformations, the isolation of a fragment comprising the gene by amplification in a PCR reaction (Coen D M, 2001) and in the techniques for codon change. The basic methods used are described in the standard molecular biology handbooks, e.g. Sambrook et al. (1990) and Sambrook and Russell (2001). Insertion of the nucleotide sequence under a strong promoter in an expression vector, transfer of the vector into suitable host cells and cultivation of the host cells in conditions provoking production of said enzyme. Methods for protein production by recombinant technology in different host systems are well known in the art (Gellissen, 2005).

Within the scope of the present invention is any gene, that has the same or equivalent effect as the above described genes. Within the scope of the present invention are also genes, which are highly homologous to the genes of interest. The gene introduced to *Acinetobacter* may encode *Acinetobacter* diacylglycerol synthase enzyme or a homologous enzyme or an enzyme having the equivalent function. The gene introduced to *Acinetobacter* may encode *Acinetobacter* WS and/or DGAT enzyme or a homologous enzyme or an enzyme having the equivalent function.

A gene encoding an enzyme producing TAG or WE or both can be linked to a part of an expression system functioning in an *Acinetobacter* host and it can be transferred to the cell with a gene technology method or by using the natural transformation capability of *Acinetobacter*. The gene encoding an enzyme producing TAG or WE or both can originate from a known organism or it can originate from a yet unknown organism, for example metagenomic library.

In addition to modifying an *Acinetobacter* host to express or overexpress specific gene(s), the host may be genetically modified to be deficient of specific gene(s). The genetic modifications may be made in any suitable order or at the same time. Typically the host is first made deficient of specific genes and after that other desired genes are introduced to the host cell. By various genetic modification the WE/TAG ratio and/or amount can be changed.

The effect of expression or overexpression of a gene on lipid production can be studied by culturing the modified host under conditions suitable for lipid production.

Genetically modifying an *Acinetobacter* host to express an endogenous or exogenous gene can be carried out for example by introducing into an *Acinetobacter* host an exogenous gene or an additional copy or copies of an endogenous gene. The gene may be expressed under a promoter recognized by the *Acinetobacter* host. In some embodiments the gene may be expressed under another promoter resulting in increased expression of the gene. Alternatively the *Acinetobacter* host may be genetically modified so that either the gene is more abundantly expressed or that the activity of the gene product is increased.

"Regulatory elements" refer to regulatory elements which can regulate the expression of a gene introduced into a host cell, here in particular into *Acinetobacter*. Regulatory elements include promoters, terminators, enhancers and signal sequences.

"Expression" or "overexpression of a gene" refers here in particular to a gene of the lipid biosynthesis pathway. A desired gene can be introduced into an *Acinetobacter* host as an additional copy or copies of a specific gene, or expressing the gene under another promoter resulting in increased expression of the gene, or otherwise genetically modifying the host so that either the gene is more abundantly expressed or the activity of the gene product is increased.

The genes have been numbered and named according to *A. baylyi* strain ADP1, and they can have different names in different *Acinetobacter* species and strains. The genes have the same or partly the same function in different *Acinetobacter* species and strains. The function can be predicted based for example on sequence data.

Genetic engineering of *Acinetobacter* hosts, exemplified here by *A. baylyi* species host can be done by exploiting the capability of the host to undergo natural trans-formation and homologous recombination. In natural transformation DNA molecule is brought into cells through membranes by mechanism, which is regulated by specific competence genes of the host. Of the genus *Acinetobacter*, the strains of *A. baylyi* (ADP1, $B2^T$, 93A2, A7, and C5) are naturally transformable. The competence can be induced by transferring cells of stationary growth phase to fresh media; it has been shown that the competence for natural transformation in ADP1 is developed immediately after the start of exponential growth phase and lasts until the stationary growth phase. For example, if the DNA fragment (linear or circular) to be transformed contains flanking regions of a specific target gene of the host, the gene will be replaced (i.e. knocked-out) with the DNA fragment. The target gene can be also inactivated by gene knock-down. Knockdown refers to techniques by which the expression of genes is reduced via genetic modification (a change in the genome) or treatment with a reagent such as a short DNA or RNA with a capacity to specifically bind to a transcript or a gene of interest. After incubation of 1-12 h, the cells can be selected on a plate containing appropriate selection agent, such as antibiotic.

Alternatively, Red/ET recombineering can be applied for making gene knockouts, as the method is not restricted to naturally competent bacteria. The method is most commonly used to generate simple gene replacements, substituting a drug marker in place of the gene of interest. In Red/ET recombineering, a generated PCR product contains a drug marker flanked by ~40 bp of target sequence. The PCR product is purified and electroporated into the host containing the λ Red+Gam (or RecET+λ Gam) recombination system (from bacteriophage). After growing the cells for 1-2 hours, the culture is plated on antibiotic-selection media for growth of the drug resistant transformant. The gene replacement can be verified phenotypically, or by a PCR using primers upstream, downstream, or within the drug marker. For example, this technology has been used to generate a gene knockout in every nonessential gene in the *E. coli* chromosome.

For genetic engineering of prokaryotes, also commercial kits are available (for example Targe Tron, Sigma).

Recovery of Lipids

In various embodiments of the invention, lipids, can be recovered from *Acinetobacter* cell biomass or culture broth using any method known in the art or developed in the future. For example, bacteria are separated from the medium using a filtration or decanting techniques. Alternately, centrifugation with industrial scale commercial centrifuges of large volume capacity are used to separate the desired products.

In some embodiments of the invention, bacterial cells are disrupted to facilitate the separation of lipids and other components. Any method known for cell disruption may be used, such as ultrasonication, osmotic shock, mechanical shear force, cold press, thermal shock, enzyme-catalyzed or self-directed autolysis. Lipids can be recovered from cells by extraction with organic solvents or by any method known in the art or developed in the future.

The strains, methods, cultivation conditions, ingredients for fermentation and the process as disclosed and claimed herein concern technology that supports large scale and economical cultivation of *Acinetobacter* bacteria. This technology is useful to support industrial manufacturing of lipids by *Acinetobacter* bacteria.

Production of Biofuel

The lipids produced with the method described in this invention can be used as a raw material or as a component in the raw material for the production of biofuel, in particular biodiesel, renewable diesel, jet fuel or gasoline. Biodiesel consists of fatty acid alkyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogen deoxygenation, hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications. Lipids can be also used as a component of biofuel. Further, lipids can be mixed with fossil fuels and co-processed to produce transportation fuels with bio-content or biocomponents.

The *Acinetobacter* lipids are beneficial for the production of biofuel. Further, the main fatty chain lengths are mainly from C12 (12 carbons) to C18 (18 carbons), which is advantageous for the utilization in diesel applications. The lipids in *Acinetobacter* are rather saturated (fatty acids contain low amount of double bonds). The fatty acid saturation is advantageous especially for renewable diesel production since it reduces the amount of hydrogen in hydrogen treatment, and therefore lowers the production (operation) cost.

*Acinetobacter* hosts showing suitable properties for industrial useful fermentation processes, in particular for biofuel production, can be further improved by any known strain improvement methods, such as natural selection, random mutagenization, and by genetic engineering. In addition, for industrial use are chosen species and strains which are non-pathogenic and non-virulent to human or animals.

In summary, various embodiments of the invention are described below with the aid of the following numbered clauses 1-21:

1. A genetically modified *Acinetobacter* host for lipid production, which comprises that the *Acinetobacter* host has been genetically modified to be deficient of one or more genes of group A or of group B or one or more genes of both groups, wherein group A comprises a gene encoding fatty acyl-CoA reductase (EC1.2.1.n2), gene ACIAD 3383 (SEQ ID NO:1) or a functional equivalent thereof in an *Acinetobacter* host, wherein said host is capable of increased production of TAGs and/or of total lipids compared to the parent host; and group B comprises a gene encoding lipase (EC:3.1.1.3), gene ACIAD 3309 (SEQ ID NO: 2) or a functional equivalent thereof in an *Acinetobacter* host, a gene encoding pyruvate dehydrogenase (EC:1.2.2.2), gene ACIAD 3381 (SEQ ID NO:3) or a functional equivalent thereof in an *Acinetobacter* host and/or gene ACIAD 2177 (SEQ ID NO:4) or a functional equivalent thereof in an *Acinetobacter* host, wherein said host is capable of increased production of wax esters and/or total lipids compared to the parent host.

2. The host according to clause 1, wherein the host has been made deficient of one or more genes of group A or of group B or one or more genes of both groups, wherein group A comprises ACIAD3383, and group B comprises ACIAD3309, ACIAD3381 and/or ACIAD2177, or a functional equivalent of said genes in an *Acinetobacter*.

3. The host according to clause 1, wherein the host has been made deficient of

A) a gene encoding fatty acyl-CoA reductase (EC1.2.1.n2), gene ACIAD 3383 (SEQ ID NO:1) or a functional, equivalent thereof in an *Acinetobacter* host, one or more of B) a gene encoding diacylglycerol kinase (EC:2.7.1.107), gene ACIAD 2837 (SEQ ID NO:5) or a functional equivalent thereof in an *Acinetobacter* host; a gene encoding succinate dehydrogenase (EC:1.3.5.1), gene ACIAD 2880 (SEQ ID NO:6) or a functional equivalent thereof in an *Acinetobacter* host; a gene encoding glycerol-3-phosphate dehydrogenase (EC 1.1.5.3), gene ACIAD 2844 (SEQ ID NO:7) or a functional equivalent thereof in an *Acinetobacter* host, a gene encoding cytochrome o ubiquinol oxidase subunit II (EC:1.10.3.-), gene ACIAD 2425 (SEQ ID NO:8) or a functional equivalent thereof in an *Acinetobacter* host a gene encoding cytochrome o ubiquinol oxidase subunit I (EC:1.10.3.-), gene ACIAD 2426 (SEQ ID NO:9), or a functional equivalent thereof in an *Acinetobacter* host; a gene encoding cytochrome d terminal oxidase polypeptide subunit II (EC1.10.3.-), gene ACIAD 2291 (SEQ ID NO:10), or a functional equivalent thereof in an *Acinetobacter* host; a gene encoding pyruvate dehydrogenase (EC:1.2.2.2), gene ACIAD 3381 (SEQ ID NO:3), or a functional equivalent thereof in an *Acinetobacter* host; a gene encoding carboxylesterase (EC:3.1.1.1), gene ACIAD 3648 (SEQ ID NO:11), or a functional equivalent thereof in an *Acinetobacter* host; a gene encoding esterase, gene ACIAD 1134 (SEQ ID NO:12), or a functional equivalent thereof in an *Acinetobacter* host; a gene encoding lipase (EC:3.1.1.3), gene ACIAD 3309 (SEQ ID NO:2) or a functional equivalent thereof in an *Acinetobacter* host, gene ACIAD 1121 (SEQ ID NO:13) or a functional equivalent thereof in an *Acinetobacter* host; a gene encoding acyl-CoA synthetase (EC:6.2.1.3), gene ACIAD 0235 (SEQ ID NO:14) or a functional equivalent thereof in an *Acinetobacter* host; or gene ACIAD 2177 (SEQ ID NO:4) or a functional equivalent thereof in an *Acinetobacter* host, wherein said host is capable of increased production of TAGs, wax esters and/or total lipids compared to the parent host.

4. The host according to clause 3, wherein the host has been made deficient of group A comprises ACIAD3383, and/or group B comprises ACIAD2837, ACIAD 2880, ACIAD2844, ACIAD2425, ACIAD2426, ACIAD2291, ACIAD3381, ACIAD3648, ACIAD1134, ACIAD3309, ACIAD1121, ACIAD 0235, or ACIAD2177, or a functional equivalent of said genes in an *Acinetobacter* host.

5. The host according to clause 1, wherein the host has been made deficient of

A) a gene encoding fatty acyl-CoA reductase (EC1.2.1.n2), gene ACIAD 3383 (SEQ ID NO:1) or a functional equivalent thereof in an *Acinetobacter* host, and/or one or more of B) a gene encoding cytochrome o ubiquinol oxidase subunit II (EC:1.10.3.-), gene ACIAD 2425 (SEQ ID NO:8) or a functional equivalent thereof in an *Acinetobacter* host, or a gene encoding succinate dehydrogenase (EC:1.3.5.1), gene ACIAD 2880 (SEQ ID NO:6), or a functional equivalent thereof in an *Acinetobacter* host, wherein said host is capable of increased production of TAGs, wax esters and/or of total lipids compared to the parent host.

6. The host according to clause 5, wherein the host has been made deficient of

A) ACIAD3383 and/or one or more of

B) ACIAD2425 or ACIAD2880, or a functional equivalent of said genes in an *Acinetobacter* host.

7. The host according to any one of clause 1, wherein the host has been made deficient of one or more of a gene encoding lipase (EC:3.1.1.3), gene ACIAD 3309 (SEQ ID NO:2) or a functional equivalent thereof in an *Acinetobacter* host, a gene encoding pyruvate dehydrogenase (EC: 1.2.2.2), gene ACIAD 3381 (SEQ ID NO:3) or a functional equivalent thereof in an *Acinetobacter* host and/or gene 2177 or a functional equivalent thereof in an *Acinetobacter* host, wherein said host is capable of increased production of WEs and/or total lipids.

7. The host according to clause 7, wherein the host has been made deficient of one or more of ACIAD 3309, ACIAD3381 and/or 2177, or a functional equivalent of said genes in an *Acinetobacter* host.

8. The host according to clause 7, wherein the host has been made deficient of a gene encoding lipase (EC:3.1.1.3), gene ACIAD 3309 (SEQ ID NO:2) or a functional equivalent thereof in an *Acinetobacter* host, alone or together with one or more of a gene encoding diacylglycerol kinase (EC:2.7.1.107), gene ACIAD 837 (SEQ ID NO:5) or a functional equivalent thereof in an *Acinetobacter* host; a gene encoding fatty acyl-CoA reductase (EC1.2.1.n2), gene ACIAD 3383 (SEQ ID NO:1), or a functional equivalent thereof in an *Acinetobacter* host; a gene ecoding succinate dehydrogenase (EC:1.3.5.1), gene ACIAD 2880 (SEQ ID NO:6) or a functional equivalent thereof in an *Acinetobacter* host; a gene encoding glycerol-3-phosphate dehydrogenase (EC 1.1.5.3), gene ACIAD 2844 (SEQ ID NO:7) or a functional equivalent thereof in an *Acinetobacter* host; a gene encoding cytochrome o ubiquinol oxidase subunit II (EC:

1.10.3.-), gene ACIAD 2425 (SEQ ID NO:8) or a functional equivalent thereof in an *Acinetobacter* host; a gene encoding cytochrome o ubiquinol oxidase subunit I (EC: 1.10.3.-), gene ACIAD 2426 (SEQ ID NO:9), or a functional equivalent thereof in an *Acinetobacter* host; a gene encoding cytochrome d terminal oxidase polypeptide subunit II (EC1.10.3.-), gene ACIAD 2291 (SEQ ID NO:10, or a functional equivalent thereof in an *Acinetobacter* host; a gene encoding pyruvate dehydrogenase (EC1.2.2.2), gene ACIAD 3381 (SEQ ID NO:3) or a functional equivalent thereof in an *Acinetobacter* host, a gene encoding carboxylesterase (EC:3.1.1.1), gene ACIAD 3648 (SEQ ID NO:11), or a functional equivalent thereof in an *Acinetobacter* host, a gene encoding esterase, gene ACIAD 1134 (SEQ ID NO:12), or a functional equivalent thereof in an *Acinetobacter* host, various lipases (EC:3.1.1.3), gene ACIAD 1121 (SEQ ID NO:13) or a functional equivalent thereof in an *Acinetobacter* host, or a gene encoding acyl-CoA synthetase (EC:6.2.1.3), gene ACIAD 0235 (SEQ ID NO:14) or a functional equivalent thereof in an *Acinetobacter* host, wherein said host is capable of increased production of WEs and/or of total lipids.

9. The host according to clause 8, wherein the host has been made deficient of one or more of ACIAD3309 alone or together with one or more of
ACIAD 2837, ACIAD3383, ACIAD 2880, ACIAD 2844, ACIAD2425, ACIAD2426, ACIAD 2291, ACIAD3381, ACIAD3648, ACIAD 1134, ACIAD1121, ACIAD0235 or ACIAD2177, or a functional equivalent of said genes in an *Acinetobacter* host s.

10. The host according to clause 7, wherein the host has been made deficient of
a gene encoding pyruvate dehydrogenase (EC:1.2.2.2), gene ACIAD 3381 (SEQ ID NO:3) or a functional equivalent thereof in an *Acinetobacter* host, alone or together with one or more of the genes as defined in clause 8.

11. The host according to clause 10, wherein the host has been made deficient of one or more of a gene encoding pyruvate dehydrogenase (EC:1.2.2.2), gene ACIAD 3381 (SEQ ID NO:3) or a functional equivalent thereof in an *Acinetobacter* host alone or together with one or more of the genes as defined in clause 8 or 9.

12. The host according to clause 7, wherein the host has been made deficient of
ACIAD 2177 or a functional equivalent thereof in an *Acinetobacter* host alone or together with one or more of the genes as defined in clause 8 or 9 wherein said host is capable of increased production of total lipids.

13. The host according to clause 12, wherein the host has been made deficient of one or more of ACIAD2177 alone or together with one or more of the genes as defined in clause 8 or 9.

14. The host according to any one of clauses 1 to 13, wherein the host been genetically modified to express one or more genes encoding the enzymes of lipid biosynthesis pathway.

15. The host according to any one of clauses 1 to 8, wherein the host been genetically modified to express a gene encoding diacylglycerol synthase enzyme (EC 2.3.1.20) or to express a gene encoding WS and/or DGAT bifunctional wax ester synthase/acyl coenzyme A:diacylglycerol acyltransferase, EC 2.3.1.75 and EC 2.3.1.20.

16. The host according to any one of clauses 1 to 15, wherein the host is genetically modified to express a gene selected from the group of
(a) sco0958 (SEQ ID NO: 29) or aftA (SEQ ID NO: 31);
(b) the closest homologue of sco0958 in a *Streptomyces* species, said homologue encoding diacyiglycerol synthase enzyme (EC 2.3.1.20) or the closest homologue of aftA in an *Acinetobacter* species, said homologue encoding WS and/or DGAT (bifunctional wax ester synthase/acyl coenzyme A:diacylglycerol acyltransferase, EC 2.3.1.75 and EC 2.3.1.20);
(c) a nucleotide sequence which hybridizes to SEQ ID NO: 29 or a homologue thereof under stringent hybridization conditions and encodes diacylglyserol synthase enzyme (EC 2.3.1.20) activity or a nucleotide sequence which hybridizes to SEQ ID NO: 31 or a homologue thereof under stringent hybridization conditions and encodes WS and/or DGAT (bifunctional wax ester synthase/acyl coenzyme A:diacylglycerol acyltransferase, EC 2.3.1.75 and EC 2.3.1.20); and
(d) a nucleotide sequence encoding the amino acid sequence SEQ ID NO:30, or a sequence having at least 60% identity to said sequence and having diacylglyserol synthase enzyme (EC 2.3.1.20), or a nucleotide sequence encoding the amino acid sequence SEQ ID NO:32 or a sequence having at least 60% identity to said sequence and having WS and/or DGAT (bifunctional wax ester synthase/acyl coenzyme A:diacylglycerol acyltransferase), EC 2.3.1.75 and EC 2.3.1.20 activity.

17. A method for genetically modifying an *Acinetobacter* host by making the host deficient of one or more genes as defined in any one of clauses 1 to 16 and optionally by introducing into said host in an operational manner one or more genes of the lipid biosynthesis pathway.

18. A process for producing lipids, which comprises
cultivating an *Acinetobacter* host of any one of clauses 1 to 16 under suitable cultivation conditions;
allowing *Acinetobacter* host to accumulate lipids; and recovering the lipids.

19. A lipid composition produced by the process of clause 18.

20. Use of the lipids produced according to clause 18 or lipid composition according to clause 19 as a component of biofuel or as a starting material for biofuel production.

21. A method for producing biofuel, which comprises
cultivating *Acinetobacter* host according to any one of clauses 1 to 16 under suitable cultivation conditions;
allowing *Acinetobacter* host to accumulate lipids
recovering the lipids,
producing biofuel using the recovered lipids as a component or as starting material for biofuel production.

EXAMPLES

Example 1

Improvement of Total Lipid Production

Strains

*Acinetobacter* baylyi ADP1 wild type, also referred as BD413, is available to the public at American Type Culture Collection (ATCC, Accession number 33305). The natural wild type strain B2 is available to the public at Deutsche Sammlung von Mikroorganismen und Zellkulturen GmbH (DSMZ, Accession number 14961). Single gene knock-out mutants lacking the gene in question are referred as the gene name ACIAD[number], for example ACIAD3381 means ADP1 strain lacking the gene ACIAD3381.

The widely studied laboratory strain ADP1 does not carry any virulence or pathogenicity factors. Furthermore, most of the antibiotics used with *E. coli* are also effective against ADP1. ADP1 has competence to undergo natural transformation via an efficient DNA uptake and homologous recombination.

Growth Conditions

ADP1 strains were cultivated in LB (10 g/l tryptone, 5 g/l yeast extract, 10 g/l NaCl, pH 7), M9 minimal medium (6 g/l $Na_2HPO_4$, 3 $KH_2PO_4$, 1 g/l $NH_4Cl$, 0.5 g/l NaCl, 2 mM $MgSO_4$, 0.1 mM $CaCl_2$) or MA/9 minimal medium (Table 2) supplemented with appropriate carbon source. In some experiments the media were supplemented with 0.2% casein amino acids, and/or yeast extract and appropriate antibiotics. Temperature was set to 30° C. and shaking for aeration to 300 rpm and glucose was used as a substrate if not stated otherwise. For plate cultivations, medium components were the same except 15 g/l agar was added to the medium before autoclaving. All the components were provided by Sigma (USA) if not stated otherwise.

TABLE 2

Medium components MA/9

| Component | /liter medium |
| --- | --- |
| $Na_2HPO_4 \cdot 2 H_2O$ | 5.518 g |
| $KH_2PO_4$ | 3.402 g |
| $NH_4Cl$ | 0.963 g |
| Nitrilotriacetic acid | 0.008 g |
| NaCl | 1.0 g |
| $FeCl_3$ | 0.487 mg |
| $FeSO_4 \cdot 7 H_2O$ | 5.6 mg |
| $MgSO_4 \cdot 7 H_2O$ | 250 mg |
| $CaCl_2 \cdot 2 H_2O$ | 20 mg |
| NaCl | 117 mg |
| $MnSO_4 \cdot 4 H_2O$ | 0.56 mg |
| $ZnSO4 \cdot 7 H_2O$ | 0.140 mg |
| $Co(NO_3)_2 \cdot 6 H2O$ | 0.150 mg |
| $CuSO_4 \cdot 5 H2O$ | 0.130 mg |
| $Na_2MoO_4 \cdot 2 H_2O$ | 0.120 mg |
| $H_3BO_3$ | 0.160 mg |
| EDTA III | 22.7 mg |

Substrate Tests

The following substrates (at concentrations ~1%) were tested on ADP1 strains: glucose, xylose, cellobiose, starch, acetate, succinate, casein amino acids, and algae biomass The compounds tested as carbon and energy source were provided by Sigma, if not stated otherwise. The strains B2, and strains lacking one of the following genes ACIAD3383, ACIAD2844, ACIAD2880, and ACIAD2837 were cultivated in 50 ml MA/9 medium at 30° C. and 300 rpm. Parallel cultivations with and without cas.amino acids were carried out. The optical densities ($OD_{600}$ value) were measured after 24 hours cultivation.

TABLE 3

Substrate utilization of the genetically modified strains variable substrates with or without casaminoacids. $OD_{600}$, 24 h

| | | ACIAD strain number | | | | |
| --- | --- | --- | --- | --- | --- | --- |
| | casam | B2 | 3383 | 2844 | 2880 | 2837 |
| Glucose | + | 9.64 | 13.51 | 10.29 | 12.44 | 11.32 |
| | − | 1.35 | 6.54 | 7.54 | 0.068 | 5.44 |
| Starch | + | 1.0 | 1.3 | 1.52 | 1.32 | 1.47 |
| | − | <0.1 | <0.1 | 0.1 | <0.1 | <0.1 |
| Cellobiose | + | 2.22 | 1.27 | 1.11 | 1.17 | 1.23 |
| | − | <0.1 | <0.1 | <0.1 | <0.1 | 0.1 |
| Xylose | + | 2.22 | 2.07 | 2.06 | 1.72 | 1.68 |
| | − | <0.1 | <0.1 | <0.1 | <0.1 | <0.1 |
| Algae biomass | + | ~4 | N.D. | N.D. | N.D. | N.D. |
| | − | ~2 | N.D. | N.D. | N.D. | N.D. |
| Acetate | + | 4.22 | N.D. | N.D. | N.D. | N.D. |
| | − | 0.21 | N.D. | N.D. | N.D. | N.D. |

TABLE 3-continued

Substrate utilization of the genetically modified strains variable substrates with or without casaminoacids. $OD_{600}$, 24 h

| | | ACIAD strain number | | | | |
| --- | --- | --- | --- | --- | --- | --- |
| | casam | B2 | 3383 | 2844 | 2880 | 2837 |
| Succinate | + | N.D. | N.D. | N.D. | N.D. | N.D. |
| | − | 1.23 | 0.70 | N.D. | N.D. | N.D. |
| Cas.amino acids | | 1.10 | 1.05 | 1.07 | 0.86 | 1.25 |

Of the tested substrates, glucose with and without amino acids was utilized most effectively, strains ACIAD3383 and ACIAD2844 possessing the highest $OD_{600}$ values. The minimal salts medium supplied only with cas. amino acids resulted in $OD_{600}$ value around one in all strains, suggesting that for example starch and cellobiose were utilized to only minor extent if any. However, the utilization of acetate demonstrates well the strain's capability to co-metabolism: the presence of amino acids boosts significantly the acetate utilization. Strain B2 was also cultivated on oil-extracted algae *Chlorella* residue as a carbon and energy source. The strain grew well on oil-extracted algae indicated that this material is potential raw material for cultivations. *Acinetobacter* strains were able to grow on glucose, which is important feature since glucose is a main component in sugar crop based carbohydrates, such as wheat or corn starch or sugar cane or beet sugar, and also in cellulose fraction of lignocellulosic materials such as agricultural residues (e.g. straw, stalk, bagasse), wood materials and herbaceous materials. *Acinetobacter* strains were able to grow also on xylose, which is important feature since xylose is abundant component is hemicellulose fractions of several lignocellulosic materials, e.g. agricultural residues like rice or wheat straw, corn stover or bagasse, wood materials like softwood and energy crops like switchgrass, reed canary grass, macroalgae (seeweed) and Miscanthus.

Antibiotic Tests

The sensitivity of ADP1 to different antibiotics was tested on LB medium and/or on LA plates. The antibiotics and concentrations used are listed in the Table 4. The antibiotics were provided by Sigma.

TABLE 4

The antibiotics and concentrations tested with ADP1.

| Antibiotic name | Concentration, µg/ml |
| --- | --- |
| Kanamycin | 15-250 |
| Tetracycline | 1-20 |
| Ampicillin | 100 |
| Chloramphenicol | 25-50 |

Genetic Engineering of ADP1

The molecular work was carried out by using methods well known to a person skilled in the art. For digestions and ligations, the enzymes and buffers were provided by Fermentas (Lithuania) and used according to provider's instructions. PCR reagents were provided by Finnzymes (Finland) (DNA polymerase Phusion™ and buffer) and Fermentas (nucleotides). Primers were ordered from ThermoFisher Scientific (USA) with appropriate restriction sites, and the annealing temperatures were calculated according to Finnzymes' instructions.

The transformation of ADP1 was carried out as follows; briefly, a linear DNA fragment with flanking regions of the target site in genome was inserted to ADP1 cultivation in an exponential growth phase. The cultivation was conducted at 30° C. and stirring of 300 rpm using LB medium supplied with 1% glucose. For transformation, ~2 µg DNA was used per 1 ml of cultivation. After insertion, the cultivation was incubated for 2-3 h and then spread on a selective LA plate supplied with an appropriate antibiotic and glucose. The plate was incubated at 30° C. until colonies appeared. Negative controls were cultivated in the same method except for insertions sterile water was used instead of DNA fragments.

Construction of Synthetic Gene Cassettes for Knock-Outs and Overexpression

The six gene cassette components were amplified separately by PCR: flanking region upstream of the target gene, for example ACIAD2837 (GeneY) was amplified from ADP1 by colony PCR with appropriate primers and flanking region downstream of the target gene, for example ACIAD2837 (GeneY'), respectively. The promoter T5 (lac/T5) was amplified from plasmid pCSS810 (Tauriainen et al. 1997). The selection marker kan(r) was amplified from the plasmid pET-28 (Novagen, USA) and cloned back to the plasmid in vitro using restriction enzymes XhoI and PstI and T4-DNA-ligase. The resulting plasmid was used as a PCR template for amplifying multiple cloning site (MCS) and kan(r) together. The selection marker cam(r) was amplified from the plasmid pAK400c. Transcription termination loop (t Ipp) was amplified from plasmid pAK400c. Double digestions were carried out for the PCR products with restriction enzymes and ligated in pairs. The ligation reactions were amplified by PCR with corresponding primers, digested again, and two of the pairs were ligated and amplified by PCR again. The two- and four-gene component sets were ligated and the whole gene cassette construct was amplified by PCR, the final product being ~2000 bp long. Purification of the PCR products was carried out in every step using PCR purification kit (Fermentas) or gel extraction kit (Fermentas). PCR products were run on 1-2% agarose (Sigma-Aldrich) gel supplied with SYBRsafe (Invitrogen, USA) and visualized with SafeImager (Invitrogen). The right construct was verified by sequencing.

For over-expression of a diacylglycerol acyltransferase, a codon-optimized synthetic gene (raSVa) with amino acid sequence analogous to sco0958 from *Streptomyces coelicolor* with appropriate restriction sites (NdeI, XhoI) was ordered from GenScript (USA). The codons were optimized based on the codon usage table of ADP1 preferring the triplets that are most abundant in the protein coding sequences of ADP1. The sequence was modified not to include any internal transcription termination loops or ribosome binding sites (RBS). The sequence data is presented in the Sequence listing as SEQ ID NO: 29. The synthetic gene was cloned into the gene cassette scaffold using restriction sites NdeI and XhoI.

By changing the ADP1 flanking regions in the cassette, the specific knock-out target site in the genome can be re-defined. By using different selection markers with variable flanking regions, mutants with multiple gene deletions can be constructed (Example: the strain Qm with deleted genes ACIAD3381, ACIAD3382, ACIAD3383, ACIAD3309). The gene cassette is integrated to a specific locus in ADP1 genome by homologous recombination The gene cassettes were transformed into *A. baylyi* B2 and ADP1 by natural transformation as described above. The transformants were selected on LA plates supplemented with appropriate antibiotic and the presence of the gene cassette was confirmed with PCR and further by sequencing.

Cultivations for Characterization of Lipid Producing Single Gene Knock-Out Mutants For determining the growth properties of the single gene knock-out mutants; the obtained strains were cultivated in 100 ml MA/9 medium supplemented with 0.2% casein amino acids and 1% glucose, at 37° C. and 300 rpm for 24 hours. The optical density (OD) was measured and the cells were collected and centrifuged at 5000 g for 1 hour. Thereafter, the cells were freeze dried in order to determine the cell dry weight gravimetrically.

For lipid analyses, the ADP1 strains (wild type (wt), ACIAD2837, ACIAD2844, ACIAD2880, ACIAD2291, ACIAD3316, SM100, ACIAD3381, ACIAD3309, ACIAD1134, and ACIAD2837) were cultivated in 100 ml MA/9 medium supplemented with 1% glucose, 0.2% cas.amino acids and 30 µg/ml kanamycin at 30° C. and 300 rpm for 24 hours. The cells were collected in two 45 ml samples, centrifuged at 5000 g for one hour, freeze dried and stored at −20° C. The biomass was used for determination of the cell dry weight, fatty/acid profile by gas chromatography (GC) analyses, and gravimetric analyses of total lipids.

Lipid Analyses

Lipid Extraction

The cells were centrifuged and dried after cultivation. The lipids were extracted using chloroform-methanol-PBS extraction method. For 45-50 ml of original culture 5 ml chloroform, 10 ml methanol and 4 ml PBS buffer (ratio 1:2: 0.8) was used. The volumes were scaled up when needed. The cell suspension was mixed well and stored in a shaker (150-200 rpm) for two hours. Another 5 ml of chloroform and 5 ml of PBS buffer (1:1) was added and the sample tube was mixed again and stored overnight in a refrigerator at 4° C. The lower (chloroform) phase was collected to a tared glass vial and evaporated under nitrogen. The extraction was repeated by adding 10 ml of chloroform to the original tube, and after mixing incubated for another 40 hours. Finally, the phase separation was completed by centrifugation at 3000 rpm for 20 minutes. The chloroform phase was transferred to the glass vial with the first extract and purged under nitrogen. The amount of total lipids was determined gravimetrically.

GC Run

Analysis of the fatty acid composition was carried out with gas chromatograph (GC) based on a standard procedure (ISO 15304) from lipids extracted from *Acinetobacter* biomass. In the method, the fatty acids in lipids were first transesterified to form fatty acid methyl esters (FAME) prior to analysis with gas chromatograph.

The main fatty acids in *Acinetobacter baylyi* ADP1 oil included C16:0, C16:1, C18:0 and C18:1 and C12:0, while the minor constituents included C13:1 and C14:0 fatty acids. The results of qualitative lipid analyses of ADP1 knock-out strains demonstrate the potential of ADP1 for bioenergy application; the main constituents of the fatty acid composition, C16 and C18, are known to be desirable raw materials for biodiesel or renewable diesel.

Example 2

Improvement of Storage Lipid Production in a Function of Time

Genetic engineering of strains was done as in example 1. The strains B2, ADP1 wt, ACIAD3383, ACIAD3381 were cultivated in 50 ml MA/9 medium supplemented with 0.2% cas.amino acids and 5% glucose. The cultivation was carried out at 37° C. and 300 rpm for 8 hours for each strain. Biomass of 2 ml samples was collected by centrifugation at 20000 g for 5 minutes and stored at −20° C.

TLC Analyses

For thin layer chromatography (TLC), lipid extraction was carried out in small-scale for 1.5-5 ml cultivation to quantify the amount of specific lipid components: the cells were centrifuged at 15000 rpm and the supernatant was discarded. Methanol (500 µl) was added on the cell pellets and tubes were shaken for one hour. Chloroform (250 µl) was added and tubes were shaken gently for additional hour. The tubes were centrifuged at 20000 g for 5 min. Additional 250 µl of chloroform and 250 µl of PBS were added to the tubes and the tubes were slowly swirlen overnight. The next day, the tubes were centrifuged at 20000 g for 5 min and lower phase (chloroform) was collected and 10-40 µl of the sample was applied to the TLC plate. The composition of mobile phase was n-hexane, ether and acetic acid in the ratio 80:20:2, respectively. The plates used were 10×20 cm or 20×20 cm Silica Gel 60 F254 with 2.5×10 cm concentration zone (Merck, USA) and dyed with iodine for visualization. Olive oil and trioleolylglycerol (Sigma) were used as standards. The ImageJ-software was used for measuring the intensity of the lipid spots in order to quantify specific lipid components.

Figure 2:
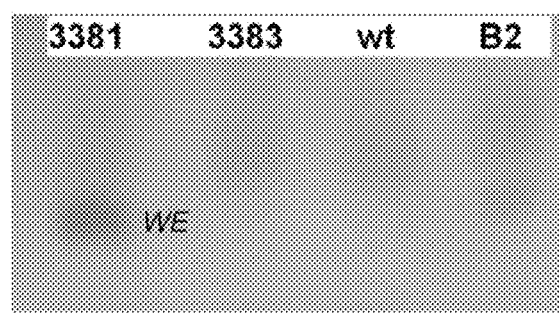
FIG. 2 presents the result of thin layer chromatography analyses; lipid production per cultivation time

Based on the densitometric analysis, the relative differences in WE and TAG production between the strains were estimated and proportioned to the wild type value. According to densitometric calculations, the strain ACIAD3381 produced 78 fold the amount of wax esters compared to ADP1 wild type strain (see FIG. 2) per the same cultivation time.

Example 3

Improvement of Storage Lipid Production Per Cell

Genetic engineering of strains was done as in example 1. The strains B2, ADP1 wt, ACIAD3381, ACIAD3383, ACIAD2880, ACIAD3648, ACIAD2837, ACIAD3309, ACIAD2177, ACIAD1121 and ACIAD0235 were cultivated in 50 ml MA/9 supplemented with 5% glucose and 0.2% cas.amino acids at 37° C. and 300 rpm for 30 hours. Samples containing same amount of biomass were centrifuged at 20000 g for 5 minutes and stored at −20° C.

The lipid extraction, TLC analyses and densitometric calculations were done as in example 2.

Figure 3:
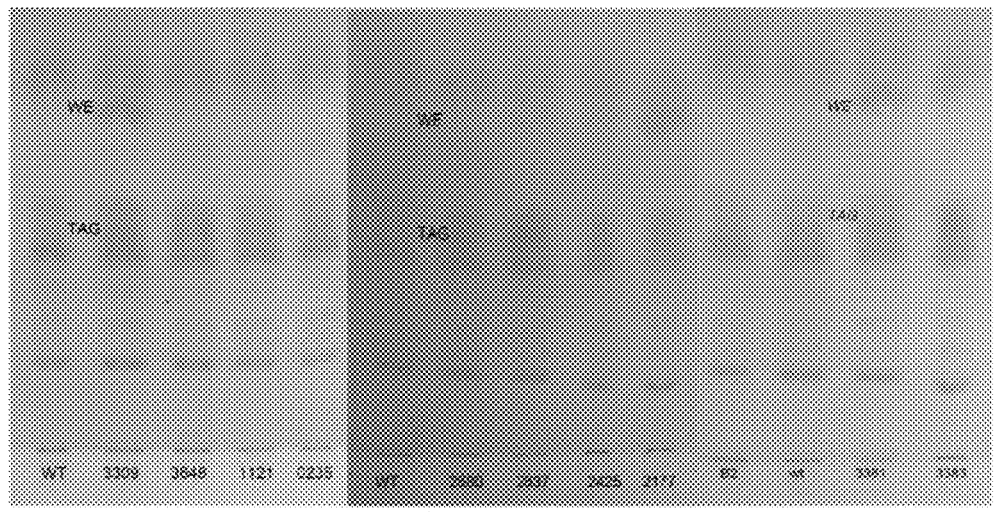
FIG. 3 presents the lipid production per cell

Based on the densitometric analysis, the relative differences in WE and TAG production between the strains were estimated and proportioned to the wild type value. It was calculated that for example ACIAD2177 produced 30 fold, ACIAD3309 produced 24 fold, ACIAD2837 produced 4 fold, ACIAD1121 produced 2 fold, ACIAD3648 produced 2 fold, and ACIAD3381 strain 17 fold the amount of wax esters compared to the wild type strain per cell weight. The ACIAD3383 produced TAG 1.5 fold compared to the wild type and ACIAD2425 1.3 fold compared to the wild type per cell weight (see FIG. 3).

Example 4

Improvement of Storage Lipid Production Per Cultivation Volume

Genetic engineering of strains was done as in example 1. The strains B2, ADP1 wt, ACIAD3381, ACIAD3383, ACIAD2880, ACIAD3648, ACIAD2425, ACIAD2837, ACIAD3309, ACIAD2177, ACIAD1121 and ACIAD0235 were cultivated in 50 ml MA/9 supplemented with 5% glucose and 0.2% cas.amino acids at 37° C. and 300 rpm for 30 hours. Samples of 2 ml were collected and centrifuged at 20000 g for 5 minutes and stored at −20° C.

The lipid extraction, TLC analyses and densitometric calculations were done as in example 2 in order to quantify the amounts of specific lipid components.

Figure 4:
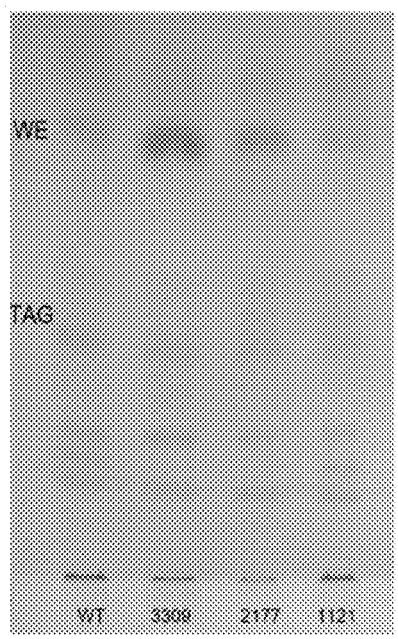
FIG. 4 presents the lipid production per cultivation volume

Based on the densitometric analysis, the relative differences in wax ester (WE) and TAG production between the strains were estimated and proportioned to the wild type value. It was calculated that for example ACIAD3381 produced 8 fold, ACIAD2837 produced 1.7 fold and ACIAD3309 about 20 fold the amount of wax esters compared to the wild type strain per cultivation volume (see FIG. 4). The ACIAD3383 produced TAG 2 fold compared to the wild type and ACIAD2837 produced 1.7 fold compared to the wild type per cultivation volume.

Example 5

The Production of Specific Lipid Compound (TAG)

Figure 5:
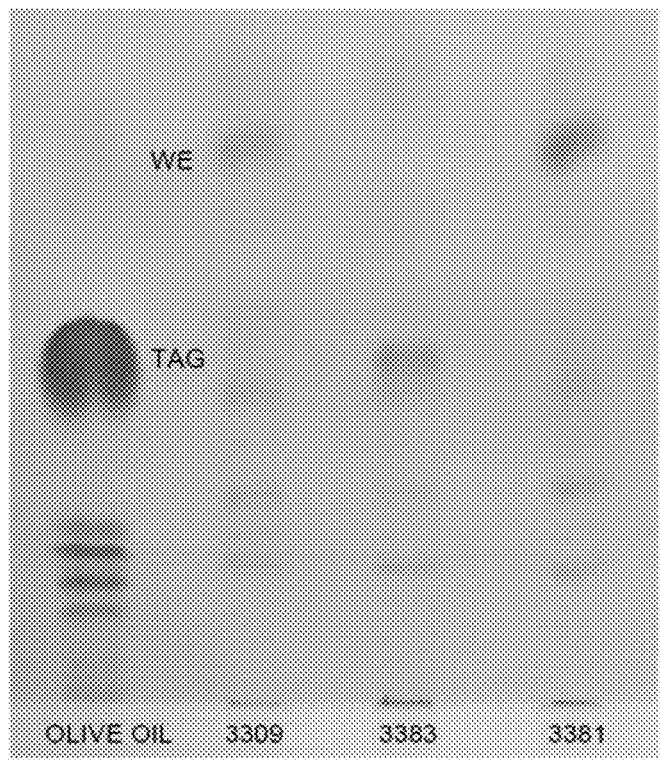
FIG. 5 presents the production of specific lipid compound (TAG)

Genetic engineering of strains was done as in example 1. The strains ACIAD3381, ACIAD3383 and ACIAD3309 were cultivated in 50 ml MA/9 supplemented with 5% glucose and 0.2% cas.amino acids at 37° C. and 300 rpm for 30 hours. Samples of 2 ml were collected and centrifuged at 20000 g for 5 minutes and stored at −20° C. The lipid extraction, TLC analyses and densitometric calculations were done as in example 2. Based on TLC analysis, the strain lacking the ACIAD3383 gene produces only TAGs as a storage lipid. The strains ACIAD3309 and ACIAD3381 produce TAGs and WEs (see FIG. 5).

Example 6

Lipid Production of a Strain with Four Gene Deletions

Genetic engineering of strains was done as in example 1. For the three single gene knock-out mutants (ACIAD3309, ACIAD3381, ACIAD3383) and the mutant Qm with four knock-outs (ACIAD3309, ACIAD3381, ACIAD3382, ACIAD3383, were cultivated in 100 ml medium I. 250 ml Erlenmeyer flasks. In the phase I, the strains were cultivated for 24 h in MA/9 medium supplemented with 2% sodium gluconate and 0.5% glycerol at 30° C., and 300 rpm. For phase II, the cells were collected by centrifugation (30 min., 3000 rpm) and suspended to fresh medium with reduced nitrogen concentration (0.1 g/l NH4Cl). The cultivation was continued additional 24 h in same conditions.

After the cultivation the cells were collected by centrifugation (45 min., 3000 rpm) and freeze-dried in parallel samples (40 ml cultivation). The cell dry weight of the samples was determined gravimetrically.

A total of 40 ml of original culture containing freeze-dried cells was extracted with 5 ml of chloroform, 10 ml of methanol and 4 ml of PBS buffer (ratio 1:2:0, 8 v/v/v). The cell suspension was mixed well and shaken for 2 h at 150-200 rpm. The mixture of 5 ml of chloroform and 5 ml of PBS buffer (1:1 v/v) was added, suspension was mixed well again and stored overnight in a refrigerator at +4° C. The suspension was centrifuged at 7000 rpm for 10 min. The lower (chloroform) phase was collected into a pre-weighted glass vial and evaporated under nitrogen. The extraction was repeated by adding 10 ml of chloroform to the upper water-methanol phase containing the cells and after mixing incubated for 40 hours at +4° C. Finally, the phase separation was completed by centrifugation at 7000 rpm for 20 min. The chloroform phase was transferred to the glass vial with the first extract and purged under nitrogen.

In order to determine the TAG content of the samples, preparative TLC analyses were carried out using 10×20 cm Silica Gel 60 F254 glass plates with 2,5×10 cm concentrating zone (Merck) and dyed with iodine for visualization. Mobile phase was n-hexane:diethyl ether:acetic acid 80:20:2. Tripalmitoyl-glycerol (Sigma) was used as a standard. After evaporation of iodine Silica Gel from desired TAG-zone was scraped by a metal spatula and transferred into a clean Pasteur pipet containing cotton wool. TAG were eluted from Silica Gel with chloroform (3×0.7 ml). Chloroform was purged under nitrogen. The amount of TAG was determined gravimetrically (Table 2).

TABLE 2

|  | dry biomass (mg) | TAG (mg) | TAG/biomass |
|---|---|---|---|
| wild type | 125 | 0.15 | 0.12% |
| Qm | 90 | 0.6 | 0.67% |
| 3383 | 106.5 | 0.5 | 0.47% |
| 3309 | 128.5 | 0.65 | 0.51% |

Figure 6:
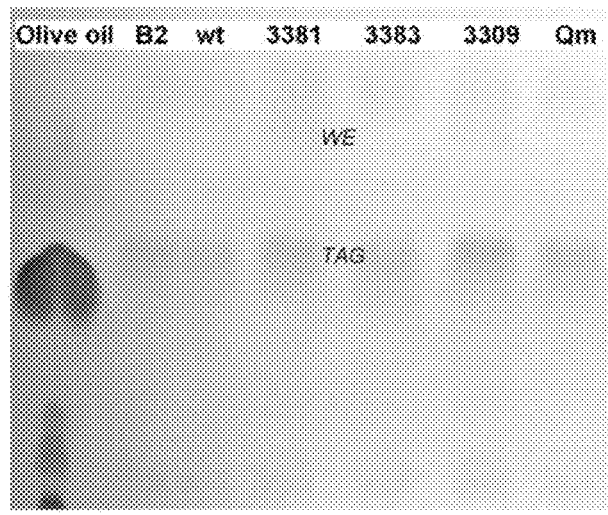
FIG. 6 shows a comparative TLC for the B2 and ADP1 wild types, single gene ko-mutants and Qm with four gene deletions.
Figure 7:
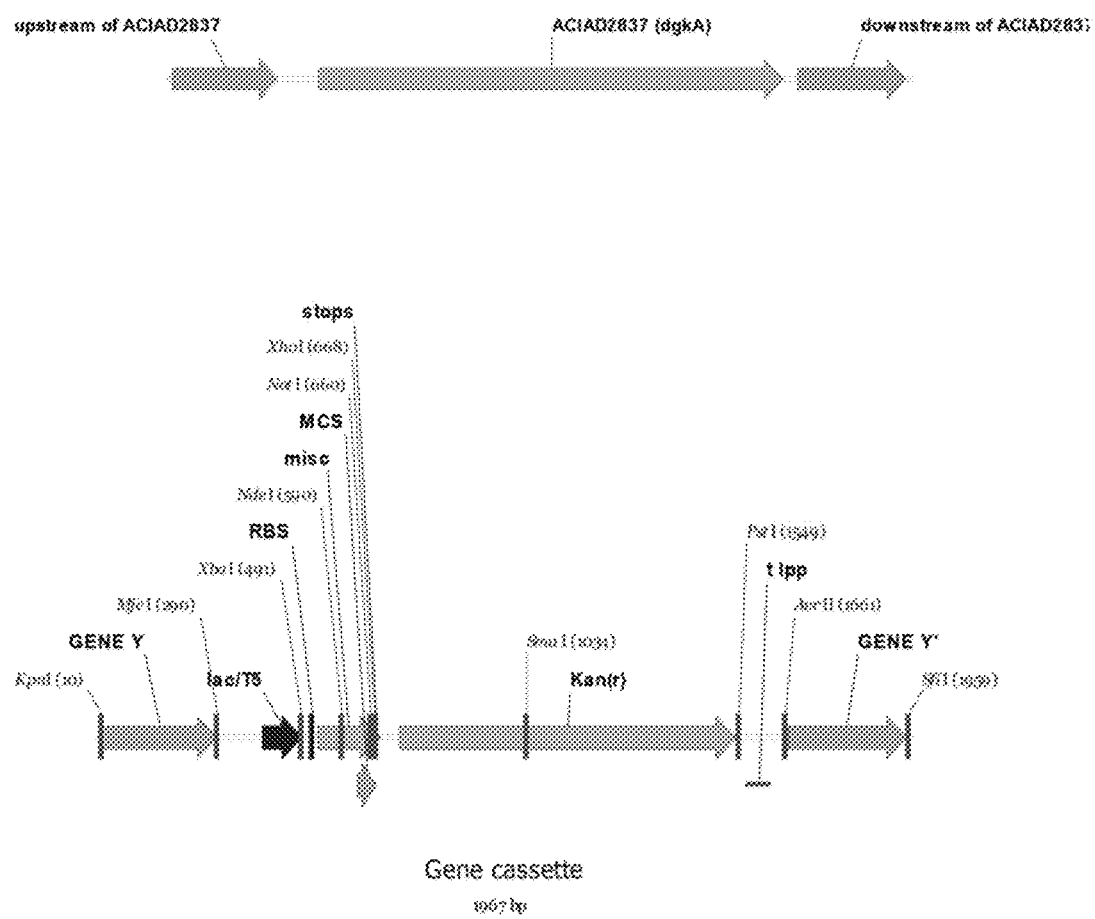
FIG. 7 shows flanking regions from the target gene to be knocked-out are cloned to the gene cassette. The synthetic gene cassette is used for gene knock-outs
Figure 8:
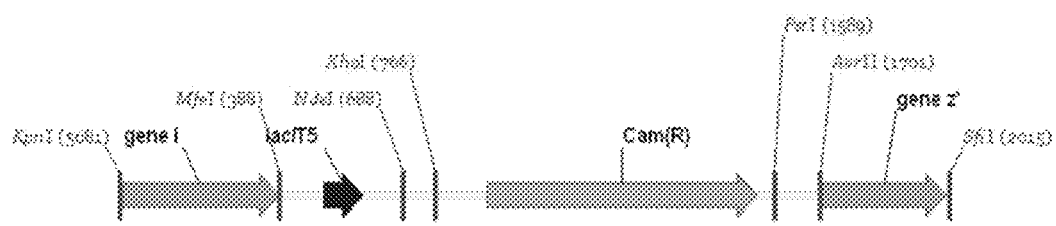
FIG. 8 shows an example of a gene cassette for knock-out of multiple genes
Figure 9:
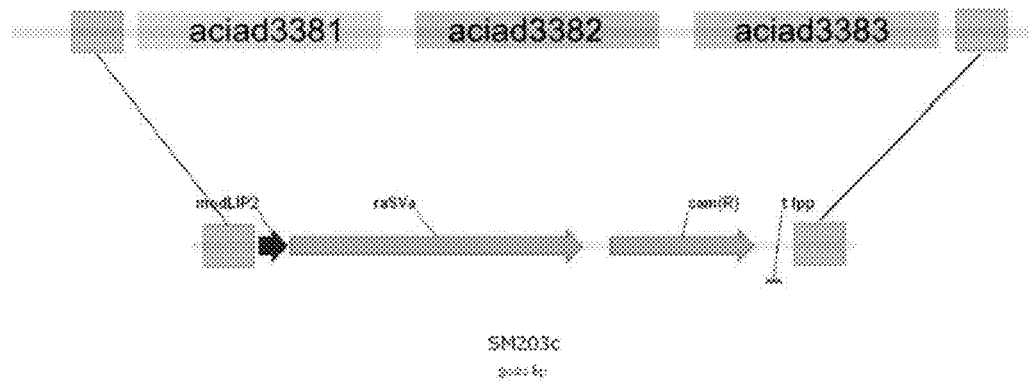
FIG. 9 shows a gene cassette for knock-out of three genes and over-expression of the synthetic gene raSVa.

The change in phenotype resulted from the knock-outs can be seen for the strain Qm: wax ester production has been blocked (see FIG. 6). Thus it can be concluded that the strain Qm produces most TAG among the strains that do not produce wax esters.

Example 7

Over-Expression of aftA

The natural capability of *Acinetobacter* strains to produce storage lipids, such as TAG and WE, can be further improved by over-expressing the key enzyme WS and/or DGAT, or a gene coding function equivalent. The gene encoding WS and/or DGAT is naturally present in the *Acinetobacter* genome or can be obtained from other native sources or is synthetically constructed. The gene is amplified with PCR and cloned to a suitable gene cassette for over-expression. The construction of a gene cassette can be done as described in example 1. The suitable gene cassette contains flanking regions for targeted knock-out, selection marker, promoter for aftA expression and a transcription termination loop. The over-expression promoter is preferentially inducible, and obtained from *A. baylyi* or other source. For example, the following promoters can be used for aftA overexpression: T5 promoter, the lactose promoter or the arabinose promoter. If needed, the gene cassette contains accessory genes to control promoter activity such as a gene encoding repressor for arabinose promoter. The gene cassette is transformed in *Acinetobacter* strain as described in example 1. The effect of aftA expression on storage lipid production is shown by lipid analyses.

REFERENCES

Altschul, S. F., T. L. Madden, A. A. Schäffer, J. Zhang, Z. Zhang, W. Miller and D. J. Lipman 1997. Gapped BLAST and PSI-BLAST: a new generation of protein database search programs. Nucleic Acids Res. 25:3389-3402.

Arabolaza, A, Rodriguez, E, Altabe, S, Alvarez, H and Gramajo, H (2008) Multiple pathways for triacylglyserol biosynthesis in *Streptomyces coelicolor*. Appl Env Microb 79: 2573-2582.

Coen, D. M. 2001 The polymerase chain reaction, published in Ausubel F M, Brent R, Kingston R E, More D D, Seidman J G, Smith K. and Struhl K (eds.) Current protocols in molecular biology. John Wiley & Sons. Inc., Hoboken, USA).

Fixter, L. M., Nagi, M. N., McCormack, J. G. and Fewson, C. A., *Structure, Distribution and Function of Wax Esters in Acinetobacter calcoaceticus* Journal of General Microbiology 1986. 132: p. 3 147-3 157.

Gellissen, G., (ed). (2005). Production of recombinant proteins. Novel microbial and eukaryotic expression systems. Wiley-VCH Verlag GmbH & Co. Weinheim, Germany.

Kalscheuer, R. and Steinbüchel, A., A novel bifunctional wax ester synthase/acylCoA:diacylglycerol acyltransferase mediates wax ester and triacylglycerol biosynthesis in *Acinetobacter* calcoaceticus ADP1. J Biol Chem, 2003. 278(10): p. 8075-82.

Krehenbrink, M., Oppermann-Sanio, F. B. and Steinbüchel, A., Evaluation of non-cyanobacterial genome sequences for occurrence of genes encoding proteins homologous to cyanophycin synthetase and cloning of an active cyanophycin synthetase from *Acinetobacter* sp. strain DSM 587. Arch Microbiol, 2002. 177(5): p. 371-80.

Metzgar, D., Bacher, J. M., Pezo, V., Reader, J., Doring, V., Schimmel, P., Marliere, P. and de Crecy-Lagard. V., *Acinetobacter* sp. *ADP1: an ideal model organism for genetic analysis and genome engineering*. Nucleic Acids Res, 2004. 32(19): p. 5780-90.

Miller, L. Quantifying western blots without expensive commercial quantification software. 2007 [cited 2010 01/271]; Available from: Luke Miller's website.

Ratledge, C., Cohen, Z. 2008. Microbial and algal oils: Do they have a future for biodiesel or as commodity oils. Lipid Technology 20:155-160.

Rice, P., Longden, I. and Bleasby, A. (2000) EMBOSS: the European Molecular Biology Open Software Suite, Trends Genet, 16, 276-277.

Sambrook, J., Fritsch, E. F. and Maniatis, T., *Molecular Cloning: a Laboratory Manual.* 1990, Cold Spring Harbor, N.Y.: Cold Spring Harbor Laboratory Press Sambrook and Russell (2001). *Molecular Cloning: A Laboratory Manual* (3rd ed.). Cold Spring Harbor Laboratory Press.

Santala, V. and Lamminmäki, U., Production of a biotinylated single-chain anti-body fragment in the cytoplasm of *Escherichia coli*. J Immunol Methods, 2004. 284(1-2): p. 165-175.

Stöveken, T. and Steinbuchel, A., Bacterial acyltransferases as an alternative for lipase-catalyzed acylation for the production of oleochemicals and fuels. Angew Chem Int Ed Engl, 2008. 47(20): p. 3688-94.

Tauriainen, S., Karp, M., Chang, W. and Virta, M., Recombinant luminescent bacteria for measuring bioavailable arsenite and antimonite. Appl Environ Microbiol, 1997. 63(11): p. 4456-4461.

The invention claimed is:

1. A genetically modified *Acinetobacier* host for lipid production, wherein
(a) the host has been modified genetically by transformation and recombination to be deficient of gene ACIAD 2177 (SEQ ID NO:4) or a gene haying at least 95% sequence identity to ACIAD 2177 (SEQ ID NO:4). and
(b) the host further has been modified genetically by transformation and recombination to be deficient of one or more genes selected from a group consisting of a gene encoding fatty acyl-CoA reductase (EC1.2.1,n2), gene ACIAD 3383 (SEQ ID NO:1) or a gene having at least 95% sequence identity to ACIAD 3383 (SEQ ID NO: 1): a gene encoding lipase (EC:3.1.1.3) gene ACIAD 3309 (SEQ ED NO: 2) or a gene having at least 95% sequence identity to ACIAD 3309 (SEQ ID NO:2) a gene encoding pyruvate dehydrogenase (EC:1.2.2.2), gene ACIAD 3381 (SEQ ID NO:3) or a gene haying at least 95% sequence identity to ACIAD 3381 (SEQ ID NO:3); a gene encoding diacylglycerol kinase (EC:2.7.1.107), gene ACIAD 2837 (SEQ ID NO:5 or a gene having at least 95% sequence identity to ACIAD 2837 (SEQ ID NO:5); a gene encoding succinate dehydrogenase (EC: 1.3.5.1), gene ACIAD 2880 (SEQ ID NO:6) or a gene having at least 95% sequence identity to ACIAD 2880 (SEQ ID NO:6); a gene encoding glycerol-3-phosphate dehydrogenase (EC 1.1.5.3), gene ACIAD 2844 (SEQ ID NO:7) or a gene having at least 95% sequence identity to ACIAD 2844 (SEQ ED NO:7); a gene encoding cytochrome o ubiquinol oxidase subunit II (EC: 1.10.3.~), gene ACIAD 2425 (SEQ ID NO:8) or a gene having at least 95% sequence identity to ACLAD 2425 (SEQ ID NO:8); a gene encoding cytochrome o ubiquinol oxidase subunit I (EC:1.10.3.~), gene ACIAD 2426 (SEQ ID NO:9), or a gene having at least 95% sequence identity to ACIAD 2426 (SEQ ID NO:9); a gene encoding cytochrome d terminal oxidase polypeptide subunit II (EC1.10.3.~), gene ACIAD 2291 (SEQ ID NO:10, or a gene having at least 95% sequence identity to ACIAD 2291 (SEQ ID NO:10); a gene encoding carboxylesterase (EC:3.1.1.1), gene ACIAD 3648 (SEQ ID NO:11), or a gene having at least 95% sequence identity to ACRID. 3648 (SEQ ID NO: 11), a gene encoding esterase, gene ACIAD 1134 (SEQ ID NO:12), or a gene haying at least 95% sequence identity to ACIAD 1134 (SEQ ID NO:12), various lipases (EC: 3.1.1.3), a gene ACIAD 1121 (SEQ ID NO: 13) or a gene having at least 95% sequence identity to ACIAD 1121 (SEQ ID NO:13), and a gene encoding acyl-CoA synthetase (EC:6.2.1.3), gene ACIAD 0235 (:SEQ ID NO:14) or a gene having at least 95% sequence identity to ACIAD 0235 (SEQ ID NO:14),
wherein said host has increased production of wax ester, triacylglycerols, or total lipids compared to the unmodified *Acinetobacter* host.

2. The host according to claim 1, wherein the host been genetically modified to express one or more genes encoding the enzymes of lipid biosynthesis pathway.

3. The host according to claim 1, wherein the host been genetically modified to express a gene encoding diacylglycerol synthase enzyme (EC 2.3.1.20) or to express a gene encoding WS or DGAT (EC 2.3.1.75 and EC 2.3.1.20).

4. The host according to claim 1, wherein the host is genetically modified to express a gene selected from the group of
(a) sco0958 (SEQ ID NO: 29) or aftA (SEQ ID NO: 31);
(b) a gene from a *Streptomyees* species, said gene encoding diacylglycerol synthase enzyme (EC 2.3.1.20); or a gene from are *Acittetobacter* species, said gene encoding WS or DGAT (EC 2.3.1.75 and EC 2,3.1,20);
(c) a nucleotide sequence Which hybridizes to SEQ ID NO: 29 under stringent hybridization conditions and encodes diacylglwerol synthase enzyme (EC 2.3.1.20) activity or a nucleotide sequence which hybridizes to SEQ ID NO:

31 under stringent hybridization conditions and encodes WS or DGAT (EC 2.3.1.75 and EC 2.3.1.20): and
(d) a nucleotide sequence encoding the amino acid sequence SEQ ID NO:30, or a sequence having at least 95% identity to said sequence and having diacylglycerol synthase enzme activity (EC 2.3.1.20), or a nucleotide sequence encoding the amino acid sequence SEQ ID NO:32 or a sequence having at least 95% identity to said sequence and having WS or DGAT (EC 2.3.1.75 and EC 2.3.1.20) activity.

5. A method for making the genetically modified *Acinetobacter* host of claim 1 which comprises steps of: making the host deficient of gene ACIAD 2177 (SEQ ID. NO:4) or a gene haying at least 95% sequence identity to ACIAD 2177 (SEQ ID NO:4) by transformation and recombination and further by making the host deficient of one or more genes selected from the group consisting of a gene encoding fatty acyl-CoA reductase (EC1.2.1.n2), gene ACIAD 3383 (SEQ ID NO:1) or a gene haying at least 95% sequence identity to ACIAD 3383 (SEQ ID NO:1), a gene encoding lipase (EC:3.1.13), gene ACIAD 3309 (SEQ ID NO: 2) or a gene having at least 95% sequence identity to ACIAD 3309 (SEQ ID NO:2), a gene encoding pyruvate dehvdrogenase (EC:1.2.2.2). gene ACIAD 3381 (SEQ ID NO:3) or a gene haying at least 95% sequence identity to ACIAD 3381 (SEQ ID NO:3), a gene encoding diacviglyceral kinase (EC:2.7.1.107), gene ACIAD 2837 (SEQ ID NO:5) or a gene having at least 95% sequence identity to ACIAD 2837 (SEQ ID NO:5) a gene encoding succinate dehydrogenase (EC:1.3.5.1). gene ACIAD 2880 (SEQ ID NO:6) or a gene having at least 95% sequence identity to ACIAD 2880 (SEQ ID NO:6), a gene encoding glycerol-3-phosphate dehydrogenase (EC:1.1.5.3.), gene ACIAD 2844 (SEQ ID NO:7) or a gene having at least 95% sequence identity to) ACIAD 2844 (SEQ ID NO:7) a gene encoding cytochrome o ubiquinol oxidase subunit II (EC: 1.10.3.~), gene ACIAD 2425 (SEQ ID NO:8) or a gene having at least 95% sequence identity to ACIAD 2425 (SEQ ID NO:8), a gene encoding cytochrome a ubiquinol oxidase subunit I (EC:1.10.3.~gene ACIAD 2426 (SEQ ID NO:9), or a gene having at least 95% sequence identity to ACIAD 2426 (SEQ ID NO:9), a gene encoding cytochrome d terminal oxidase polypeptide subunit II (EC1.10.3.~), gene ACIAD 2291 (SEQ ID NO:10), or a gene having at least 95% sequence identity to ACIAD 2291 (SEQ ID NO:10), a gene encoding carboxylesterase (EC:3.1.1.1), gene ACIAD 3648 (SEQ ID NO:11), or a gene having at least 95% sequence identity to ACIAD 3648 (SEQ ID NO:11). a gene encoding esterase. gene ACIAD 1134 (SEQ ID NO:12). or a gene having at least 95% sequence identity to ACIAD 1134 (SEQ ID NO:12), gene ACIAD 1121 (SEQ ID NO:13) or a gene having at least 95% sequence identity to ACIAD 1121 (SEQ ID NO: 13); and a gene encoding acyl-CoA synthetase (EC: 6213), gene ACIAD 0235 (SEQ ID NO: 14) or a gene having at least 95% sequence identity to ACIAD 0234 (SEQ ID NO: 14) by transformation and recombination.

6. A method according to claim 5, further comprising, introducing into said host a gene selected from sc958 and aftA, or further comprising overexpressing: gene aftA in said host.

7. A process for producing lipids, which comprises
(a) cultivating an *Acinetobacier* host according to claim 1 under suitable cultivation conditions:
(b) allowing the *Acinetobacter* host to produce or accumulate lipids; and
(c) recovering the lipids.

8. A method for producing biofuel, which
(a) cultivating an *Acitietobacter* host according, to claim 1 under suitable cultivation conditions;
(b) allowing the *Acinetobacter* host to produce or accumulate lipids;
(c) recovering the lipids, and
(d) producing biofuel using the recovered lipids as a component or as starting material for biofuel production.

* * * * *